US007678785B2

(12) United States Patent
Carr et al.

(10) Patent No.: US 7,678,785 B2
(45) Date of Patent: Mar. 16, 2010

(54) SUBSTITUTED ANILINE DERIVATIVES

(75) Inventors: Andrew David Carr, Cambridge (GB);
Judi Charlotte Neuss, Slough (GB);
Michael Glen Orchard, Slough (GB);
David William Porter, West Sussex (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 11/782,337

(22) Filed: Jul. 24, 2007

(65) Prior Publication Data
US 2008/0045497 A1    Feb. 21, 2008

(30) Foreign Application Priority Data

| Jul. 24, 2006 | (GB) | 0614677.3 |
| Jul. 24, 2006 | (GB) | 0614678.1 |
| Mar. 9, 2007 | (GB) | 0704645.1 |
| Mar. 9, 2007 | (GB) | 0704648.5 |

(51) Int. Cl.
*A61K 31/4025* (2006.01)
*A61K 31/397* (2006.01)
*A61K 31/445* (2006.01)
*A61K 31/4468* (2006.01)
*A61K 31/55* (2006.01)
*A61K 31/551* (2006.01)
*A61K 31/495* (2006.01)
*C07D 207/04* (2006.01)
*C07D 211/06* (2006.01)
*C07D 241/04* (2006.01)
*C07D 243/08* (2006.01)

(52) U.S. Cl. .......................... 514/210.17; 514/211.01; 514/255.01; 514/317; 514/423; 514/211.08; 540/553; 540/607; 544/386; 544/382; 546/192; 546/245; 548/540; 548/953

(58) Field of Classification Search ................. 514/423; 548/540
See application file for complete search history.

(56) References Cited

U.S. PATENT DOCUMENTS 4,736,066 A * 4/1988 Natarajan et al. ........... 564/185
6,350,761 B1    2/2002 Guilford et al.

FOREIGN PATENT DOCUMENTS

JP         2005202314        7/2005

OTHER PUBLICATIONS

Wu and Farrelly, Toxicology 236:1-6, 2007.*
Vippagunta et al., Advanced Drug Delivery Reviews, p. 1.*
Gorgon et al., Biochemical and Biophysical Research Communications (1984), 124(1), 148-55, Abstract and STN search report.*
Henry, David W., "A Facile Synthesis of Piperazines from Primary Amines (1)," J. Het. Chem. 3:503-511 (1966).
Ichikawa, T. et al., "Optically active antifungal azoles. XIII," Chem. Pharm. Bull. 49(9):1110-1119(2001).
Tisnes, P. et al., "Macrocyclic polyether tetralactams I: Synthesis and cyclization studies," Tetrahedron 48(21):4347-4358 (1992).
Tsien, R.Y. et al., Biologically useful chelators that take up Ca2+ upon illumination, J. Am. Chem. Soc.111:7957-7968 (1989).
PCT/GB07/002815 Search Report dated Oct. 4, 2007.
Registry, MARPAT and Derwent Wpindex Search dated Aug. 2, 2005 (S050207a).
Registry, MARPAT and Derwent Wpindex Search dated Aug. 2, 2005 (S050207c).
Registry, MARPAT Search dated Aug. 2, 2005 (S050208a).
Registry, Chem Abstrats, MARPAT, and Derwent Wpindex Search dated Oct. 2, 2005 (S050209a).
Registry, Chem Abstracts, MARPAT, and Derwent Wpindex Search dated Oct. 2, 2005 (S050209b).
Registry, Chem Abstracts, MARPAT and Derwent Wpindex Search dated Oct. 2, 2005 (S050209c).

* cited by examiner

*Primary Examiner*—Yong Chu
(74) *Attorney, Agent, or Firm*—Wilson Sonsini Goodrich & Rosati

(57) ABSTRACT

The present invention relates to novel aniline derivatives and their use in therapy, in particular their use in the treatment of fungal infections.

22 Claims, 1 Drawing Sheet

SUBSTITUTED ANILINE DERIVATIVES

CROSS-REFERENCE

This application claims the right of priority under 35 USC §119 (a)-(d) of GB 0614678.1, filed Jul. 24, 2006; GB 0614677.3, filed Jul. 24, 2006; GB 0704645.1, filed Mar. 9, 2007; and GB 0704648.5, filed Mar. 9, 2007, each of which is incorporated by reference herein in its entirety.

BACKGROUND OF THE INVENTION

Many different species of fungi live harmlessly on the skin and inside the body of all animals including humans. However under certain circumstances, often as a result of a weakened or suppressed immune system, individuals will succumb to opportunistic fungal infections. The infections may be superficial or systemic. Superficial infections such as athletes' foot, ringworm and thrush are generally caused by pathogenic fungi. They are slow to develop, often remaining asymptomatic for many years, and are generally well tolerated or treated. Systemic infections are caused by primary and opportunistic fungi. They develop rapidly in susceptible hosts and hence require rapid treatment, often before diagnosis and tend to be associated with a poor prognosis. These usually occur in hospitalized patients.

The incidence of life-threatening fungal infections has increased dramatically as the population of immunocompromised individuals (including cancer, organ transplant and AIDS patients) has increased. As a result it is the cause of an increasing financial and logistic burden on the medical care system and its providers.

To date a number of different targets and metabolic pathways have been exploited clinically to kill fungi or inhibit their growth. The most recent approach to emerge targets the organisms' need to synthesise glucan. Glucan, in particular $\beta$-1,3-D-glucan, is essential to the integrity of the cell wall of a wide range of fungi, in particular the *Candida* and *Aspergillus* species. The main enzyme activity responsible for glucan synthesis within fungi is 1,3-$\beta$-D-glucan synthase. Inhibitors of this activity prevent the synthesis of glucan and thereby compromise the integrity of the cell wall, leading to destruction of the cell.

A class of compounds called echinocandins are known to act as glucan synthase inhibitors and include caspofungin acetate, micafungin and anidulafungin. The chemical structure of caspofungin acetate is shown below. The other echinocandin compounds have very similar structures.

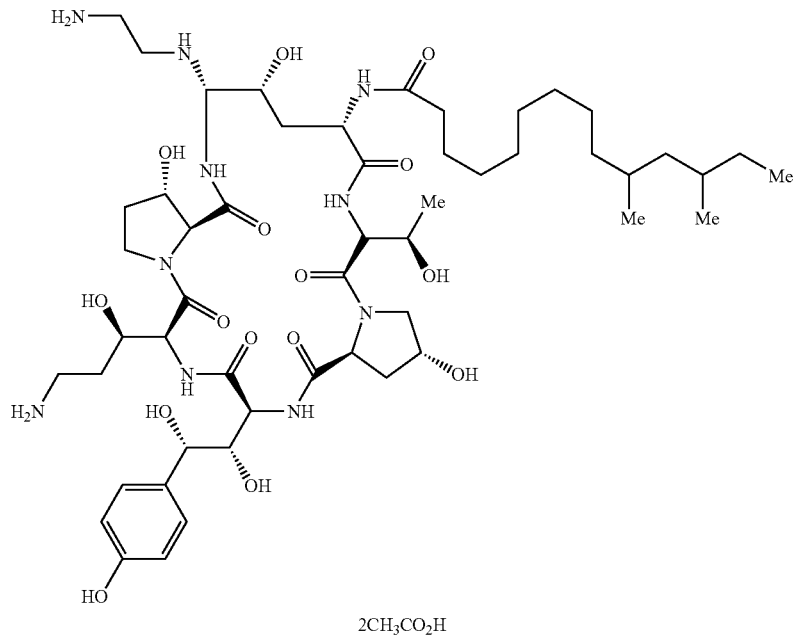

Although the echinocandins have met some success in their antifungal action, it would be desirable to provide compounds that provide comparable glucan synthase inhibition and which have improved pharmacokinetic properties and which are relatively small organic molecules which are easier to manufacture.

SUMMARY OF THE INVENTION

Provided herein are compounds that are useful as antifungal agents. Also provided are pharmaceutical compositions that include such antifungal agents. Also provided herein are methods of using such compounds for the treatment of diseases, disorders or conditions caused, exacerbated, or otherwise induced or related to fungi.

Provided herein are compounds or pharmaceutically acceptable salts of Formula I:

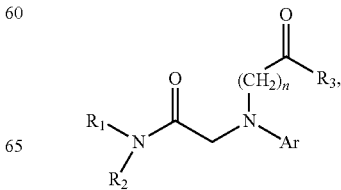

(Formula I)

wherein, n is 0, 1, or 2;

$R_1$ and $R_2$ are independently selected from H, $(C_1$-$C_6)$ alkyl, $(C_1$-$C_6)$alkenyl, $(C_1$-$C_6)$alkynyl, $(C_1$-$C_6)$heteroalkyl, $(C_1$-$C_6)$heteroalkenyl, $(C_3$-$C_8)$cycloalkyl, $(C_3$-$C_8)$cycloalkenyl, $(C_3$-$C_8)$heterocycloalkyl, $(C_3$-$C_8)$heterocycloalkenyl, aryl, and heteroaryl, any of which is optionally substituted with 1 or 2 independently selected $R_x$ groups;

or $R_1$ and $R_2$ together with the nitrogen atom to which they are attached form a 4- to 8-membered heterocycloalkyl or heterocycloalkenyl group, any of which is optionally substituted with 1 or 2 independently selected $R_x$ groups;

Ar is selected from phenyl, naphthyl, and a monocylic or bicyclic heteroaryl group, any of which is optionally substituted with 1 or 2 independently selected $R_x$ groups, or with a phenyl, O-phenyl, or $OCH_2$-phenyl in which the phenyl group is further optionally substituted with 1 or 2 independently selected $R_x$ groups;

$R_3$ is $L_1$-$L_2$-$R_4$, where $L_1$ is selected from a bond, O, $NR_1$, and S; $L_2$ is selected from a bond, $(C_1$-$C_6)$alkyl, $(C_1$-$C_6)$alkenyl, $(C_1$-$C_6)$alkynyl, $(C_1$-$C_6)$heteroalkyl, $(C_1$-$C_6)$heteroalkenyl, $(C_3$-$C_8)$cycloalkyl, $(C_3$-$C_8)$cycloalkenyl, $(C_3$-$C_8)$heterocycloalkyl, and $(C_3$-$C_8)$heterocycloalkenyl; and $R_4$ is selected from H, cycloalkyl, cycloalkenyl, heterocycloalkyl, heterocycloalkenyl, aryl, and heteroaryl, any of which is optionally substituted with 1 or 2 independently selected $R_x$ groups;

$R_x$ is be $L_{s1}L_{s2}R_s$, wherein each $L_{s1}$ and $L_{s2}$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, $(C_1$-$C_6)$alkyl, and —$(C_2$-$C_6)$alkenyl; and $R_s$ is selected from hydrogen, alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, isocyanato, thiocyanato, isothiocyanato, nitro, perhaloalkyl, perfluoroalkyl, silyl, and amino, including mono- and di-substituted amino groups, and the protected derivatives thereof;

or a pharmaceutically acceptable salt, prodrug, solvate, polymorph, tautomer, or isomer thereof, or an active metabolite thereof.

Provided herein are compounds or pharmaceutically acceptable salts of Formula II:

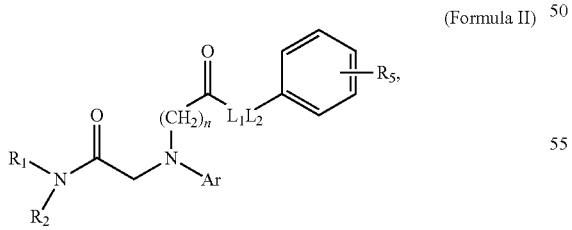

(Formula II)

wherein:

n is 0 or 1, $R_5$ is selected from halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —$NHSO_2H$, —$NHSO_2$($C_1$-$C_6$ alkyl), —N($C_1$-$C_6$ alkyl)$SO_2H$, —N($C_1$-$C_6$ alkyl)$SO_2$($C_1$-$C_6$ alkyl), —$CONH_2$, —CONH($C_1$-$C_6$ alkyl), —CON($C_1$-$C_6$ alkyl)$_2$, and $SO_2$($C_1$-$C_6$ alkyl), or a pharmaceutically acceptable salt, prodrug, solvate, polymorph, tautomer, or isomer thereof.

Provided herein are compounds or pharmaceutically acceptable salts of Formula III:

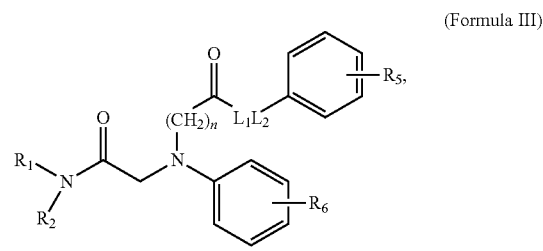

(Formula III)

wherein:

n is 0 or 1;

$R_5$ is selected from hydrogen, halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —$NHSO_2H$, —$NHSO_2$($C_1$-$C_6$ alkyl), —N($C_1$-$C_6$ alkyl)$SO_2H$, —N($C_1$-$C_6$ alkyl) $SO_2$($C_1$-$C_6$ alkyl), —$CONH_2$, —CONH($C_1$-$C_6$ alkyl), —CON($C_1$-$C_6$ alkyl)$_2$, and $SO_2$($C_1$-$C_6$ alkyl); and $R_6$ is selected from hydrogen, halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —$CO_2H$, or —$CO_2$($C_1$-$C_6$ alkyl), or a pharmaceutically acceptable salt, prodrug, solvate, polymorph, tautomer, or isomer thereof.

Provided herein are compounds or pharmaceutically acceptable salts of Formula IV or Formula V:

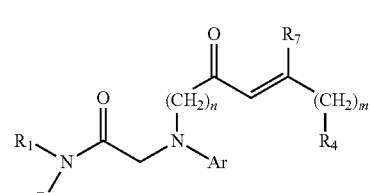

Fomula IV

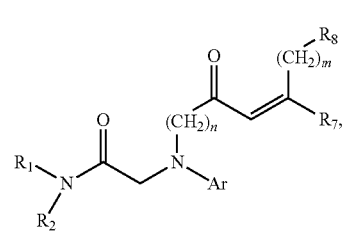

Formula V wherein:

$R_7$ is hydrogen, halogen, or $C_1$-$C_6$ alkyl; and $R_8$ is a phenyl group optionally substituted with one or two groups independently selected from halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —NHSO$_2$H, —NHSO$_2$($C_1$-$C_6$ alkyl), —N($C_1$-$C_6$ alkyl)SO$_2$H, —N($C_1$-$C_6$ alkyl)SO$_2$($C_1$-$C_6$ alkyl), —CONH$_2$, —CONH($C_1$-$C_6$ alkyl), —CON($C_1$-$C_6$ alkyl)$_2$, and SO$_2$($C_1$-$C_6$ alkyl), or a pharmaceutically acceptable salt, prodrug, solvate, polymorph, tautomer, or isomer thereof.

Provided herein are compounds or pharmaceutically acceptable salts of Formula VI or Formula VII:

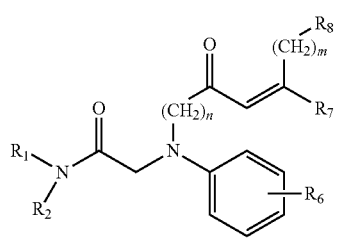

Formula VI

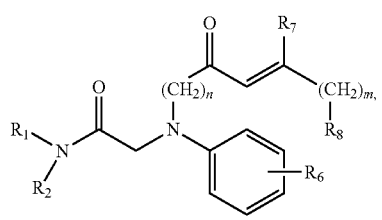

Formula VII wherein:
R$_6$ is selected from hydrogen, halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —CO$_2$H, or —CO$_2$($C_1$-$C_6$ alkyl);

R$_7$ is hydrogen, halogen, or $C_1$-$C_6$ alkyl; and

R$_8$ is a phenyl group optionally substituted with one or two groups independently selected from halogen, $C_1$-$C_6$ alkyl, hydroxy, —O($C_1$-$C_6$ alkyl), —NH$_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —NHSO$_2$H, —NHSO$_2$($C_1$-$C_6$ alkyl), —N($C_1$-$C_6$ alkyl)SO$_2$H, —N($C_1$-$C_6$ alkyl)SO$_2$($C_1$-$C_6$ alkyl), —CONH$_2$, —CONH($C_1$-$C_6$ alkyl), —CON($C_1$-$C_6$ alkyl)$_2$, and SO$_2$($C_1$-$C_6$ alkyl), or a pharmaceutically acceptable salt, prodrug, solvate, polymorph, tautomer, or isomer thereof.

In some embodiments, R$_1$ and R$_2$, together with the nitrogen atom to which they are attached form a heterocycloalkyl group selected from:

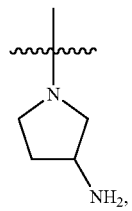 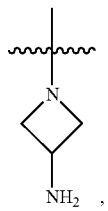 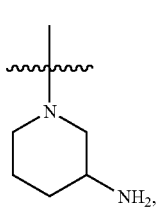

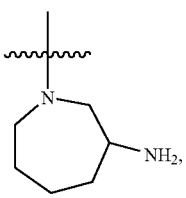 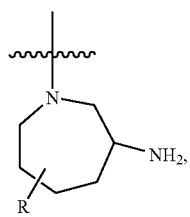

-continued

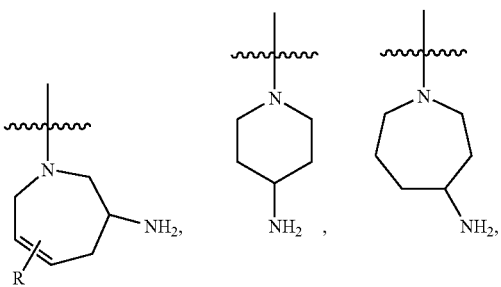

cis and trans

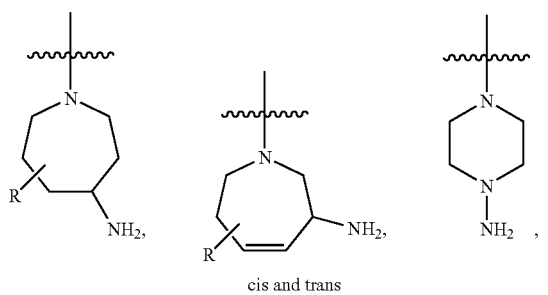

cis and trans

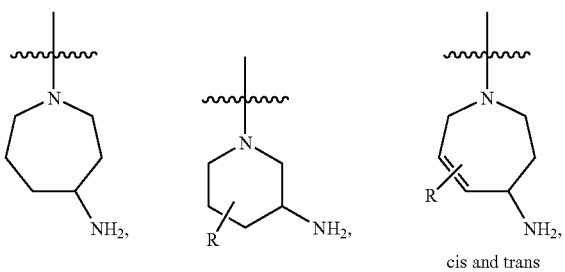

cis and trans

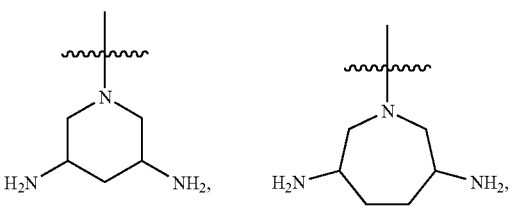

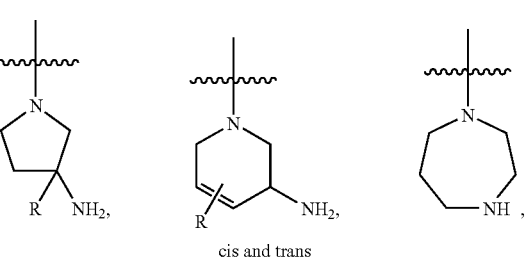

cis and trans

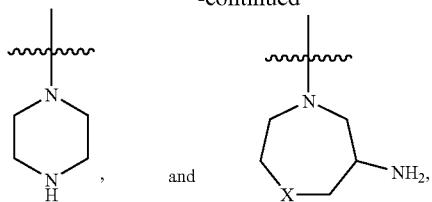

wherein:
each $NH_2$ group is optionally substituted with a $C_1$-$C_6$ alkyl group;
X is O, NR or $SO_2$, and
each R is independently selected from halogen, —OH, —$NH_2$, —SH, —S($C_1$-$C_6$ alkyl), —NH($C_1$-$C_6$ alkyl), —N($C_1$-$C_6$ alkyl)$_2$, $C_1$-$C_6$ alkyl, $C_1$-$C_6$ haloalkyl, and $C_1$-$C_6$ heteroalkyl.

In some embodiments, R is independently selected from hydrogen and $C_1$-$C_6$ alkyl.

In some embodiments, at least one $NH_2$ group is unsubstituted. In other embodiments, each $NH_2$ group is unsubstituted.

In some embodiments, $R_1$ and $R_2$, together with the nitrogen atom to which they are attached form a heterocycloalkyl group selected from:

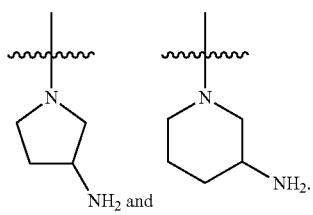

In some embodiments, Ar is a phenyl, pyridyl or pyrimidyl group. In some embodiments, Ar is a phenyl, pyridyl Or pyrimidyl group optionally substituted with one or two substituents independently selected from halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —$CO_2H$, or —$CO_2$($C_1$-$C_6$ alkyl). In some embodiments, Ar is a phenyl group optionally substituted with one or two substituents independently selected from halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —$CO_2H$, or —$CO_2$($C_1$-$C_6$ alkyl).

In some embodiments, $R_1$ is hydrogen, —$NH_2$, —OH, —SH, —N($C_1$-$C_3$ alkyl)$_2$, —NH($C_1$-$C_3$ alkyl), —$NCO_2$($C_1$-$C_3$ alkyl), —$NCO_2H$, —$NCONH_2$, In some embodiments, $R_2$ is hydrogen, halogen, or a group selected from phenyl, O-phenyl, and O—$CH_2$-phenyl, optionally substituted with halogen $C_1$-$C_6$ alkyl, —OH, —COOH, —COO($C_1$-$C_6$ alkyl). In some embodiments, $R_2$ is hydrogen.

In some embodiments, $R_4$ is a phenyl group optionally substituted with one or two groups independently selected from halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —$NHSO_2H$, —$NHSO_2$($C_1$-$C_6$ alkyl), —N($C_1$-$C_6$ alkyl)$SO_2H$, —N($C_1$-$C_6$ alkyl)$SO_2$($C_1$-$C_6$ alkyl), —$CONH_2$, —$CONH$($C_1$-$C_6$ alkyl), —$CON$($C_1$-$C_6$ alkyl)$_2$, and $SO_2$($C_1$-$C_6$ alkyl).

The compounds of Formula I (including without limitation any of the compounds specifically or generically described herein, including the compounds presented in the tables) may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. The compounds presented herein include racemic mixtures, in all ratios, of stereoisomeric, regioisomeric, diastereomeric, enantiomeric, and epimeric forms. Techniques for inverting or leaving unchanged a particular stereocenter, and those for resolving mixtures of stereoisomers, or racemic mixtures, are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The compounds of Formula I (including without limitation any of the compounds specifically or generically described herein, including the compounds presented in the tables) may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

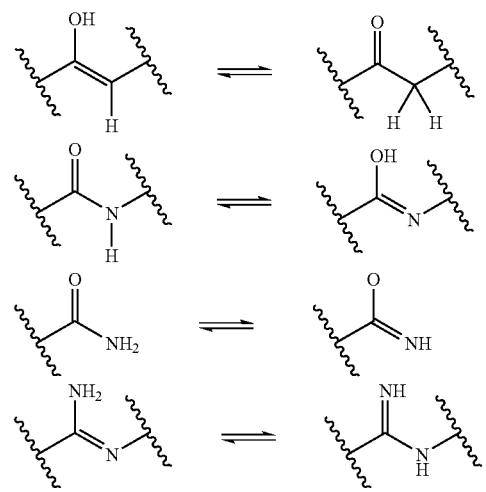

In some embodiments, the compounds of Formula I (including without limitation any of the compounds specifically or generically described herein, including the compounds presented in the tables) are useful as anti-fungal agents meaning that they kill and/or inhibit the growth of fungi. Thus, the compounds described herein may be used in medicine and are particularly useful as antifungal agents. The compounds described herein are thought to derive their activity from the inhibition of the synthesis of β-1,3-D-glucan. The compounds have advantages over the known glucan synthase inhibitors such as those belonging to the echinocandin family. For example, the existing inhibitors are modified natural products which are limited in their use by poor pharmacokinetic properties. In contrast the compounds described herein are inhibitors of β-1,3-glucan synthase, they are readily synthesised by standard chemistry, and they have more drug-like properties that are compatible with oral bioavailability. The compounds described herein are active against a wide range of fungi, particularly Candida such as Candida albicans and Aspergillus such as Aspergillus fumigatus.

In a second aspect is a compound according to the first aspect described herein for therapeutic use.

A third aspect described herein is a pharmaceutical composition comprising a compound according to the first aspect described herein and a pharmaceutically acceptable diluent or carrier.

A fourth aspect described herein is the use of a compound according to the first aspect described herein for the manufacture of a medicament for the treatment of a fungal infection.

In a fifth aspect is a method for the treatment of a fungal infection which comprises administering to a patient in need of such treatment an effective amount of a compound according to the first aspect described herein.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours;. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

Provided herein are methods for using a compound of Formula I, for the manufacture of a medicament for the treatment of a fungal infection. In some embodiments, the fungal infection is caused by a strain of Candida or Aspergillus.

Provided herein are pharmaceutical compositions comprising a compound of Formula I and a pharmaceutically acceptable diluent or carrier.

Provided herein are methods for treating a subject at risk of or suffering from a fungal infection, the method comprising administering to the subject a composition comprising a therapeutically effective amount of the compound of Formula I. In some embodiments, the compound of Formula I has an $IC_{50}$ of the compound for C. albicans growth is about 8 μM to about 55 μM. In some embodiments, the $IC_{50}$ of the compound for A. fumigatus growth is about 4 μM to about 93 μM. In some embodiments, the $IC_{50}$ of the compound for biosynthesis of glucan in C. albicans is about 3 μM to about 34 μM. In some embodiments, the $IC_{50}$ of the compound for biosynthesis of glucan in A. fumigatus is about 4 μM to about 93 μM.

Provided herein are methods of administering a therapeutically effective amount of a supplemental antifungal compound. In some embodiments, the supplemental antifungal compound is anidulafungin, caspofungin, micafungin, natamycin, rimocidin, nystatin, amphotericin B, miconazole, ketoconazole, clotrimazole, econazole, bifonazole, butoconazole, fenticonazole, isoconazole, oxiconazole, sertaconazole, sulconazole, tioconazole, triazole, fluconazole, itraconazole, isavuconazole ravuconazole, posaconazole, voriconazole, terconazole, terbinafine, amorolfine, naftifine, butenafine, ciclopirox olamine, 5-fluorocytosine, gentian violet, haloprogin, tolnaftate, or undecylenic acid.

In some embodiments, the compound and the supplemental antifungal compound are administered through separate routes of administration.

In some embodiments, the subject is diagnosed as suffering from blastomycosis, tinea, coccidiomycosis, cryptococcosis, candidiasis, moniliasis, dermatomycosis, dermatophytosis, favus, keratomycosis, phycomycosis, sporotrichosis, or rhinosporidiosis.

In some embodiments, subject is immunocompromised. In some embodiments, the subject is suffering from AIDS, cancer, severe combined immunodeficiency, tuberculosis, diabetes, intravenous drug abuse, or severe burns. In some embodiments, the subject is undergoing immunosuppressive therapy.

In some embodiments, the subject is exposed to a chronic antibiotic, chronic corticosteroid treatment, undergoes prolonged use of an intravenous catheter, or undergoes prolonged use of a urinary catheter.

In some embodiments, the methods comprise further administering to the subject a composition comprising a therapeutically effective amount of an immunosuppressive agent. In some embodiments, the methods comprise further administering a chemotherapy agent. In some embodiments, the methods comprise further administering an anti-inflammatory agent. In some embodiments, the methods comprise further administering a bacterial antibiotic compound. In some embodiments, the methods comprise further administering an anti-HIV compound. In some embodiments, the methods comprise further administering an anti-diabetic agent.

In some embodiments, the administration is oral, topical, transdermal, intravenous, subcutaneous, intracutaneous, intramuscular, intranasal, rectal, vaginal, buccal, or sublingual. In some embodiments, the composition is administered as a cream, ointment, paste, gel, spray, or a liposomal preparation.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features described herein are set forth with particularity in the appended claims. A better understanding of the features and advantages of the present invention will be obtained by reference to the following detailed description that sets forth illustrative embodiments, in which the principles described herein are utilized, and the accompanying drawings of which:

DETAILED DESCRIPTION OF THE INVENTION

Figure 1:
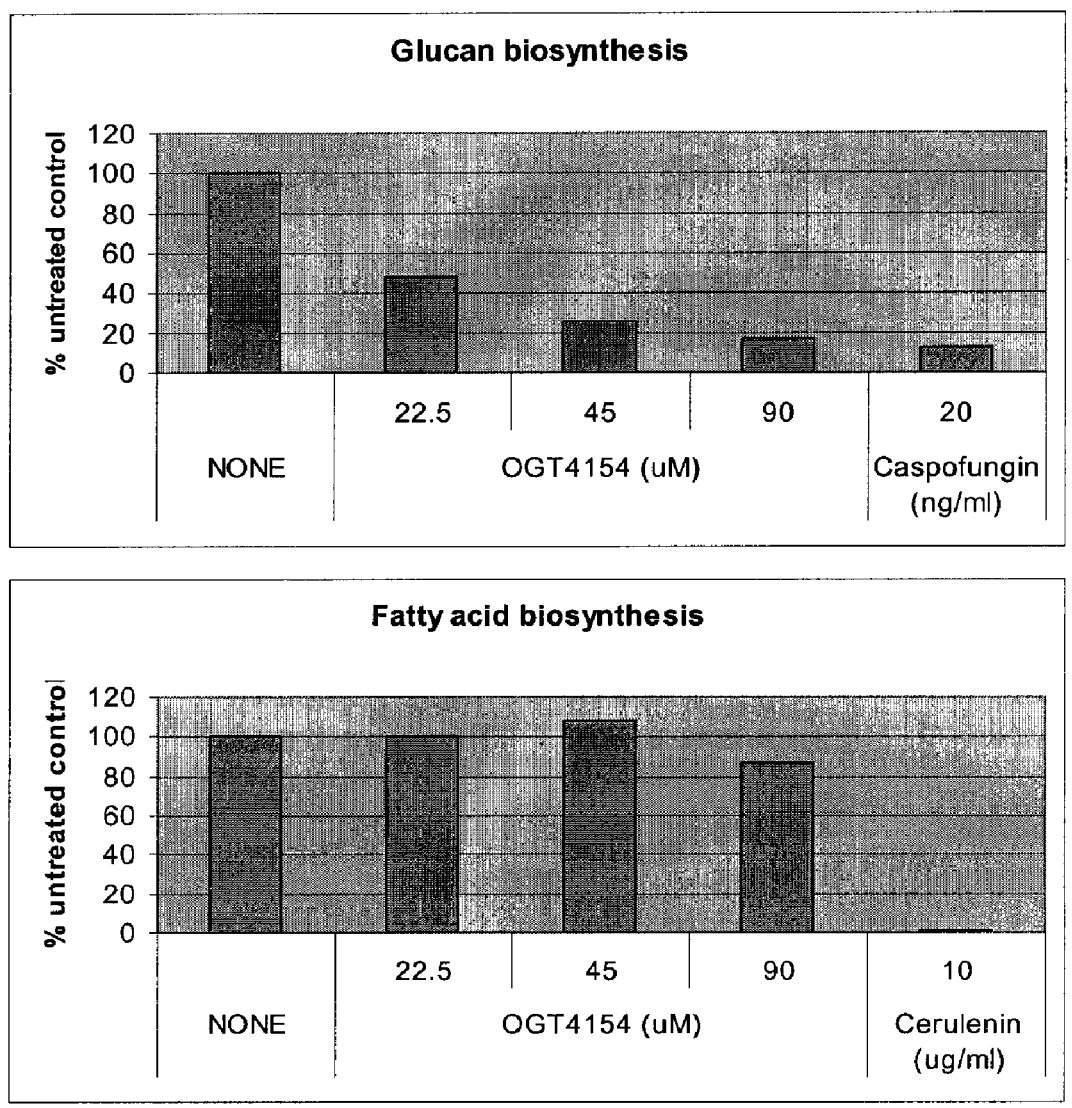
FIG. 1 shows the inhibition of glucose incorporation into β-1,3-D-glucan in *Candida Albicans* strain CAF2-1. OGT4154 preferentially inhibits β-1,3-D-glucan biosynthesis in *Candida Albicans*.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

In some embodiments, the compounds of Formula I (including without limitation any of the compounds specifically or generically described herein, including the compounds presented in the tables) are useful as anti-fungal agents meaning that they kill and/or inhibit the growth of fungi. Thus, the compounds described herein may be used in medicine and are particularly useful as antifungal agents. The compounds described herein are thought to derive their activity from the inhibition of the synthesis of β-1,3-D-glucan. The compounds have advantages over the known glucan synthase inhibitors such as those belonging to the echinocandin family. For example, the existing inhibitors are modified natural products which are limited in their use by poor pharmacokinetic properties. In contrast the compounds described herein are inhibitors of β-1,3-glucan synthase, they are readily synthesised by standard chemistry, and they have more drug-like properties that are compatible with oral bioavailability. The compounds described herein are active against a wide range of fungi, particularly *Candida* such as *Candida albicans* and *Aspergillus* such as *Aspergillus fumigatus*.

Where substituent groups are specified by their conventional chemical formulas, written from left to right, they equally encompass the chemically identical substituents that would result from writing the structure from right to left. As a non-limiting example, —$CH_2O$— is equivalent to —$OCH_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

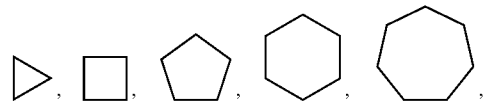

-continued

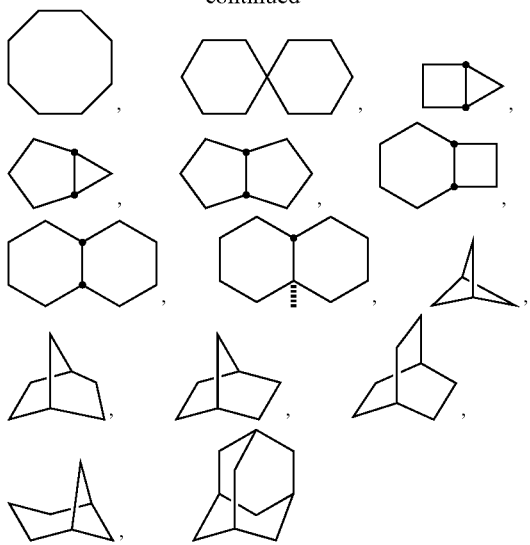

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. A fused cycloalkenyl may contain from two to four fused rings where the ring of attachment is a cycloalkenyl ring, and the other individual rings may be alicyclic, heterocyclic, aromatic, heteroaromatic or any combination thereof. Fused ring systems may be fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

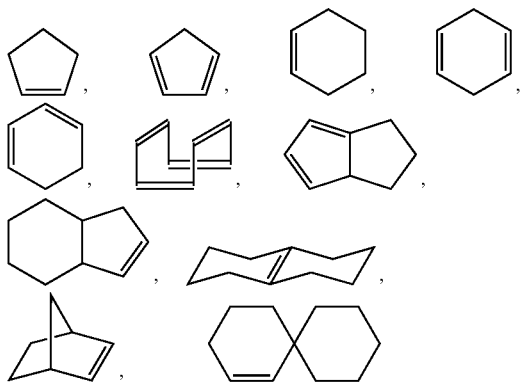

and the like.

The term "heterocycloalkyl" as used herein, alone or in combination, refer to optionally substituted, saturated, partially unsaturated or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. The terms also include all ring forms of the carbohydrates, including but not limited to the monosaccharides, the disaccharides and the oligosaccharides. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

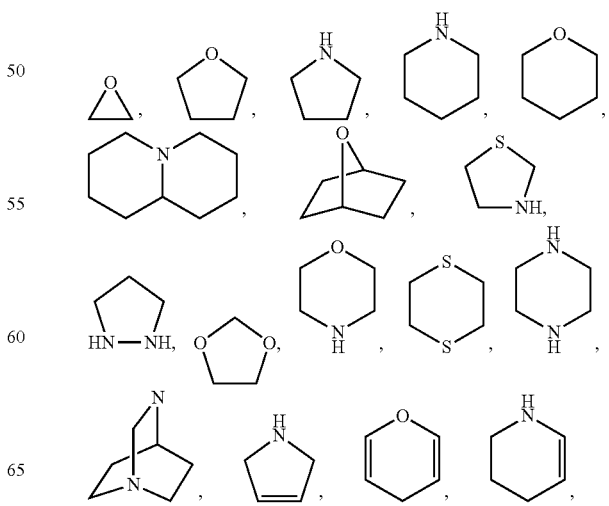

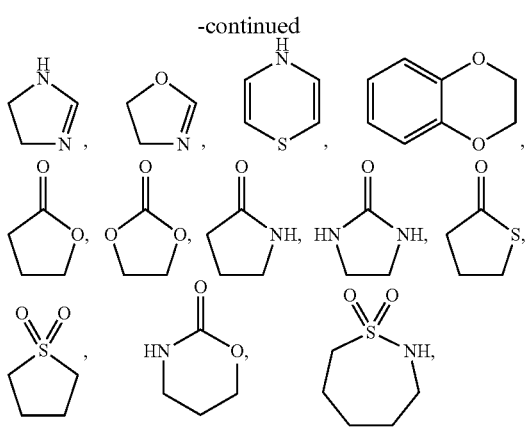

and the like.

The term "aromatic" as used herein, refers to a planar, cyclic or polycyclic, ring moiety having a delocalized π-electron system containing 4n+2π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

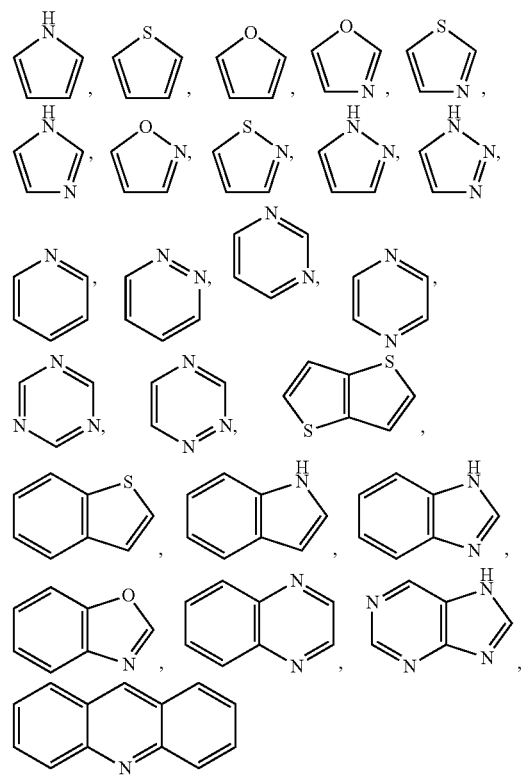

and the like.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "nitro" as used herein, alone or in combination, refers to the monoradical —NO$_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

Certain Pharmaceutical Terminology

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Where combination treatments are contemplated, it is not intended that the compounds described herein be limited by the particular nature of the combination. For example, the compounds described herein may be administered in combination as simple mixtures as well as a chemical hybrids. An example of the latter is where the compound is covalently linked to a targeting carrier or to an active pharmaceutical. Covalent binding can be accomplished in many ways, such as, though not limited to, the use of a commercially available cross-linking compound.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

As used herein, the terms "co-administration", "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "carrier" as used herein, refers to relatively non-toxic chemical compounds or agents that facilitate the incorporation of a compound into cells or tissues.

The term "pharmaceutically acceptable derivative or prodrug" as used herein, refers to any pharmaceutically acceptable salt, ester, salt of an ester or other derivative of a compound of Formula I, which, upon administration to a recipient, is capable of providing, either directly or indirectly, a compound described herein or a pharmaceutically active metabolite or residue thereof. Particularly favored derivatives or prodrugs are those that increase the bioavailability of the compounds described herein when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds described herein, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds described herein and their pharmaceutically acceptable acid addition salts. (See for example Berge et al., *J. Pharm. Sci.* 1977, 66, 1-19.) Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4} alkyl)_4OH^-$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics,* 9th Edition, McGraw-Hill (1996).

Compounds

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

Described herein are compounds of Formula I:

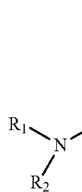

(Formula I)

wherein:
n is 0, 1, or 2;
$R_1$ and $R_2$ are independently selected from H, ($C_1$-$C_6$) alkyl, ($C_1$-$C_6$)alkenyl, ($C_1$-$C_6$)alkynyl, ($C_1$-$C_6$)heteroalkyl, ($C_1$-$C_6$)heteroalkenyl, ($C_3$-$C_8$)cycloalkyl, ($C_3$-$C_8$)cycloalkenyl, ($C_3$-$C_8$)heterocycloalkyl, ($C_3$-$C_8$) heterocycloalkenyl, aryl, and heteroaryl, any of which is optionally substituted with 1 or 2 independently selected $R_x$ groups;
or $R_1$ and $R_2$ together with the nitrogen atom to which they are attached form a 4- to 8-membered heterocycloalkyl or heterocycloalkenyl group, any of which is optionally substituted with 1 or 2 independently selected $R_x$ groups;
Ar is selected from phenyl, naphthyl, and a monocylic or bicyclic heteroaryl group, any of which is optionally substituted with 1 or 2 independently selected $R_x$ groups, or with a phenyl, O-phenyl, or $OCH_2$-phenyl in which the phenyl group is further optionally substituted with 1 or 2 independently selected $R_x$ groups;
$R_3$ is $L_1$-$L_2$-$R_4$, where $L_1$ is selected from a bond, O, $NR_1$, and S; $L_2$ is selected from a bond, ($C_1$-$C_6$)alkyl, ($C_1$-$C_6$) alkenyl, ($C_1$-$C_6$)alkynyl, ($C_1$-$C_6$)heteroalkyl, ($C_1$-$C_6$) heteroalkenyl, ($C_3$-$C_8$)cycloalkyl, ($C_3$-$C_8$)cycloalkenyl, ($C_3$-$C_8$)heterocycloalkyl, and ($C_3$-$C_8$)heterocycloalkenyl; and $R_4$ is selected from H, cycloalkyl, cycloalkenyl, heterocycloalkyl, heterocycloalkenyl, aryl, and heteroaryl, any of which is optionally substituted with 1 or 2 independently selected $R_x$ groups
$R_x$ is be $L_{s1}L_{s2}R_s$, wherein each $L_{s1}$ and $L_{s2}$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, ($C_1$-$C_6$)alkyl, and —($C_2$-$C_6$)alkenyl; and $R_s$ is selected from hydrogen, alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, isocyanato, thiocyanato, isothiocyanato, nitro, perhaloalkyl, perfluoroalkyl, silyl, and amino, including mono- and di-substituted amino groups, and the protected derivatives thereof;
or a pharmaceutically acceptable salt, prodrug, solvate, polymorph, tautomer, or isomer thereof.

In some embodiments, n is 0; in other embodiments, n is 1. In further embodiments, $R_1$ and $R_2$ together with the nitrogen atom to which they are attached form a 4- to 8-membered heterocycloalkyl or heterocycloalkenyl group, any of which is optionally substituted with 1 or 2 independently selected $R_x$ groups. In still further embodiments, $R_1$ and $R_2$ together with the nitrogen atom to which they are attached form a 4- to 8-membered heterocycloalkyl. In yet further embodiments, the heterocycloalkyl group is a 5-membered heterocycloalkyl. In alternative embodiments, the heterocycloalkyl group is a 6-membered heterocycloalkyl. In further embodiments, the heterocycloalkyl group contains a single N atom, whereas in alternative embodiments, the heterocycloalkyl group contains two N atoms. In further embodiments, the heterocycloalkyl group, is unsubstituted. In alternative embodiments, the heterocycloalkyl group is substituted with one $R_x$ group. In still further embodiments, $R_x$ is $L_{s1}L_{s2}R_s$, wherein each $L_{s1}$ and $L_{s2}$ is independently selected from a bond, —O—, —C(=O)—, —NH—, —NHC(O)—, —C(O)NH—, —OC(O)NH—, —NHC(O)O—, ($C_1$-$C_6$) alkyl, and —($C_2$-$C_6$)alkenyl. In a further embodiment, $R_s$ is selected from hydrogen, alkyl, cycloalkyl, aryl, heteroaryl, heteroalicyclic, hydroxy, alkoxy, aryloxy, carbonyl, perhaloalkyl, perfluoroalkyl, and amino, including mono- and di-substituted amino groups.

In further or alternative embodiments of any of the aforementioned embodiments, Ar is selected from a phenyl, pyridyl, or pyrimidyl group. In further embodiments, Ar is a phenyl group. In further embodiments, Ar is substituted with a phenyl, O-phenyl, or $OCH_2$-phenyl in which the phenyl group is further optionally substituted with 1 or 2 independently selected $R_x$ groups. In still further embodiments, $R_x$ is $L_{s1}L_{s2}R_s$, wherein each $L_{s1}$ and $L_{s2}$ is independently selected from a bond, —O—, —C(=O)—, —NH—, —NHC(O)—, —C(O)NH—, —OC(O)NH—, —NHC(O)O—, ($C_1$-$C_6$) alkyl, and —($C_2$-$C_6$)alkenyl. In a further embodiment, $R_s$ is selected from hydrogen, alkyl, cycloalkyl, aryl, heteroaryl, heteroalicyclic, hydroxy, alkoxy, aryloxy, carbonyl, perhaloalkyl, perfluoroalkyl, and amino, including mono- and di-substituted amino groups. In an alternative embodiment, Ar is subsituted with one or two $R_x$ groups. In still further embodiments, $R_x$ is $L_{s1}L_{s2}R_s$, wherein each $L_{s1}$ and $L_{s2}$ is independently selected from a bond, —O—, —C(=O)—, —NH—, —NHC(O)—, —C(O)NH—, —OC(O)NH—, —NHC(O) O—, ($C_1$-$C_6$)alkyl, and —($C_2$-$C_6$)alkenyl. In a further embodiment, $R_s$ is selected from hydrogen, alkyl, cycloalkyl, aryl, heteroaryl, heteroalicyclic, hydroxy, alkoxy, aryloxy, carbonyl, perhaloalkyl, perfluoroalkyl, and amino, including mono- and di-substituted amino groups.

In further or alternative embodiments of any of the aforementioned embodiments, $R_3$ is $L_1$-$L_2$-$R_4$, where $L_1$ is selected from a bond, O, and $NR_1$. In further embodiments, $L_2$ is selected from a bond, ($C_1$-$C_6$)alkyl, ($C_1$-$C_6$)alkenyl, ($C_1$-$C_6$)heteroalkyl, ($C_3$-$C_8$)cycloalkyl, and ($C_3$-$C_8$)heterocycloalkyl. In further embodiments, $L_2$ is selected from ($C_1$-$C_6$) alkyl and ($C_1$-$C_6$)alkenyl. In alternative embodiments, $L_2$ is selected from a bond. In alternative embodiments, $L_2$ is selected from ($C_1$-$C_6$)alkyl. In alternative embodiments, $L_2$ is selected from ($C_1$-$C_6$)alkenyl. In further embodiments, $R_4$ is selected from H, aryl, and heteroaryl. In further embodiments, $R_4$ is H. In alternative embodiments, $R_4$ is aryl. In alternative embodiments, $R_4$ is heteroaryl. In an alternative embodiment, $R_4$ is a phenyl, subsituted with one or two $R_x$ groups. In still further embodiments, $R_x$ is $L_{s1}L_{s2}R_s$, wherein each $L_{s1}$ and $L_{s2}$ is independently selected from a bond, —O—, —C(=O)—, —NH—, —NHC(O)—, —C(O) NH—, OC(O)NH—, —NHC(O)O—, ($C_1$-$C_6$)alkyl, and —($C_2$-$C_6$)alkenyl. In a further embodiment, $R_s$ is selected from hydrogen, alkyl, cycloalkyl, aryl, heteroaryl, heteroalicyclic, hydroxy, alkoxy, aryloxy, carbonyl, perhaloalkyl, perfluoroalkyl, and amino, including mono- and di-substituted amino groups. In an alternative embodiment, $R_4$ is an unsubstituted phenyl.

Provided herein are compounds or pharmaceutically acceptable salts of Formula II:

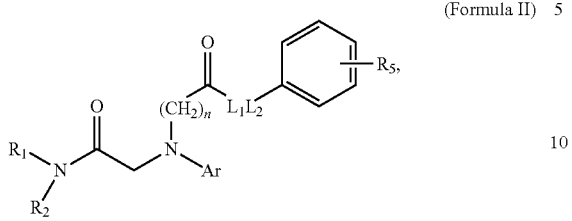

(Formula II)

wherein:

n is 0 or 1, $R_5$ is selected from halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —$NHSO_2H$, —$NHSO_2$($C_1$-$C_6$ alkyl), —N($C_1$-$C_6$ alkyl)$SO_2H$, —N($C_1$-$C_6$ alkyl)$SO_2$($C_1$-$C_6$ alkyl), —$CONH_2$, —CONH($C_1$-$C_6$ alkyl), —CON($C_1$-$C_6$ alkyl)$_2$, and $SO_2$($C_1$-$C_6$ alkyl), or a pharmaceutically acceptable salt, prodrug, solvate, polymorph, tautomer, or isomer thereof.

Provided herein are compounds or pharmaceutically acceptable salts of Formula III:

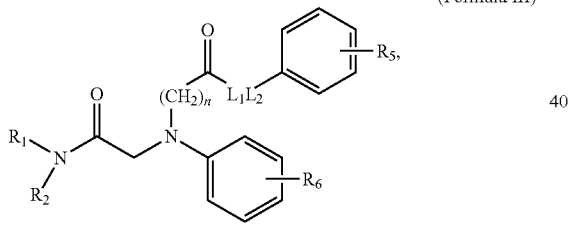

(Formula III)

wherein:

n is 0 or 1;

$R_5$ is selected from hydrogen, halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —$NHSO_2H$, —$NHSO_2$($C_1$-$C_6$ alkyl), —N($C_1$-$C_6$ alkyl)$SO_2H$, —N($C_1$-$C_6$ alkyl)$SO_2$($C_1$-$C_6$ alkyl), —$CONH_2$, —CONH($C_1$-$C_6$ alkyl), —CON($C_1$-$C_6$ alkyl)$_2$, and $SO_2$($C_1$-$C_6$ alkyl); and $R_6$ is selected from hydrogen, halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —$CO_2H$, or —$CO_2$($C_1$-$C_6$ alkyl), or a pharmaceutically acceptable salt, prodrug, solvate, polymorph, tautomer, or isomer thereof.

Provided herein are compounds or pharmaceutically acceptable salts of Formula IV or Formula V:

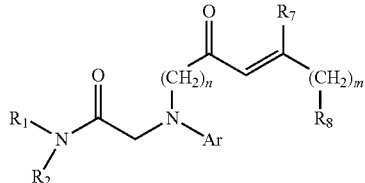

Formula IV

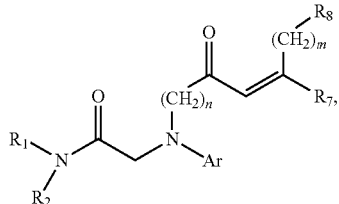

Formula V wherein:

$R_7$ is hydrogen, halogen, or $C_1$-$C_6$ alkyl; and $R_8$ is a phenyl group optionally substituted with one or two groups independently selected from halogen, $C_1$-$C_6$ alkyl, hydroxy, —O($C_1$-$C_6$ alkyl), —$NH_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —$NHSO_2H$, —$NHSO_2$($C_1$-$C_6$ alkyl), —N($C_1$-$C_6$ alkyl)$SO_2H$, —N($C_1$-$C_6$ alkyl)$SO_2$($C_1$-$C_6$ alkyl), —$CONH_2$, —CONH($C_1$-$C_6$ alkyl), —CON($C_1$-$C_6$ alkyl)$_2$, and $SO_2$($C_1$-$C_6$ alkyl), or a pharmaceutically acceptable salt, prodrug, solvate, polymorph, tautomer, or isomer thereof.

Provided herein are compounds or pharmaceutically acceptable salts of Formula VI or Formula VII:

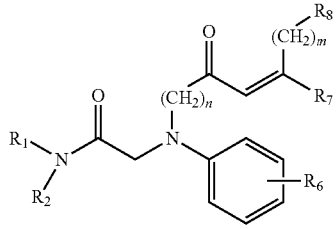

Formula VI

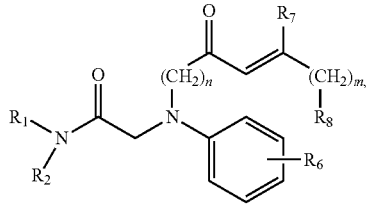

Formula VII wherein:

$R_6$ is selected from hydrogen, halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —$CO_2H$, or —$CO_2$($C_1$-$C_6$ alkyl);

$R_7$ is hydrogen, halogen, or $C_1$-$C_6$ alkyl; and

R₈ is a phenyl group optionally substituted with one or two groups independently selected from halogen, $C_1$-$C_6$ alkyl, hydroxy, —O($C_1$-$C_6$ alkyl), —NH$_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —NHSO$_2$H, —NHSO$_2$($C_1$-$C_6$ alkyl), —N($C_1$-$C_6$ alkyl)SO$_2$H, —N($C_1$-$C_6$ alkyl)SO$_2$($C_1$-$C_6$ alkyl), —CONH$_2$, —CONH($C_1$-$C_6$ alkyl), —CON($C_1$-$C_6$ alkyl)$_2$, and SO$_2$($C_1$-$C_6$ alkyl), or a pharmaceutically acceptable salt, prodrug, solvate, polymorph, tautomer, or isomer thereof.

In some embodiments, $R_1$ and $R_2$, together with the nitrogen atom to which they are attached form a heterocycloalkyl group selected from:

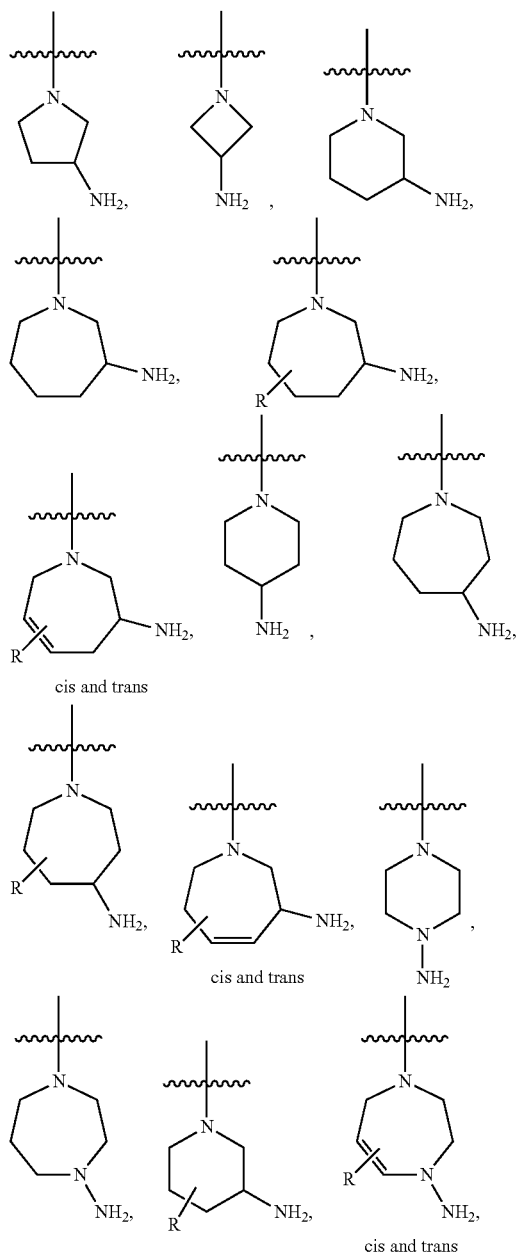

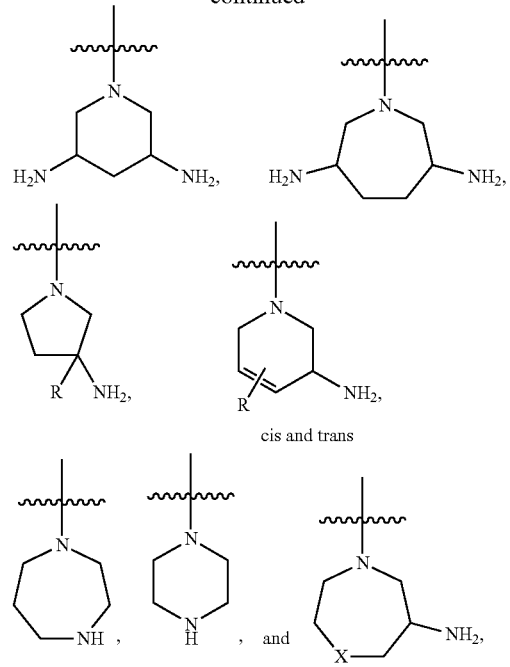

wherein:
each NH$_2$ group is optionally substituted with a $C_1$-$C_6$ alkyl group;
X is O, NR or SO$_2$, and
each R is independently selected from halogen, —OH, —NH$_2$, —SH, —S($C_1$-$C_6$ alkyl), —NH($C_1$-$C_6$ alkyl), —N($C_1$-$C_6$ alkyl)$_2$, $C_1$-$C_6$ alkyl, $C_1$-$C_6$ haloalkyl, and $C_1$-$C_6$ heteroalkyl.

In some embodiments, R is independently selected from hydrogen and $C_1$-$C_6$ alkyl.

In some embodiments, each NH$_2$ group is unsubstituted.

In some embodiments, $R_1$ and $R_2$, together with the nitrogen atom to which they are attached form a heterocycloalkyl group selected from:

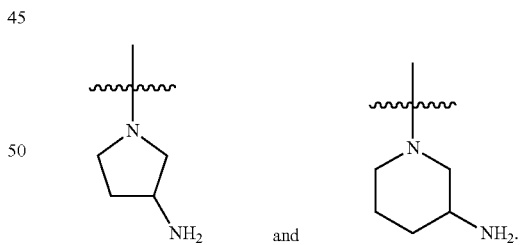

In some embodiments, Ar is a phenyl, pyridyl or pyrimidyl group. In some embodiments, Ar is a phenyl, pyridyl or pyrimidyl group optionally substituted with one or two substituents independently selected from halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —CO$_2$H, or —CO$_2$($C_1$-$C_6$ alkyl). In some embodiments, Ar is a phenyl group optionally substituted with one or two substituents independently selected from halogen and a $C_1$-$C_6$ alkyl, phenyl, —O-phenyl, or —O-benzyl group optionally substituted with halogen, $C_1$-$C_6$ alkyl, hydroxy, —O($C_1$-$C_6$ alkyl), —CO$_2$H, or —CO$_2$($C_1$-$C_6$ alkyl).

In some embodiments, $R_1$ is hydrogen, —$NH_2$, —OH, —SH, —$N(C_1$-$C_3$ alkyl$)_2$, —$NH(C_1$-$C_3$ alkyl), —$NCO_2(C_1$-$C_3$ alkyl), —$NCO_2H$, —$NCONH_2$, In some embodiments, $R_2$ is hydrogen, halogen, or a group selected from phenyl, O-phenyl, and O—$CH_2$-phenyl, optionally substituted with halogen $C_1$-$C_6$ alkyl, —OH, —COOH, —COO($C_1$-$C_6$ alkyl). In some embodiments, $R_2$ is hydrogen. In some embodiments, $R_4$ is a phenyl group optionally substituted with one or two groups independently selected from halogen, $C_1$-$C_6$ alkyl, hydroxy, —O($C_1$-$C_6$ alkyl), —$NH_2$, —$NH(C_1$-$C_6$ alkyl), —$N(C_1$-$C_6$ alkyl)($C_1$-$C_6$ alkyl), —($C_1$-$C_6$ haloalkyl), —NHCOH In some embodiments, the compound of Formula I, or a pharmaceutically acceptable salt thereof, is:

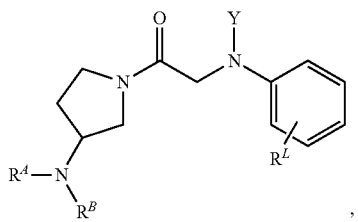

wherein:

Y is selected from the group consisting of —$CH_2CO_2R^E$, —$CH_2CONHR^J$ and —COZ;

Z is selected from the group consisting of Ph, —$C_{1-3}$alkylPh and —CH=CHPh, wherein Ph is substituted with $R^C$ and $R^D$ which are independently selected from the group comprising hydrogen, halogen, $C_1$-$C_6$ alkyl, $OR^E$, $NR^GR^H$, $NR^GCOR^W$, $NR^GSO_2R^W$, $CONR^GR^H$ and $SO_2R^W$;

$R^L$ is selected from the group consisting of hydrogen, halogen, Ph, OPh and $OCH_2Ph$, wherein Ph is optionally substituted with halogen, $C_1$-$C_6$ alkyl, $OR^E$ or $CO_2R^E$;

$R^A$ and $R^B$ are independently selected from hydrogen, $C_1$-$C_6$ alkyl and $CO_2R^F$;

$R^E$ is hydrogen or $C_1$-$C_6$ alkyl;

$R^F$ is $C_1$-$C_6$ alkyl;

$R^G$ and $R^H$ are independently hydrogen or $C_1$-$C_6$ alkyl or may together form a 5- or 6-membered ring which optionally contains one further heteroatom selected from $NR^E$, S and O;

$R^W$ is $C_1$-$C_6$ alkyl; and $R^J$ is $CH_2Ph$, $(CH_2)_2Ph$ or $(CH_2)_2OPh$, wherein Ph is substituted with $R^C$ and $R^D$.

In some embodiments, Y is $CH_2CONHCH_2Ph$ where the Ph is substituted with $R^C$ and $R^D$, wherein $R^C$ and $R^D$ are as defined above.

In other embodiments, Y is —COCH=CHPh where the phenyl group is substituted with $R^C$ and $R^D$, wherein $R^C$ and $R^D$ are as defined above.

In some embodiments, Y is COZ and $R^L$ is Ph or OPh, wherein Ph is optionally substituted with halogen, $C_1$-$C_6$ alkyl, $OR^E$ or $CO_2R^E$, and wherein $R^E$ and Z are as defined above.

In some embodiments, Y is —$CH_2CO_2R^E$ or —$CH_2CONHR^J$, and $R^L$ is OPh or $OCH_2Ph$, wherein Ph is optionally substituted with halogen or $C_1$-$C_6$ alkyl, and wherein $R^E$ and $R^J$ are as defined in claim 1.

In some embodiments, $R^C$ and $R^D$ are independently selected from the group comprising hydrogen, halogen and $C_1$-$C_6$ alkyl.

In some embodiments, $R^A$ is hydrogen or $C_1$-$C_6$ alkyl.

In some embodiments, $R^B$ is hydrogen or $C_1$-$C_6$ alkyl.

In some embodiments, the compound of Formula I, or a pharmaceutically acceptable salt thereof, is:

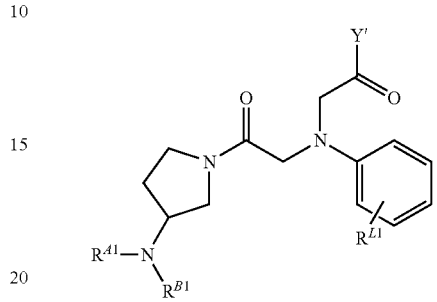

wherein

Y' is selected from the group comprising $OR^{C1}$ and $NHR^{D1}$;

$R^{L1}$ is selected from the group consisting of hydrogen, halogen, Ph, OPh and $OCH_2Ph$, wherein Ph is optionally substituted with halogen, $C_1$-$C_6$ alkyl, $OR^{C1}$ or $CO_2R^{C1}$;

$R^{A1}$ and $R^{B1}$ are independently selected from hydrogen, $C_1$-$C_6$ alkyl and $CO_2R^{W1}$;

$R^{C1}$ is hydrogen or $C_1$-$C_6$ alkyl;

$R^{D1}$ is $CH_2Ph$, $(CH_2)_2Ph$ or $(CH_2)_2OPh$, wherein Ph is substituted with $R^{E1}$ and $R^{F1}$;

$R^{E1}$ and $R^{F1}$ are independently selected from the group comprising hydrogen, halogen, $C_1$-$C_6$ alkyl, $OR^{C1}$, $NR^{G1}R^{H1}$, $NR^{G1}COR^{W1}$, $NR^{G1}SO_2R^{W1}$, $CONR^{G1}R^{H1}$ or $SO_2R^{W1}$;

$R^{G1}$ and $R^{H1}$ are independently hydrogen or $C_1$-$C_6$ alkyl or may together form a 5- or 6-membered ring which optionally contains one further heteroatom selected from $NR^{C1}$, S and O; and $R^{W1}$ is $C_1$-$C_6$ alkyl.

In some embodiments, Y' is $NHCH_2Ph$ where the Ph is substituted with $R^{E1}$ and $R^{F1}$, wherein $R^{E1}$ and $R^{F1}$ are as defined above.

In some embodiments, $R^{E1}$ and $R^{F1}$ are independently selected from the group comprising hydrogen, halogen and $C_1$-$C_6$ alkyl.

In some embodiments, $R^{A1}$ is hydrogen or $C_1$-$C_6$ alkyl.

In some embodiments, $R^{B1}$ is hydrogen or $C_1$-$C_6$ alkyl.

In some embodiments, $R^{L1}$ is OPh or $OCH_2Ph$, wherein Ph is unsubstituted or is substituted with halogen or $C_1$-$C_6$ alkyl.

According to a further embodiment described herein, Y' is $CH_2CONHCH_2Ph$ where the phenyl group is substituted with $R^{C1}$ and $R^{D1}$ as defined above, including in the meta or para position. Suitably, $R^{C1}$ and $R^{D1}$ are independently selected from the group comprising hydrogen, halogen and $C_1$-$C_6$ alkyl. Particular values of $R^{C1}$ and $R^{D1}$ include hydrogen, fluoro, chloro and trifluoromethyl. In one embodiment $R^{A1}$ and $R^{B1}$ are both hydrogen. In one embodiment $R^{L1}$ is OPh or $OCH_2Ph$, including in the meta or para position, wherein Ph is optionally substituted with halogen or $C_1$-$C_6$ alkyl but is preferably unsubstituted.

In some embodiments, the compound of Formula I, or a pharmaceutically acceptable salt thereof, is:

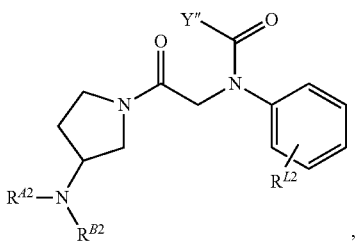

wherein

Y" is selected from the group comprising Ph, —$C_{1-3}$alkylPh and —CH=CHPh, wherein Ph is substituted with $R^{C2}$ and $R^{D2}$ which are independently selected from the group comprising hydrogen, halogen, $C_1$-$C_6$ alkyl, $OR^{E2}$, $NR^{G2}R^{H2}$, $NR^{G2}COR^{W2}$, $NR^{G2}SO_2R^{W2}$, $CONR^{G2}R^{H2}$ and $SO_2R^{W2}$;

$R^{L2}$ is selected from the group consisting of hydrogen, halogen, Ph, OPh and $OCH_2Ph$, wherein Ph is optionally substituted with halogen, $C_1$-$C_6$ alkyl, $OR^{E2}$ or $CO_2R^{E2}$;

$R^{A2}$ and $R^{B2}$ are independently selected from hydrogen, $C_1$-$C_6$ alkyl and $CO_2R^{F2}$;

$R^{E2}$ is hydrogen or $C_1$-$C_6$ alkyl;

$R^{F2}$ is $C_1$-$C_6$ alkyl;

$R^{G2}$ and $R^{H2}$ are independently hydrogen or $C_1$-$C_6$ alkyl or may together form a 5- or 6-membered ring which optionally contains one further heteroatom selected from $NR^{E2}$, S and O; and $R^{W2}$ is $C_1$-$C_6$ alkyl.

In some embodiments, Y" is —CH=CHPh where the phenyl group is substituted with $R^{C2}$ and $R^{D2}$, wherein $R^{C2}$ $R^{D2}$ are as defined above.

In some embodiments, $R^{C2}$ and $R^{D2}$ are independently selected from the group comprising hydrogen, halogen and $C_1$-$C_6$ alkyl.

In some embodiments, $R^{A2}$ is hydrogen or $C_1$-$C_6$ alkyl.

In some embodiments, $R^{B2}$ is hydrogen or $C_1$-$C_6$ alkyl.

In some embodiments, $R^{L2}$ is Ph or OPh, wherein Ph is optionally substituted with halogen, $C_1$-$C_6$ alkyl, $OR^{E2}$ or $CO_2R^{E2}$.

According to one embodiment described herein, Y" is —COCH=CHPh where the phenyl group is substituted with $R^{C2}$ and $R^{D2}$ as defined above, including in the meta or para position. Suitably, $R^{C2}$ and $R^{D2}$ are independently selected from the group comprising hydrogen, halogen and $C_1$-$C_6$ alkyl. Typically, $R^{C2}$ and $R^{D2}$ are both hydrogen. In one embodiment $R^{A2}$ and $R^{B2}$ are both hydrogen. Preferably $R^{L2}$ is Ph or OPh, including in the meta or para position, wherein Ph is optionally substituted with halogen, $C_1$-$C_6$ alkyl, $OR^{E2}$ or $CO_2R^{E2}$, especially $OR^{E2}$ or $CO_2R^{E2}$.

Compounds described herein that have been shown to work well are OGT4325, OGT4355, OGT4344, OGT4420, OGT4421, OGT4165, OGT4154, OGT4155 and OGT3935.

(E)-N-[2-((S)-3-Amino-pyrrolidin-1-yl)-2-oxo-ethyl]-3-phenyl-N-(3'-trifluoromethoxy-biphenyl-4-yl)-acrylamide (OGT4325)

4'-{[2-((S)-3-Amino-pyrrolidin-1-yl)-2-oxo-ethyl]-[(E)-(3-phenylacryloyl)]-amino}-biphenyl-3-carboxylic acid, ethyl ester (OGT4355)

(E)-N-[2-((S)-3-Aminopyrrolidin-1-yl)-2-oxo-ethyl]-N-(4-phenoxyphenyl)-3-phenylacrylamide (OGT4344)

(E)-N-[2-((S)-3-Aminopyrrolidin-1-yl)-2-oxo-ethyl]-N-[4-(4-trifluoromethoxy-benzyloxy)phenyl]-3-phenylacrylamide (OGT4420)

(E)-N-[2-((S)-3-Aminopyrrolidin-1-yl)-2-oxo-ethyl]-N-[4-(3,4-dichloro-benzyloxy)phenyl]-3-phenylacrylamide (OGT4421)

2-[[2-((S)-3-Aminopyrrolidin-1-yl)-2-oxo-ethyl]-(3-phenoxyphenyl)amino]-N-[3,5-bis-(trifluoromethyl)benzyl]acetamide (OGT4165)

2-[[2-((S)-3-Aminopyrrolidin-1-yl)-2-oxo-ethyl]-(4-phenoxyphenyl)amino]-N-(3-chlorobenzyl)acetamide (OGT4154)

2-[[2-((S)-3-Aminopyrrolidin-1-yl)-2-oxo-ethyl]-(4-phenoxyphenyl)amino]-N-[3-fluoro-5-(trifluoromethyl)benzyl]acetamide (OGT4155)

2-[[2-((S)-3-Aminopyrrolidin-1-yl)-2-oxo-ethyl]-(2-phenoxyphenyl)amino]-N-(3-chlorobenzyl)acetamide (OGT3935)

Synthetic Procedures

In another aspect, methods for synthesizing the compounds of Formula I (including without limitation any of the compounds specifically or generically described herein) are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting materials used for the synthesis of the compounds of Formula I (including without limitation any of the compounds specifically or generically described herein) can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

Examples of Covalent Linkages and Precursors Thereof

| Covalent Linkage Product | Electrophile | Nucleophile |
|---|---|---|
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Aziridines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Use of Protecting Groups

During the synthesis of the compounds of Formula I, labile functional groups in the intermediate compounds may be protected. For example, it may be necessary to protect reactive functional groups, for example hydroxy, amino, imino, thio or carboxy groups, where these are desired in the final product, to avoid their unwanted participation in the reactions. The protecting groups may be removed at any stage in the synthesis of the compounds of Formula I or may be present on the final compound of Formula I. A comprehensive discussion of the ways in which various labile functional groups may be protected and methods for cleaving the resulting protected derivatives is given in for example *Protective Groups in Organic Chemistry*, T. W. Greene and P. G. M. Wuts (Wiley-Interscience, New York, $2^{nd}$ edition, 1991).

Protecting groups are used to block some or all reactive moieties and prevent such groups from participating in chemical reactions until the protective group is removed. Protected derivatives are useful in the preparation of the compounds described herein or in themselves may be active as inhibitors. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Protecting or blocking groups may be selected from:

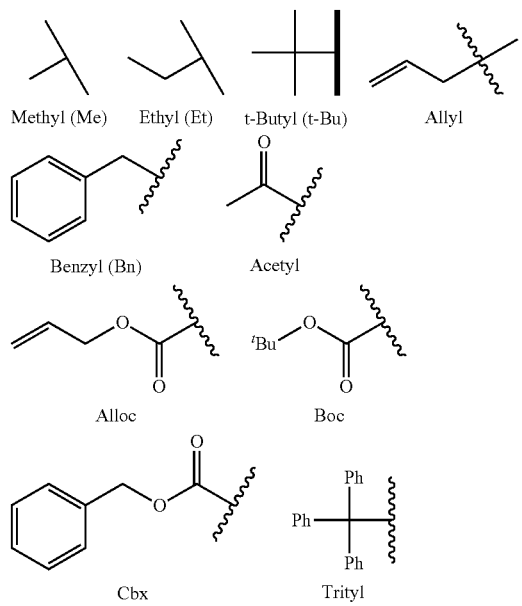

-continued

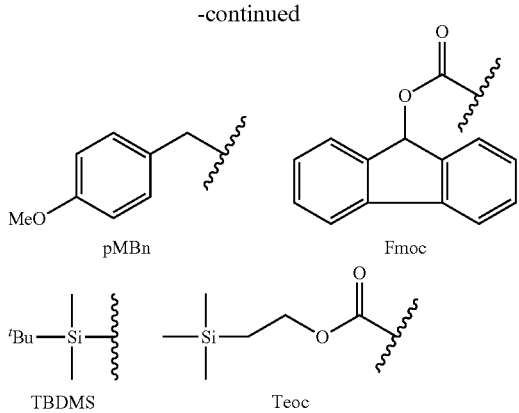

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Further Forms of the Compounds

Isomers

The compounds of Formula I (including without limitation any of the compounds specifically or generically described herein, including the compounds presented in the tables) may exist in the form of optical isomers, e.g. diastereoisomers and mixtures of isomers in all ratios, e.g. racemic mixtures. This includes in particular the isomeric forms (R or S). The different isomeric forms may be separated or resolved one from the other by conventional methods, or any given isomer may be obtained by conventional synthetic methods or by stereospecific or asymmetric synthesis. Where a compound contains an alkene moiety, the alkene can be presented as a cis or trans isomer or a mixture thereof. When an isomeric form of a compound described herein is provided substantially free of other isomers, it will preferably contain less than 5% w/w, more preferably less than 2% w/w and especially less than 1% w/w of the other isomers.

The compounds of Formula I (including without limitation any of the compounds specifically or generically described herein, including the compounds presented in the tables) may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds may exist as tautomers. The compounds described herein include all possible tautomers within the formulas described herein.

The compounds of Formula I (including without limitation any of the compounds specifically or generically described herein, including the compounds presented in the tables) may possess one or more chiral centers and each center may exist in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion may also be useful for the applications described herein.

In some embodiments, the compounds of Formula I (including without limitation any of the compounds specifically or generically described herein, including the compounds presented in the tables) can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Labeled Compounds

It should be understood that the compounds of Formula I (including without limitation any of the compounds specifically or generically described herein, including the compounds presented in the tables) include their isotopically-labeled equivalents, including their use for treating disorders. For example, provided herein are methods of treating diseases, by administering isotopically-labeled compounds of Formula I. The isotopically-labeled compounds described herein can be administered as pharmaceutical compositions. Thus, the compounds described herein also include their isotopically-labeled isomers, which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine and chloride, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{26}Cl$, respectively. Compounds described herein, pharmaceutically acceptable salts, esters, prodrugs, solvate, hydrates or derivatives thereof which contain the aforementioned isotopes and/or other isotopes of other atoms are included herein. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavier isotopes such as deuterium, i. e., $^2H$, can afford certain therapeutic advantages resulting from greater metabolic stability, for example increased in vivo half-life or reduced dosage requirements and, hence, may be preferred in some circumstances. Isotopically labeled compounds, pharmaceutically acceptable salts, esters, prodrugs, solvates, hydrates or derivatives thereof can generally be prepared by carrying out procedures described herein, by substituting a readily available isotopically labeled reagent for a non-isotopically labeled reagent.

The compounds described herein may be labeled by other means, including, but not limited to, the use of chromophores or fluorescent moieties, bioluminescent labels, or chemiluminescent labels.

Pharmaceutically Acceptable Salts

The compounds of Formula I (including without limitation any of the compounds specifically or generically described herein, including the compounds presented in the tables) may also exist as their pharmaceutically acceptable salts, which may also be useful for treating disorders. For example, described are methods of treating diseases, by administering pharmaceutically acceptable salts of the compounds described herein. The pharmaceutically acceptable salts can be administered as pharmaceutical compositions.

Thus, the compounds of Formula I (including without limitation any of the compounds specifically or generically described herein, including the compounds presented in the tables) can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Further, the compounds of Formula I (including without limitation any of the compounds specifically or generically described herein, including the compounds presented in the tables) can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

The compounds described herein may be provided as a salt, preferably as a pharmaceutically acceptable salt of compounds of Formula I. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds described herein include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds described herein include organic bases, which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first aspect described herein in aqueous or aqueous alcohol solution or other suitable solvents containing the required acid. Where a compound described herein contains an acidic function, a base salt of said compound may be prepared by reacting said compound with a suitable base. The acid or base salt may separate directly or can be obtained by concentrating the solution e.g. by evaporation.

Solvates

The compounds of Formula I (including without limitation any of the compounds specifically or generically described herein, including the compounds presented in the tables) may also exist in various solvated forms, which may also be useful for treating disorders. For example, described are methods of treating diseases, by administering solvates of the compounds described herein. The solvates can be administered as pharmaceutical compositions. Preferably the solvates are pharmaceutically acceptable solvates.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

The compounds of Formula I (including without limitation any of the compounds specifically or generically described herein, including the compounds presented in the tables) may also exist in various polymorphic states, all of which are herein contemplated, and which may also be useful for treating disorders. For example, described are methods of treating diseases, by administering polymorphs of the compounds described herein. The various polymorphs can be administered as pharmaceutical compositions.

Thus, the compounds of Formula I (including without limitation any of the compounds specifically or generically described herein, including the compounds presented in the tables) include all their crystalline forms, known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, solvates and solubility. Various factors such as the recrystallization solvent, rate of crystallization, and storage temperature may cause a single crystal form to dominate.

Prodrugs

The compounds of Formula I (including without limitation any of the compounds specifically or generically described herein, including the compounds presented in the tables) may also exist in prodrug form, which may also be useful for treating disorders. For example, described are methods of treating diseases, by administering prodrugs of the compounds described herein. The prodrugs can be administered as pharmaceutical compositions.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Pharmaceutically acceptable prodrugs of the compounds of Formula I (including without limitation any of the compounds specifically or generically described herein, including the compounds presented in the tables) include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5,. p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs:

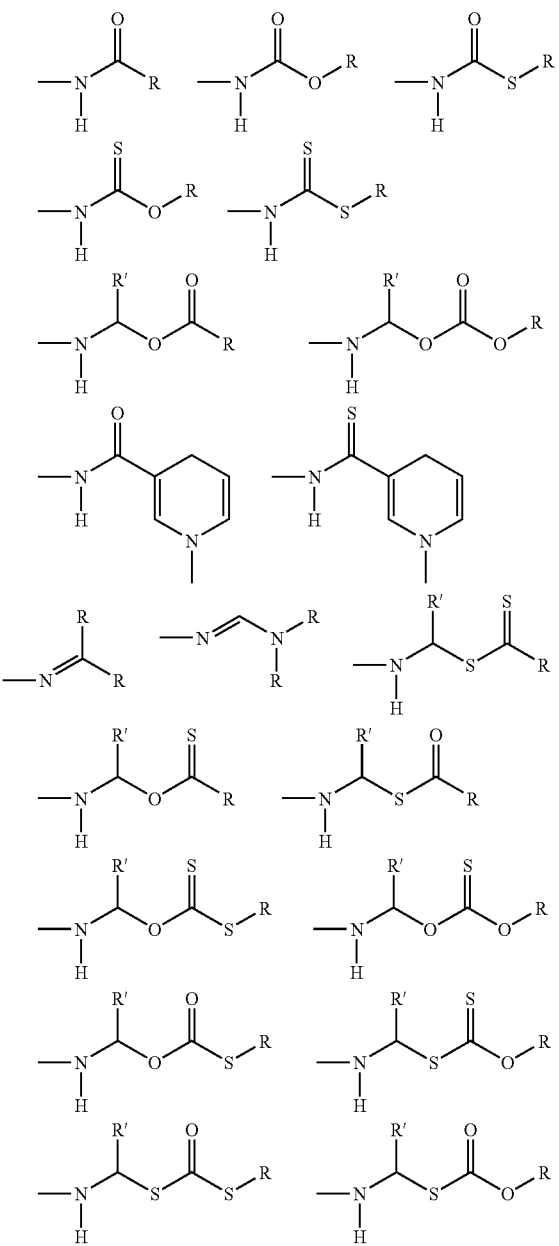

Hydroxy prodrugs include, but are not limited to acyloxyalkyl esters, alkoxycarbonyloxyalkyl esters, alkyl esters, aryl esters and disulfide containing esters.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

Prodrug derivatives of compounds described herein can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of Formula I with a suitable carbamoylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Compounds of Formula I having free amino, amido, hydroxy or carboxylic groups can be converted into prodrugs. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities. Phosphate ester functionalities may also be used as prodrug moieties.

Sites on the aromatic ring portions of compounds of the compounds described herein may be susceptible to various metabolic reactions, therefore incorporation of appropriate substituents on the aromatic ring structures, can reduce, minimize or eliminate this metabolic pathway.

Compound Purity

Because the compounds described herein are intended for use in pharmaceutical compositions, it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5%, e.g. 10 to 59% of a compound of the Formula I.

Pharmaceutical Compositions

The compounds of Formula I (including without limitation any of the compounds specifically or generically described herein, including the compounds presented in the tables) may be administered in the form of a pharmaceutical composition in accordance with one aspect described herein. Such compositions may be presented in conventional dosage forms prepared by combining a compound of Formula I ("active ingredient") with standard pharmaceutical carriers or excipients according to conventional procedures well known in the art. The procedures may involve mixing, granulating and compressing or dissolving the ingredients as appropriate to the desired preparation.

The active ingredient or pharmaceutical composition can be administered simultaneously, separately or sequentially with another appropriate treatment for the fungal disease being treated.

The present invention can be administered alone or as a pharmaceutical composition, thus the invention further provides pharmaceutical compositions and methods of making said pharmaceutical composition. In some embodiments, the pharmaceutical compositions comprise an effective amount of the compounds of Formula I, or a pharmaceutically acceptable salt, prodrug, solvate, polymorph, tautomer or isomer thereof. The pharmaceutical composition may comprise of admixing at least one active ingredient, or a pharmaceutically acceptable salt, prodrug, solvate, polymorph, tautomer or isomer thereof, together with one or more carriers, excipients, buffers, adjuvants, stabilizers, or other materials well known to those skilled in the art and optionally other therapeutic agents. The formulations may conveniently be presented in unit dosage form and may be prepared by any methods well known in the art of pharmacy.

Examples of excipients that may be used in conjunction with the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Example of pharmaceutically acceptable carriers that may optionally be used include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

The active ingredient or pharmaceutical composition may be administered to a subject by any of the routes conventionally used for drug administration, for example they may be adapted for oral (including buccal, sublingual), topical (including transdermal), nasal (including inhalation), rectal, vaginal or parenteral (including subcutaneous, intramuscular, intravenous or intradermal) administration to mammals including humans. The most suitable route for administration in any given case will depend upon the particular compound or pharmaceutical composition, the subject, and the nature and composition and severity of the disease and the physical condition of the subject. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; filler, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions adapted for topical administration may be formulated as ointments, creams, suspensions, lotions powders, solutions, pastes, gels, sprays, aerosols or oils and may contain appropriate conventional additives such as preservatives, solvents to assist drug penetration and emollients in ointments and creams. Such applications include those to the eye or other external tissues, for example the mouth and sin and the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base. The composition may also contain compatible conventional carriers, such as cream or ointment bases and ethanol or oleoyl alcohol for lotions.

Pharmaceutical compositions adapted for topical administration to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for transdermal administration may be presented as discrete patches intended to remain in intimate contact with the epiderma of the recipient for a prolonged period of time. For example, the active ingredient may be delivered from the patch by iontophoresis as generally described in *Pharmaceutical Research,* 3(6), 318 (1986).

Pharmaceutical compositions adapted for controlled or sustained release may be administered by injection, for example by the subcutaneous route.

Pharmaceutical compositions adapted for nasal administration wherein the carrier is a solid include coarse powder having a particle size for example in the range of 20-500 microns which is administered by rapid inhalation through the nasal passage from a container of the powder held close to the nose. Suitable compositions wherein the carrier is a liquid, for administration as a nasal spray or as nasal drops, include aqueous or oil solutions of an active ingredient.

Pharmaceutical compositions adapted for administration by inhalation include fine particle dusts or mists which may be generated by means of various types of metered dose pressurise aerosols, nebulizers or insufflators.

Pharmaceutical compositions adapted for rectal administration may be presented as suppositories or enemas. Suppositories will contain conventional suppository bases, e.g. cocoa-butter or other glyceride.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solution and suspensions may be prepared from sterile powders, granules and tablets.

For parenteral administration, fluid unit dosage forms are prepared utilising the active ingredient and a sterile vehicle, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Modes of Administration

Described herein are compounds of Formula I or a pharmaceutically acceptable salt, solvate, polymorph, ester, tautomer or prodrug thereof. Also described, are pharmaceutical compositions comprising a compound of Formulas I or a pharmaceutically acceptable salt, solvate, polymorph, ester, tautomer or prodrug thereof. The compounds and compositions described herein may be administered either alone or in combination with pharmaceutically acceptable carriers, excipients or diluents, in a pharmaceutical composition, according to standard pharmaceutical practice.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, intrapulmonary, rectal administration, by implant, by a vascular stent impregnated with the compound, and other suitable methods commonly known in the art. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, nonporous, or gelatinous material, including membranes, such as silastic membranes, or fibers. The administration can also be by direct injection at the site (or former site) of a tumor or neoplastic or pre-neoplastic tissue. Those of ordinary skill in the art are familiar with formulation and administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The formulations include those suitable for oral, parenteral (including subcutaneous, intradermal, intramuscular, intravenous, intraarticular, intramedullary, intracardiac, intrathecal, intraspinal, intracapsular, subcapsular, intraorbital, intratracheal, subcuticular, intraarticular, subarachnoid, and intrasternal), intraperitoneal, transmucosal, transdermal, rectal and topical (including dermal, buccal, sublingual, intranasal, intraocular, and vaginal) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. Tablets may optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, biocide, bacteriostats and solutes which render the formulation isotonic with the blood of the intended recipient; and aqueous and non-aqueous sterile suspensions which may include suspending agents and thickening agents. Examples of suitable isotonic vehicles for use in such formulations include Sodium Chloride Injection, Ringer's Solution, or Lactated Ringer's Injection. Suitable lipophilic solvents or vehicles include fatty oils such as sesame oil, or synthetic fatty acid esters, such as ethyl oleate or triglycerides, or liposomes or other microparticulate systems may be used to target the compound to blood components or one or more organs. The concentration of the active ingredient in the solution may vary widely. Typically, the concentration of the active ingredient in the solution is from about 1 ng/ml to about 10 µg/ml, for example from about 10 ng/ml to about 1 µg/ml. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, suspensions, powders, solutions, spray, aerosol, oil, and drops suitable for administration to the eye, ear or nose. Alternatively, a formulation may comprise a patch or a dressing such as a bandage or adhesive plaster impregnated with active ingredients and optionally one or more excipients or diluents. The amount of active ingredient present in the topical formulation may vary widely. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

The compounds or compositions described herein can be delivered in a vesicle, e.g., a liposome (see, for example, Langer, *Science* 1990, 249, 1527-1533; Treat et al., *Liposomes in the Therapy of Infectious Disease and Cancer*, Lopez-Bernstein and Fidler, Ed., Liss, N.Y., pp. 353-365, 1989). The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. *Surgery,* 1980 88, 507; Saudek et al. *N. Engl. J. Med.* 1989, 321, (574). Additionally, a controlled release system can be placed in proximity of the therapeutic target. (See, Goodson, *Medical Applications of Controlled Release,* 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition described herein can be used. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Methods of Dosing and Treatment Regimens

The compounds of Formula I (including without limitation any of the compounds specifically or generically described herein, including the compounds presented in the tables) can be used in the preparation of medicaments for the treatment of leukotriene-dependent or leukotriene mediated diseases or conditions. In addition, a method for treating any of the diseases or conditions described herein in a subject in need of such treatment, involves administration of pharmaceutical compositions containing at least one compound of any of Formula I, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%,25%,30%, 35%,40%, 45%, 50%, 55%, 60%, 65%, 70%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more subdoses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multidose containers, with an added preservative.

The daily dosages appropriate for the compounds of Formula (G), Formula (G-A), and Formula (G-I), and Formula (G-II), described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration comprise from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Dosage Forms

The pharmaceutical composition may, for example, be in a form suitable for oral administration as a tablet, capsule, cachet, pill, lozenge, powder or granule, sustained release formulations, solution, liquid, suspension, for parenteral injection as a sterile solution, suspension or emulsion, for topical administration as an ointment, cream, lotions, sprays, foams, gel or paste, or for rectal or vaginal administration as a suppository or pessary. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Pharmaceutically acceptable carrier and/or diluent may include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Dosage unit form refers to physically discrete units suited as unitary dosages for the mammalian subjects to be treated; each unit containing a predetermined quantity of active material calculated to produce the desired therapeutic effect in association with the required pharmaceutical carrier. It is especially advantageous to formulate parenteral compositions in dosage unit form for ease of administration and uniformity of dosage. The specification for the novel dosage unit forms described herein are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch or other cellulosic material, alginic acid and certain complex silicates and with binding agents such as sucrose, gelatin and acacia. Additionally, lubricating agents such as magnesium stearate, sodium lauryl sulfate and talc are often useful for tableting purposes. Other reagents such as an inhibitor, surfactant or solubilizer, plasticizer, stabilizer, viscosity increasing agent, or film forming agent may also be added. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Advantageously, agents such as local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the active ingredient is suspended in the vehicle instead of being dissolved and sterilisation cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

In some embodiments, the pharmaceutical compositions according to the invention are preferably adapted for oral administration.

It should be understood that in addition to the ingredients particularly mentioned above, the compositions may also include other agents conventional in the art having regard to the type of formulation in question, for example those suitable for oral administration may include flavoring agents. They may also contain therapeutically active agents in addition to the compounds of the present invention. Such carriers may be present as from about 1% up to about 98% of the formulation. More usually they will form up to about 80% of the formulation.

The compositions may contain from 0.1% by weight, preferably from 10-60% by weight, of the active material depending on the method of administration.

Pharmaceutical compositions may be presented in unit dose forms containing a predetermined amount of active ingredient per dose. Such a unit may contain for example 0.1 mg/kg to 750 mg/kg, more preferably 0.1 mg/kg to 10 mg/kg depending on the condition being treated, the route of administration and the age, weight and condition of the patient. Preferred unit dosage compositions are those containing a daily dose or sub-dose, as herein above recited, or an appropriate fraction thereof, of an active ingredient.

It will be recognized by one of skill in the art that the optimal quantity and spacing of individual dosages of compounds in the first and second aspects described herein will be determined by the nature and extent of the condition being treated the form, route and site of administration, and the particular subject being treated, and that such optimums can be determined by conventional techniques. It will also be appreciated by one of skill in the art that the optimal course of treatment, i.e., the number of doses of the aforementioned compounds given per day for a defined number of days, can be ascertained by those skilled in the art using conventional course of treatment determination tests.

Depending on the route of administration, the chemical compound or composition may be required to be coated in a material to protect it from the action of enzymes, acids and other natural conditions which may inactivate it.

In order to administer the chemical compound or composition by other than parenteral administration, it may be coated by, or administered with, a material to prevent its inactivation. For example, it may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleoyl ether and n-hexadecyl polyethylene ether.

Liposomes include water-in-oil-in-water CGF emulsions as well as conventional liposomes.

The active chemical compound or composition may also be administered parenterally or intraperitoneally. Dispersions can also be prepared in glycerol, liquid polyethylene glycols, and mixtures thereof and in oils. Under ordinary conditions of storage and use, these preparations contain a preservative.

The pharmaceutical compositions or formulations suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

Prolonged absorption of the injectable compositions can be brought about by the use in the compositions of agents delaying absorption, for example, aluminium monostearate and gelatin.

Sterile injectable solutions are prepared by incorporating the active chemical compound or composition in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the chemical compound or composition is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavoring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The methods described herein include inhibiting 1,3-β-D-glucan synthesis in a fungus by contacting the fungus with a composition containing an amount of a selective 1,3-(β-D-glucan synthase (BGS) inhibitor compound effective for inhibiting synthesis of 1,3-β-D-glucan. A fungus may be contacted with the composition ex vivo or in vivo, e.g., to treat a subject suffering from a pathological fungal infection (e.g., an invasive fungal infection). As used herein, "treating" or "treat" is intended to include preventing, ameliorating, curing, reducing fungal growth or reducing associated symptoms, or preventing any increase in fungal growth or associated symptoms.

A subject in need of treatment with any of the compositions or methods described herein include, but are not limited to, a subject having a fungal infection, or a subject at risk of developing a fungal infection. The subject may have been diagnosed as having such a fungal infection as described herein or using standard medical techniques known to those of skill in the art. For example, the plasma levels of (1→3)-β-D-glucan in serum can be assayed, where a serum level of (1→3)-β-D-glucan above about 40, 50, 60, or 80 pg/ml indicates a likely infection by *Candida* and *Aspergillus*. Alternatively, highly sensitive "pan-fungal" nucleic acid-based diagnostic assays can be used. See, e.g., Van Burik et al. (1998), *J. of Clin. Microbiol*, 36(5): 1169-1175; and Lau et al. (2007), *J. of Clin. Microbiol*. 45(2):380-385. In addition, such assays can be used to monitor the efficacy of treatment for a fungal infection. See, e.g., Kondori et al. (2004), *Clinical and Diagnostic Laboratory Immunology*, 11(2):344-350. Alternatively a subject may exhibit one or more symptoms of fungal infection.

A subject at risk of developing a fungal infection is a subject who has been exposed to a fungus, or is susceptible to exposure to a fungus. For instance a subject that is susceptible to exposure to a fungus includes those subjects who work with fungal material or in areas of high fungal content, subjects who travel to areas with high fungal infectivity rates or are otherwise likely to be exposed to a fungal infection as well as those subjects having particular susceptibility to fungal infection resulting from medical conditions or therapies.

Examples of subjects having particular susceptibility to fungal infections arising from medical conditions or therapies include but are not limited to subjects who are immunocompromised. An immunocompromised subject is a subject that is incapable of inducing a normal effective immune response or a subject that has not yet developed an immune system (e.g. preterm neonate). For example, the subject may be immunocompromised due to AIDS (or AIDS treatment), cancer (or cancer treatment), severe combined immunodeficiency, ongoing treatment with an immunosuppressive agent, e.g., for suppression of organ transplant immune rejection, or for treatment of an autoimmune, heteroimmune, or inflammatory condition.

In some cases, a subject in need of treatment for a fungal infection may be suffering from tuberculosis, diabetes, severe burns, or intravenous drug abuse. In other cases, the subject in need is undergoing prolonged use of an intravenous or urinary catheter or is being subjected to chronic antibiotic exposure or chronic corticosteroid exposure.

Fungi whose growth can be inhibited by the compositions and methods described herein include, but are not limited to, moulds, e.g., *Aspergillus fumigatus, A. flavus, A. niger, A terreus, A flavus, A nidulans, A sydowi, Paecilomyces lilcinus, Fusarium solani*, or, *F. oxysporum*, or *Histoplasma capsulatum*; and yeast, e.g., *Candida aaseri, C. acidothermophilum, C. acutus, C. albicans, C. anatomiae, C. apis, C. apis* var. *galacta, C. atlantica, C. atmospherica, C. auringiensis, C. bertae, C. berthtae* var. *chiloensis, C. berthetii, C. blankii, C. boidinii, C. boleticola, C. bombi, C. bombicola, C. buinensis, C. butyri, C. cacaoi, C. cantarellii, C. cariosilignicola, C. castellii, C. castrensis, C. catenulata, C. chilensis, C. chiropterorum, C. coipomensis, C. dendronema, C. deserticola, C. diddensiae, C. diversa, C. entomaea, C. entomophila, C. ergatensis, C. ernobii, C. ethanolica, C. ethanothermophilum, C. famata, C. fluviotilis, C. fragariorum, C. fragicola, C. friedrichii, C. fructus, C. geochares, C. glabrata, C. glaebosa, C. gropengiesseri, C. guilliermondii, C. guilliermondii* var. *galactosa, C. guilliermondii* var. *soya, C. haemulonii, C. halophila/C. versatilis, C. holmii, C. humilis, C. hydrocarbofumarica, C. inconspicua, C. insectalens, C. insectamans, C. intermedia, C. javanica, C. kefyr, C. krissii, C krusei, C. krusoides, C. lambica, C. lusitaniae, C. magnoliae, C. maltosa, C. mamillae, C. maris, C. maritima, C. melibiosica, C. melinii, C. methylica, C. milleri, C. mogii, C. molischiana, C. montana, C. multis-gemmis, C. musae, C. naeodendra, C. nemodendra, C. nitratophila, C. norvegensis, C. norvegica, C. oleophila, C. oregonensis, C. osornensis, C. paludigena, C. parapsilosis, C. pararugosa, C. periphelosum, C. petrohuensis, C. petrophilum, C. philyla, C. pignaliae, C. pintolopesii* var. *pintolopesii, C. pintolopesii* var. *slooffiae, C. pinus, C. polymorpha, C. populi, C. pseudointermedia, C. quercitrasa, C railenensis, C. rhagii, C. rugopelliculosa, C. rugosa, C. sake, C. salmanticensis, C. savonica, C sequanensis, C. shehatae, C. silvae, C. silvicultrix, C. solani, C. sonorensis, C. sorbophila, C. spandovensis, C. sphaerica, C. stellata, C succiphila, C. tenuis, C. terebra, C. tropicalis, C. utilis, C. valida, C. vanderwaltii, C. vartiovaarai, C. veronae, C. vini,*

*C. wickerhamii, C. xestobii, C. zeylanoides, Saccharomyces cerevisiae, Kluyveromyces lactis,* or *Schizosaccharomyces pombe.*

Examples of fungal infections that can be treated with the compositions and methods described herein described include, but are not limited to, blastomycosis, tinea, coccidiomycosis, cryptococcosis, candidiasis, moniliasis, dermatomycosis, dermatophytosis, favus, keratomycosis, phycomycosis, sporotrichosis, or rhinosporidiosis.

Combination Therapies

The compounds described herein or a pharmaceutically acceptable salt, prodrug, solvate, polymorph, tautomer or isomer thereof may be administered as a sole therapy. The compounds described herein their pharmaceutically acceptable salts, prodrug, solvates, polymorphs, tautomers or isomers may also be administered in combination with another therapy or therapies. Combination treatments may occur sequentially or concurrently and the combination therapies may be neoadjuvant therapies or adjuvant therapies.

In some embodiments, the compounds described herein can be administered with an additional therapeutic agent. In these embodiments, the compound described herein can be in a fixed combination with the additional therapeutic agent or a non-fixed combination with the additional therapeutic agent.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of another therapeutic agent, the overall therapeutic benefit to the patient is enhanced. Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain good blood levels thereof, while the other therapeutic agent may be administered intravenously. The determination of the mode of administration and the advisability of administration, where possible, in the same pharmaceutical composition, is within the knowledge of the skilled clinician with the teachings described herein. The initial administration can be made according to established protocols known in the art, and then, based upon the observed effects, the dosage, modes of administration and times of administration can be modified by the skilled clinician. The particular choice of compound (and where appropriate, other therapeutic agent and/or radiation) will depend upon the diagnosis of the attending physicians and their judgment of the condition of the patient and the appropriate treatment protocol.

Antifungal Compounds

Where a subject is in need of treatment for a fungal infection, any of the selective BGS inhibitor compounds described herein can be used in combination with a supplemental antifungal compound including, but not limited to other echinocandin antifungal compounds (e.g., anidulafungin, caspofungin, or micafungin); polyene antifungal compounds (e.g., natamycin, rimocidin, nystatin, or amphotericin B); imidazole antifungal compounds (e.g., miconazole, ketoconazole, clotrimazole, econazole, bifonazole, butoconazole, fenticonazole, isoconazole, oxiconazole, sertaconazole, sulconazole, or tioconazole); triazole antifungal compounds (e.g., fluconazole, itraconazole, isavuconazole ravuconazole, posaconazole, voriconazole, or terconazole); allylamines (e.g., terbinafine, amorolfine, naftifine, or butenafine); and other antifungal compounds such as ciclopirox olamine, 5-fluorocytosine, gentian violet, haloprogin, tolnaftate, or undecylenic acid.

Immunosuppressive Agents

Where a subject requires immunosuppressive therapy, any of the selective BGS inhibitor compounds described herein can be administered to the subject prophylactically or therapeutically to treat a fungal infection in combination with one or more immunosuppressive agents administered to induce immunosuppression. Examples of immunosuppressive agents include, but are not limited to, corticosteroids, cyclophosphamide, folic acid analogues, methotrexate, purine analogues, azathioprine, mercaptopurine, methotrexate, dactinomycin, anthracyclines, mitomycin c, bleomycin, mithramycin, IL-2 receptor antibodies, CD3 directed antibodies, OKT33 (R), anti-CD3 antibody, anti-CD25 antibodies, tacrolimus, cyclosporin, tacrolimus, rapamicin, ifn-β, ifn-γ, infliximab, etanercept, adalimumab, curcumin, catechins, mycophenolic acid, or FTY720.

Chemotherapy Agents

Where a subject is suffering from a cancer, any of the selective BGS inhibitor compounds described herein can be administered to the subject prophylactically or therapeutically to treat a fungal infection in combination with one or more chemotherapy agents administered to treat the cancer. Examples of chemotherapy agents include, but are not limited to, any of the following:., 5-aza-2'-deoxycytidine, all trans retinoic acid, doxorubicin, vincristine, etoposide, gemcitabine, imatinib (Gleevec®), 17-n-allylamino-17-demethoxygeldanamycin (17-aag), flavopiridol, ly294002, bortezomib, trastuzumab, bay 11-7082, pkc412, pd184352, paclitaxel, adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea;

idarubicin hydrochloride; ifosfamide; ilmofosine; interleukins, interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozoicin; sulofenur; talisomycin; tecogalan sodium; tegafur; teloxantrone hydrochloride; temoporfin; teniposide; teroxirone; testrolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; or zorubicin hydrochloride.

Anti-Inflammatory Agents

Where a subject is suffering from an inflammatory condition, any of the selective BGS inhibitor compounds described herein can be administered to the subject prophylactically or therapeutically to treat a fungal infection in combination with one or more anti-inflammatory compounds administered to treat the inflammatory condition. Examples of anti-inflammatory agents include, but are not limited to, amcinolide, betamethosone diprionate, budesonide, clobetasol, clocortolone, dexamethasone, diflorasone, dutasteride, flumethasone pivalate, flunisolide, fluocinolone acetonide, fluocinonide, fluorometholone, fluticasone propionate, fluradrenolide, hydroflumethiazide, aspirin, amoxiprin, benorilate, choline magnesium salicylate, diflunisal, faislamine, methyl salicylate, magnesium salicylate, and salicyl salicylate (salsalate); arylalkanoic acids, e.g., diclofenac, aceclofenac, acemetacin, bromfenac, etodolac, indometacin, nabumetone, sulindac, and tolmetin; 2-arylpropionic acids (profens), e.g., ibuprofen carprofen, fenbufen, fenoprofen, flurbiprofen, ketoprofen, ketorolac, loxoprofen, naproxen, tiaprofenic acid, and suprofen; n-arylanthranilic acids (fenamic acids), e.g., mefenamic acid and meclofenamic acid; pyrazolidine derivatives, e.g., phenylbutazone, azapropazone, metamizole, oxyphenbutazone, and sulfinprazone; oxicams, e.g., piroxicam, lomoxicam, meloxicam, and tenoxicam; cox-2 inhibitors, e.g., etoricoxib, lumiracoxib, and parecoxib; sulphonanilides such as nimesulide; or other non-steroidal anti-inflammatory agents, e.g., licofelone and omega-3 fatty acids.

Antibiotics

Where a subject is suffering from a bacterial infection, any of the selective BGS inhibitor compounds described herein can be administered to the subject prophylactically or therapeutically to treat a fungal infection in combination with one or more antibiotic compounds agents administered to treat the bacterial infection. Examples of antibiotics include, but are not limited to, amikacin, gentamicin, kanamycin, neomycin, netilmicin, streptomycin, tobramycin, geldanamycin, herbimycin, loracarbef, ertapenem, imipenem/cilastatin, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, vancomycin, azithromycin, clarithromycin, dirithromycin, erythromycin, roxithromycin, troleandomycin, aztreonam, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin b, ciprofloxacin, enoxacin, gatifloxacin, levofloxacin, lomefloxacin, moxifloxacin, norfloxacin, ofloxacin, trovafloxacin, mafenide, prontosil (archaic), sulfacetamide, sulfamethizole, sulfanilimide (archaic),sulfasalazine, sulfisoxazole, trimethoprim, trimethoprim-sulfamethoxazole (co-trimoxazole) (tmp-smx), demeclocycline, doxycycline, minocycline, oxytetracysline, tetracycline, arsphenamine, chloramphenicol, clindamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin, spectinomycin, or telithromycin.

Anti-HIV Compounds

Where a subject is suffering from an HIV infection (e.g., suffering from AIDS), any of the selective BGS inhibitor compounds described herein can be administered to the subject prophylactically or therapeutically to treat a fungal infection in combination with one or more anti-HIV compounds administered to treat the HIV infection. Examples of anti-HIV compounds include, but are not limited to, AZT (zidovudine, Retrovir), ddI (didanosine, Videx), 3TC (lamivudine, Epivir), d4T (stavudine, Zerit), abacavir (Ziagen), and FTC (emtricitabine, Emtriva), tenofovir (Viread), efavirenz (Sustiva), nevirapine (Viramune), lopinavir/ritonavir (Kaletra), indinavir (Crixivan), ritonavir (Norvir), nelfinavir (Viracept), saquinavir hard gel capsules (Invirase), atazanavir (Reyataz), amprenavir (Agenerase), fosamprenavir (Telzir), tipranavir (Aptivus), or T20 (enfuvirtide, Fuzeon).

Anti-Diabetic Agents

Where a subject is suffering from diabetes, any of the selective BGS inhibitor compounds described herein can be administered to the subject prophylactically or therapeutically to treat a fungal infection in combination with one or more anti-diabetic agents compounds administered to treat the diabetes. Examples of antidiabetic agents include, but not limited to, insulin secretagogues, insulin sensitizers, biguanides, sulfonyl ureas, glucosidase inhibitors, peroxisome proliferator activated receptor (PPAR) γ agonists, such as thiazolidinediones, PPAR α agonists such as fibric acid derivatives, aP2 inhibitors, dipeptidyl peptidase IV (DP4) inhibitors, sodium-glucose co-transporter type 2 (SGLT2) inhibitors, meglitinides, insulin, glucagon-like peptide-1 (GLP-1), GLP-1(1-36) amide, GLP-1 (7-36) amide, GLP-1 (7-37) (as disclosed in U.S. Pat. No. 5,614,492, as well as AC2993, LY-315902, metformin, phenformin or glyburide (also known as glibenclamide), glimepiride (disclosed in U.S. Pat. No. 4,379,785), glipizide, gliclazide or chlorpropamide, acarbose (disclosed in U.S. Pat. No. 4,904,769), miglitol (disclosed in U.S. Pat. No. 4,639,436), troglitazone (disclosed in U.S. Pat. No. 4,572,912), rosiglitazone, pioglitazone, MCC-555 (disclosed in U.S. Pat. No. 5,594,016), GL-262570, englitazone, darglitazone, isaglitazone, JTT-501, L-895645, R-119702, NN-2344, YM-440, AR-HO39242 GW-409544, or KRP297.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, disease state for which the composition is to be administered, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer. The packaging material may comprise a container for housing the composition and optionally a label affixed to the container. The kit may also optionally comprise additional components, such as syringes for administration of the composition. The kit may comprise the composition in single or multiple dose forms.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals, exotic animals and farm animals, including mammals, rodents, and the like. More preferred animals include horses, dogs, and cats.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic

EXAMPLES

The examples and preparations provided below further illustrate and exemplify the compounds of the present invention and methods of preparing such compounds. It is to be understood that the scope of the present invention is not limited in any way by the scope of the following examples and preparations. The experimental procedures to generate the data shown are discussed in more detail below. The invention has been described in an illustrative manner, and it is to be understood that the terminology used is intended to be in the nature of description rather than of limitation.

I. Chemical Syntheses

Compounds according to the invention may be prepared by any suitable method known in the art. Exemplary methods for making the compounds in accordance with the invention are shown below. It should be understood that the following are provided for exemplary purposes and additional compounds and compounds with additional substitutions are contemplated by the present invention. Also, where a substituent is exemplified on one compound, it should be understood that that substituent could also be attached to any of the other compounds described herein.

Example 1 was prepared according to Scheme 1.

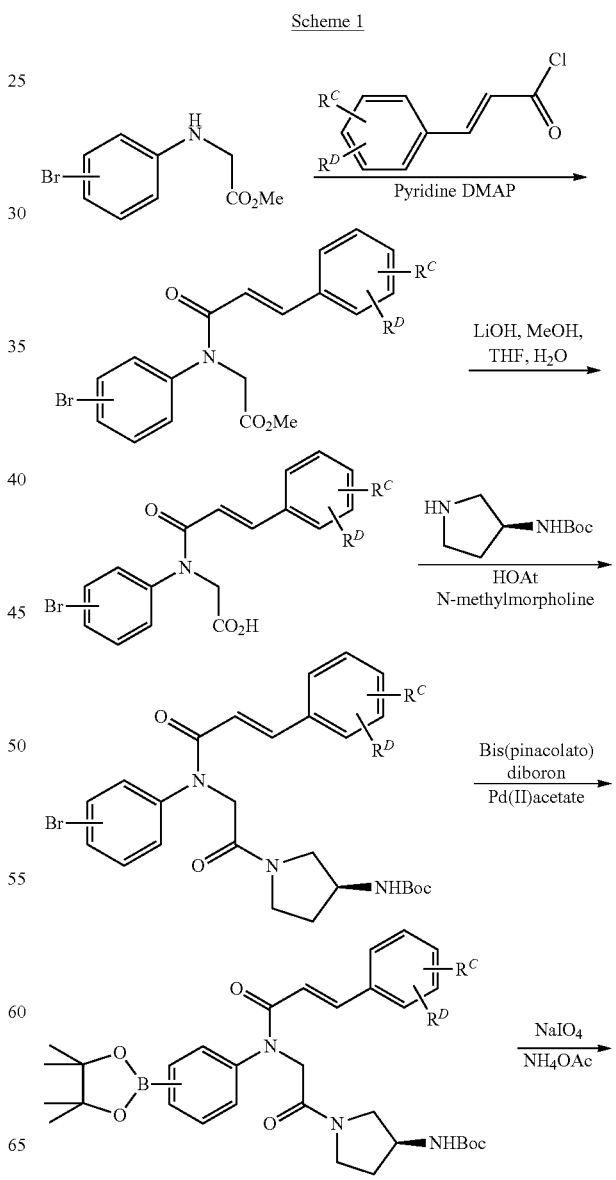

Scheme 1

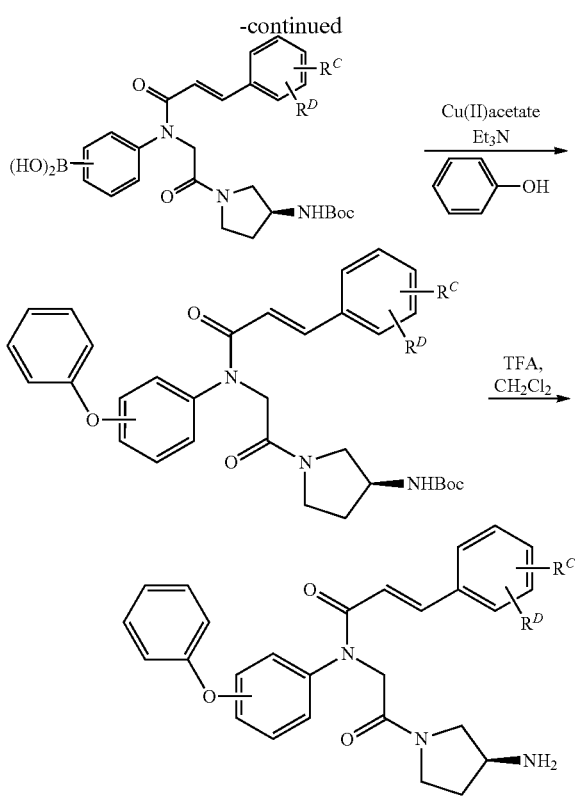

Example 1

Synthesis of (E)-N-[2-((S)-3-Aminopyrrolidin-1-yl)-2-oxo-ethyl]-N-(4-phenoxyphenyl)-3-phenylacrylamide (OGT4344)

Compound 1 (Intermediate)

{(4-Bromophenyl)-[(E)-(3-phenylacryloyl)]amino}acetic acid, methyl ester

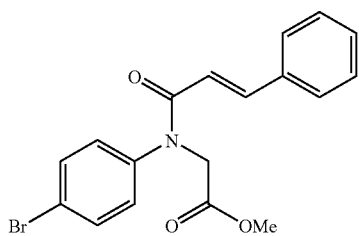

(4-Bromophenylamino)acetic acid, methyl ester (8.74 g, 0.036 mol) was treated with cinnamoyl chloride (11.99 g, 0.072 mol) in pyridine (50 mL) in the presence of 4-dimethylaminopyridine (0.489 g, 0.004 mol). The reaction mixture was stirred at room temperature for 2 h. The crude product was purified by flash column chromatography on silica gel, eluting with ethyl acetate/dichloromethane (1:20), to give the title compound as a white crystalline solid (13.13 g, 98%). $^1$HNMR (300 MHz) (CDCl$_3$) δ 3.67 (3H, s), 4.42 (2H, s), 6.28 (1H, d, J=16 Hz), 7.19 (2H, d), 7.2-7.3 (5H, m), 7.51 (2H, d) and 7.66 (1H, d, J=16Hz).

Compound 2 (Intermediate)

{(4-Bromophenyl)-[(E)-(3-phenylacryloyl)]amino}acetic acid

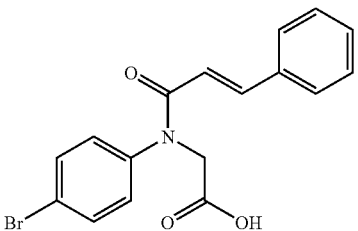

A solution of {(4-bromophenyl)-[(E)-(3-phenylacryloyl)]amino}acetic acid, methyl ester 1 (14.61 g, 0.39 mol) in THF (150 mL) and methanol (50 mL) was treated with lithium hydroxide (2.80 g, 0.117 mol) in water (50 mL). The reaction mixture was stirred at room temperature for 45 min and then acidified with conc. hydrochloric acid and concentrated in vacuo. The residue was diluted with ethyl acetate and washed with 10% hydrochloric acid, brine, dried (Na$_2$SO$_4$) and the organic solution evaporated to give the title compound as a viscous oil (13.82 g, 97%). $^1$HNMR (300 MHz) (CDCl$_3$) δ 4.53 (2H, s), 6.36 (1H, d, J=16 Hz), 7.27 (2H, d), 7.3-7.4 (5H, m), 7.60 (2H, d) and 7.76 (1H, d, J=16 Hz).

Compound 3 (Intermediate)

[(S)-1-(2-{(4-Bromophenyl)-[(E)-(3-phenylacryloyl)]amino}acetyl)pyrrolidin-3-yl]carbamic acid, tert-butyl ester

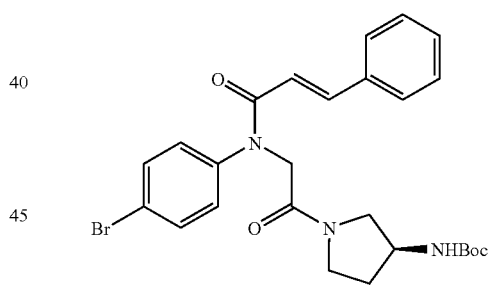

1-Ethyl-3-(3'-dimethylaminopropyl)carbodiimide (9.39 g, 0.049 mol) was added to a solution of {(4-Bromophenyl)-[(E)-(3-phenylacryloyl)]amino}acetic acid 2 (13.82 g, 0.038 mol), (3S)-(−)-3-(tert-butoxycarbonylamino)pyrrolidine (9.13 g, 0.049 mol), 1-hydroxy-7-azabenzotriazole (6.67 g, 0.049 mol) and N-methylmorpholine (8.4 mL, 0.08 mol) in DMF (150 ml). The reaction mixture was stirred at room temperature for 16 h and then concentrated in vacuo. The residue was diluted with ethyl acetate and washed with 10% hydrochloric acid (×3), brine, saturated aqueous sodium bicarbonate (×2) and brine. The title compound began to crystallize during work-up and was collected by filtration. The mother liquor was concentrated to provide a further quantity of product. Total yield of title compound: 17.43 g, 86%. $^1$HNMR (300 MHz) (CDCl$_3$) δ 1.45 (6H, s), 1.60 (3H, s), 1.7-2.3 (2H, m), 3.4-3.8 (4H, m), 4.1-4.9 (3H, m), 6.36 (1H, d, J=16 Hz), 7.36 (2H, d), 7.2-7.4 (5H, m), 7.55 (2H, d) and 7.70 (1H, d, J=16 Hz).

Compound 4 (Intermediate)

[(S)-1-(2-{[4-(4,4,5,5-Tetramethyl-1,3,2-dioxaborolan-2-yl)phenyl]-[(E)-(3-phenylacryloyl)]amino}acetyl)pyrrolidin-3-yl]carbamic acid, tert-butyl ester

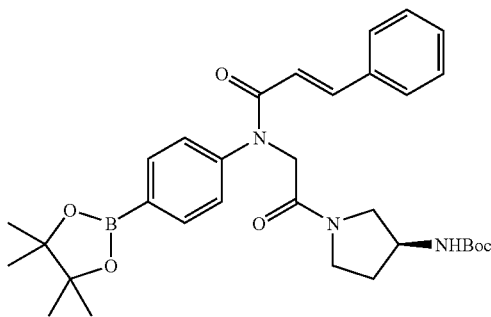

DMF (20 mL) was added to a mixture of [(S)-1-(2-{(4-bromophenyl)-[(E)-(3-phenylacryloyl)]amino}acetyl)pyrrolidin-3-yl]carbamic acid, tert-butyl ester 3 (2.00 g, 3.78 mmol), potassium acetate (1.1 g, 11.3 mmol), palladium[II] acetate (25 mg, 0.113 mmol) and bis(pinacolato)diboron (1.15g, 4.54 mmol). The reaction mixture was stirred and degassed and then argon was bubbled through. The mixture was heated at 85° C. under argon, with stirring, for 5.5 h. The reaction was diluted with ethyl acetate and washed with 10% hydrochloric acid (×2), brine, dried ($Na_2SO_4$) and evaporated to dryness. The residue was purified by flash column chromatography on silica gel, eluting with ethyl acetate, to give the title compound as an oil (1.85 g, 71%). $^1$HNMR (300 MHz) (CDCl$_3$) δ 1.36 (12H, s), 1.45 (6H, s), 1.58 (3H, s), 1.7-2.3 (2H, m), 3.4-3.8 (3H, m), 4.2-4.9 (2H, m), 6.43 (1H, d, J=16 Hz), 7.23-7.37 (5H, m), 7.45 (2H, d), 7.70 (1H, d, J=16 Hz) and 7.86 (2H, d).

Compound 5

[(S)-1-(2-{(4-Borono-phenyl)-[(E)-(3-phenylacryloyl)]amino}acetyl)pyrrolidin-3-yl]carbamic acid, tert-butyl ester

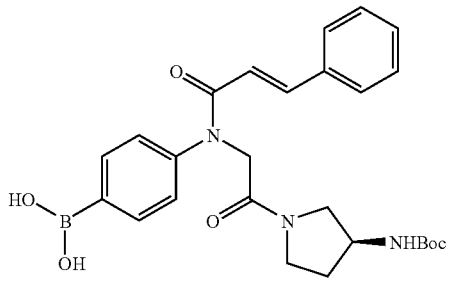

Sodium periodate (2.06 g, 9.6 mmol) and ammonium acetate (0.74 g, 9.6 mmol) in water (20 mL) were added to [)S)-1-(2-{[4-(4,4,5,5-tetramethyl-1,3,2-dioxaborolan-2-yl)phenyl]-[(E)-(3-phenylacryloyl)]amino}acetyl)pyrrolidin-3-yl]-carbamic acid, tert-butyl ester 4 (1.85 g, 3.2 mmol) in acetone (30 mL) and the reaction stirred at room temperature for 64 h. The reaction mixture was concentrated in vacuo and 1M NaOH was added. The mixture was stirred for 4 h and then shaken with dichloromethane and filtered. The two layers were separated and the NaOH layer washed with dichloromethane. The aqueous basic layer was acidified to pH1 with conc. hydrochloric acid and extracted with ethyl acetate (×2). The combined organic layers were washed with brine, dried ($Na_2SO_4$) and evaporated to dryness. The resultant residue was purified by flash column chromatography on silica gel, eluting with ethyl acetate→5% methanol/ethyl acetate→10% methanol/ethyl acetate→methanol, to give the title compound as a glass (1.26 g, 80%) which was used directly in the next stage.

Compound 6

[(S)-1-(2-{(4-Phenoxyphenyl)-[(E)-(3-phenylacryloyl)]amino}acetyl)pyrrolidin-3-yl]carbamic acid, tert-butyl ester

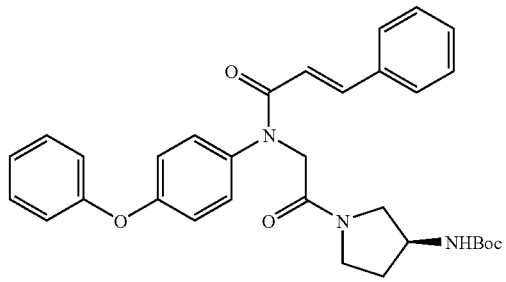

Triethylamine (0.13 mL, 0.91 mmol) was added to [(S)-1-(2-{(4-borono-phenyl)-[(E)-(3-phenylacryloyl)]amino}acetyl)pyrrolidin-3-yl]carbamic acid, tert-butyl ester 5 (90 mg, 0.18 mmol), copper[II]acetate, 4 Å sieve (powdered) and phenol (26 mg, 0.27 mmol) in dichloromethane (4 mL). The reaction mixture was stirred at room temperature for 16 h and then diluted with dichloromethane and washed with 10% hydrochloric acid, 1M NaOH (×2) and brine, dried ($Na_2SO_4$) and evaporated to dryness. The residue was purified by column chromatography on silica gel, eluting with ethyl acetate/petrol (2:1), to give the title compound as a white powder (60 mg) which was used directly in the next stage.

Compound 7

(E)-N-[2-((S)-3-Aminopyrrolidin-1-yl)-2-oxo-ethyl]-N-(4-phenoxyphenyl)-3-phenylacrylamide (OGT4344)

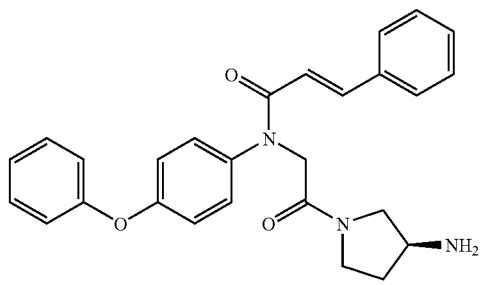

Trifluoroacetic acid (2 mL) was added to a solution of [(S)-1-(2-{(4-phenoxyphenyl)-[(E)-(3-phenylacryloyl)]amino}acetyl)pyrrolidin-3-yl]carbamic acid, tert-butyl ester 6 (60 mg) in dichloromethane (6 mL). The reaction mixture was stirred at room temperature for 30 min, and then concentrated in vacuo. The residue was dissolved in ethyl acetate, washed with 1M NaOH, (×2), brine, dried ($Na_2SO_4$) and evaporated to dryness. The resultant residue was purified by column chromatography on silica gel, eluting with ethyl acetate/methanol/ammonium hydroxide (90:5:5) to give the title compound (10 mg). $^1$HNMR (300 MHz) ($CDCl_3$) δ 1.6-2.3 (2H, m), 3.15-3.75 (5H, m), 4.40 (2H, m), 6.43 (1H, d, J=16 Hz), 7.02 (2H, d), 7.06 (2H, d), 7.15 (1H, t), 7.25-7.45 (9H, m) and 7.69 (1H, d J=16 Hz).

Examples 2-4 were prepared according to Scheme 2.

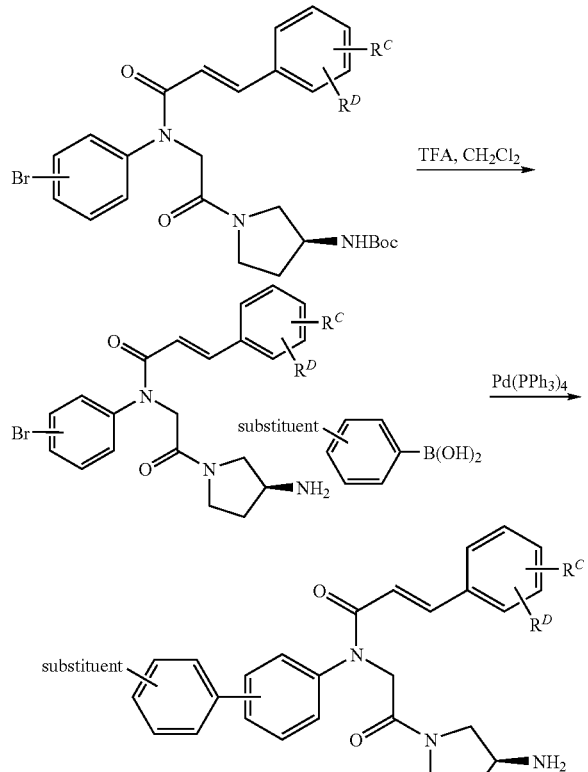

Example 2

Synthesis of (E)-N-[2-((S)-3-Aminopyrrolidin-1-yl)-2-oxo-ethyl]-N-(4-bromophenyl)-3-phenylacrylamide Compound 8

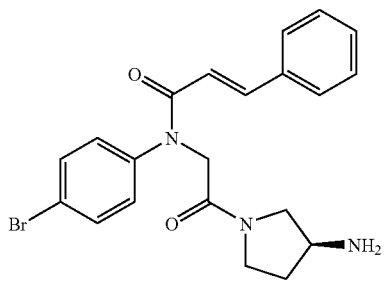

Trifluoroacetic acid (30 mL) was added to a solution of [(S)-1-(2-{(4-bromophenyl)-[(E)-(3-phenylacryloyl)]amino}acetyl)pyrrolidin-3-yl]carbamic acid, tert-butyl ester 3 (4.0 g, 7.57 mmol) in dichloromethane (90 mL). The reaction mixture was stirred at room temperature for 16 h, and then concentrated in vacuo. The residue was dissolved in ethyl acetate, washed with 1M NaOH (×2), brine, dried ($Na_2SO_4$) and evaporated to give the title compound as a foam (2.78 g, 86%). $^1$HNMR (300 MHz) (d6-DMSO) δ 1.5-2.1 (2H, 4×m), 3.08 (1H, m), 3.1-3.6 (4H, m), 4.47, 4.50 (2H, 2×br s), 6.43 (1H, br d), 7.3-7.5 (7H, m), 7.53 (1H, d, J=16 Hz) and 7.65 (2H, d).

Example 3

Synthesis of (E)-N-[2-((S)-3-Aminopyrrolidin-1-yl)-2-oxo-ethyl]-3-phenyl-N-(3'-trifluoromethoxy-biphenyl-4-yl)-acrylamide (OGT4325)

Compound 9

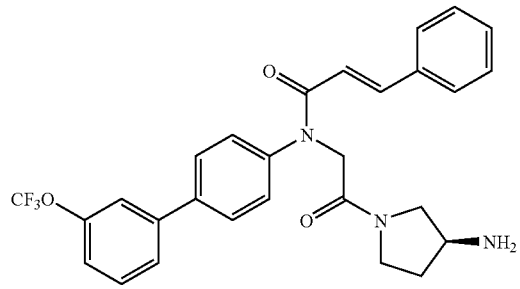

Tetrakis(triphenylphosphine)palladium[0] (20 mg, 5 mol %) was added in one portion to (E)-N-[2-((S)-3-aminopyrrolidin-1-yl)-2-oxo-ethyl]-N-(4-bromo-phenyl)-3-phenylacrylamide 8 (150 mg, 0.353 mmol) and 3-trifluoromethoxyphenylboronic acid (1.5 eq) in dioxane (2 mL) followed by 1M aqueous $Na_2CO_3$ (0.7 mL). The reaction mixture was heated at 150° C. in a microwave reactor for 20 min. It was then diluted with ethyl acetate, washed with 10% NaOH, brine and water and filtered through a pad of celite. The filtrate was dried ($Na_2SO_4$) and evaporated to dryness. The resultant residue was purified by silica gel column chromatography, eluting with dichloromethane/methanol/chloroform (93:5:2), to give the title compound (160 mg, 89%). $^1$HNMR (300 MHz) ($CDCl_3$) δ 1.60-2.25 (2H, m), 3.15-3.40 (1H, m), 3.50-3.80 (4H, m), 4.40-4.65 (2H, m), 6.48 (1H, d, J=16 Hz), 7.20-7.36 (7H, m), 7.45 (1H, br s), 7.49 (1H, d), 7.54 (3H, m), 7.62 (2H, d) and 7.72 (1H, d, J=16 Hz).

Example 4

Synthesis of 4'-{[2-((S)-3-Aminopyrrolidin-1-yl)-2-oxo-ethyl]-[(E)-(3-phenylacryloyl)]-amino}-biphenyl-3-carboxylic acid, ethyl ester (OGT4355)

Compound 10

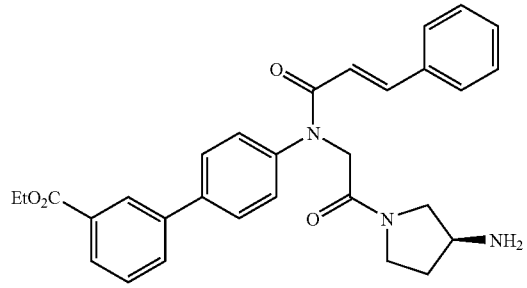

This compound was prepared from (E)-N-[2-((S)-3-aminopyrrolidin-1-yl)-2-oxo-ethyl]-N-(4-bromophenyl)-3-phenylacrylamide (44%) by the same method as described for compound 9. $^1$HNMR (300 MHz) ($CDCl_3$) δ 1.42 (3H, t), 1.65-2.25 (2H, m), 3.20-3.40 (1H, m), 3.50-3.80 (4H, m), 4.42 (2H, q), 4.45-4.65 (2H, m), 6.49 (1H, d, J=16 Hz), 7.25-7.40 (5H, m), 7.50-7.60 (3H, m), 7.67 (2H, d), 7.73 (1H, d, J=16 Hz), 7.80 (1H, d), 8.06 (1H, d) and 8.30 (1H, br s).

Examples 5 and 6 were synthesized according to Scheme 3.

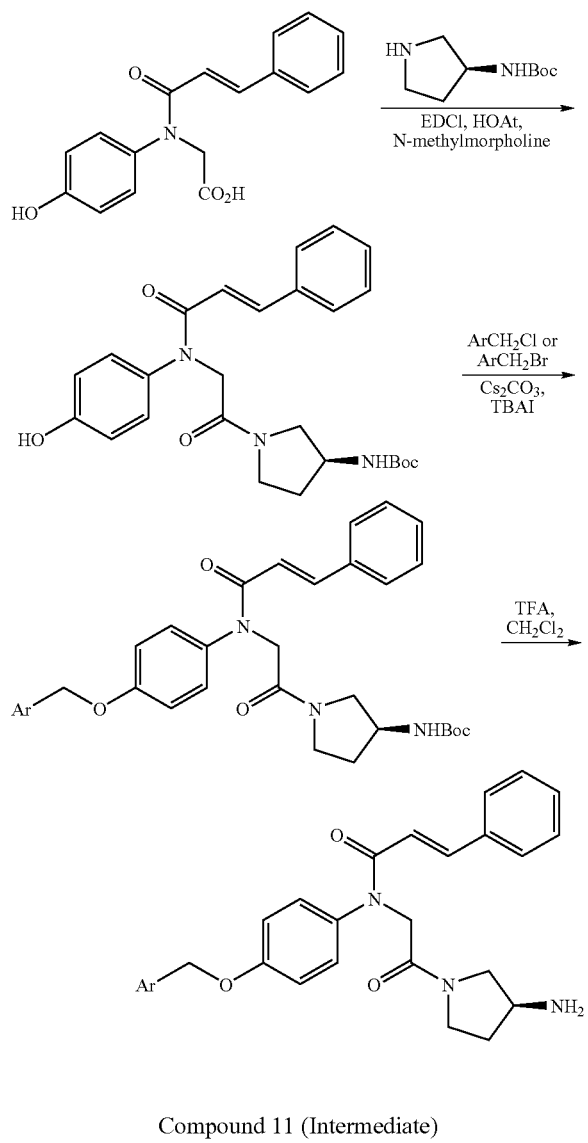

Compound 11 (Intermediate)

(E)-3-Phenylacrylic acid 4-[(E)-(3-phenylacryloyl) amino]phenyl ester

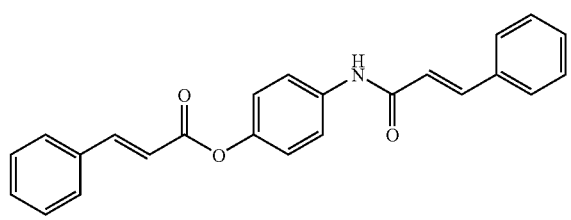

Cinnamoyl chloride (16.79 g, 100.8 mmoL) was added to a solution of 4-aminophenol (5.00 g, 45.8 mmol) and DMAP (0.56 g, 4.58 mmol) in pyridine (5mL). The reaction mixture was stirred at room temperature for 30 min whereupon a solid mass formed. Dichloromethane (50mL) was added and the resultant suspension was stirred at room temperature for 2 h. The reaction mixture was poured into 10% hydrochloric acid/ dichloromethane and shaken. The precipitated white solid was removed by filtration, washed with dichloromethane, 10% hydrochloric acid and then dichloromethane again. The organic layer of the filtrate was separated and washed with 10% hydrochloric acid (×2) and brine, dried (Na$_2$SO$_4$) and evaporated to give the title compound (15.1 g, 89%). $^1$HNMR (300 MHz) (CDCl$_3$) δ 6.55 (1H, d, J=16 Hz), 6.64 (1H, d, J=16 Hz), 7.18 (2H, d), 7.35-7.45 (6H, m), 7.58 (4H, m), 7.67 (2H, m), 7.78 (1H, d, J=16) and 7.88 (1H, d, J=16).

Compound 12 (Intermediate)

(E)-3-Phenylacrylic acid 4-{methoxycarbonylmethyl-[(E)-(3-phenylacryloyl)]-amino}phenyl ester

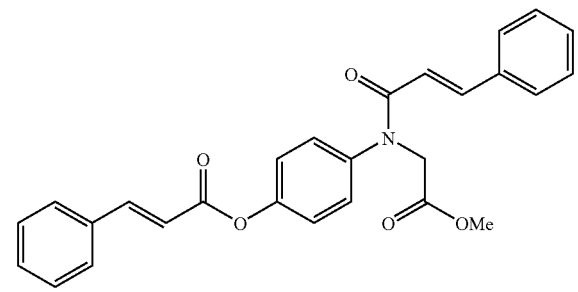

Sodium hydride (60%, 162 mg, 4.06 mmol) was washed with anhydrous THF (×2) and then suspended in anhydrous THF (20 mL). To this was added (E)-3-phenylacrylic acid 4-[(E)-(3-phenylacryloyl)amino]phenyl ester 11 (1.00 g, 2.71 mmol) followed by methyl bromoacetate (0.51 mL, 5.41 mmol). The reaction mixture was stirred at room temperature for 3 days. It was then diluted with ethyl acetate and washed with brine (×3), dried (Na$_2$SO$_4$) and evaporated. The resultant residue was purified by flash column chromatography on silica gel, eluting with petrol/ethyl acetate (2:1→1:1) and then ethyl acetate, to afford the title compound (0.734 g, 61%). $^1$HNMR (300 MHz) (CDCl$_3$) δ 3.77 (3H, s), 4.52 (2H, s), 6.43 (1H, d, J=16 Hz), 6.65 (1H, d, J=16 Hz), 7.25-7.40 (7H, m), 7.45 (4H, m), 7.61 (3H, m), 7.75 (1H, d, J=16 Hz) and 7.91 (1H, d, J=16 Hz).

Compound 13 (Intermediate)

{(4-Hydroxyphenyl)-[(E)-(3-phenylacryloyl)] amino}acetic acid

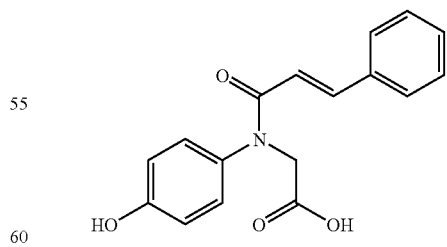

Lithium hydroxide (119 mg, 4.96 mmol) in water (10 mL) was added to a solution of (E)-3-phenylacrylic acid 4-{methoxycarbonylmethyl-[(E)-(3-phenylacryloyl)]-amino}phenyl ester 12 (734 mg, 1.66 mmol) in THF (30 mL) and methanol (10 mL). The reaction mixture was stirred at room temperature for 2 h. A further quantity of lithium hydroxide (119 mg, 4.96 mmol) in water (5 mL) was added and the reaction mixture stirred for a further 1 h. It was then acidified to pH1 with conc. hydrochloric acid and concentrated in vacuo. The aqueous mixture was extracted with ethyl acetate (×2) and the organic layers combined, washed with brine, dried (Na₂SO₄) and evaporated. The resultant residue was purified by flash column chromatography on silica gel, eluting with ethyl acetate, to afford the title compound (0.37 g, 75%). ¹HNMR (300 MHz) (d6-DMSO) δ 4.07 (2H, br s), 6.37 (1H, d, J=15 Hz), 6.78 (2H, d), 7.22 (2H, d), 7.34 (5H, m) and 7.44 (1H, d, J=15 Hz).

Compound 14 (Intermediate)

[(S)-1-(2-{(4-Hydroxyphenyl)-[(E)-(3-phenylacryloyl)]amino}acetyl)pyrrolidin-3-yl]carbamic acid, tert-butyl ester

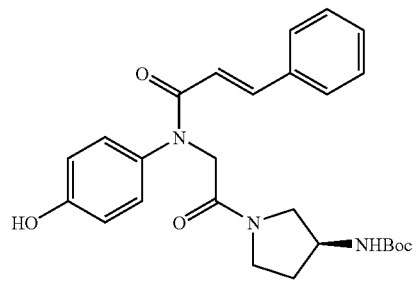

1-Ethyl-3-(3'-dimethylaminopropyl)carbodiimide (0.36 g, 1.87 mmol) was added to a solution of {(4-hydroxyphenyl)-[(E)-(3-phenylacryloyl)]amino}acetic acid 13 (0.37 g, 1.24 mmol), 1-hydroxy-7-azabenzotriazole (0.25 g, 1.87 mmol), (3S)-(−)-3-(tert-butoxycarbonylamino)pyrrolidine (0.35 g, 1.87 mmol) and N-methyl-morpholine (0.27 mL, 2.5 mmol) in DMF (40 mL). The reaction mixture was stirred at room temperature for 3 days and then diluted with ethyl acetate and washed with 10% hydrochloric acid (×2), brine, NaHCO₃ (× 2) and brine, dried (Na₂SO₄) and evaporate. The residue was purified by column chromatography on silica gel, eluting with ethyl acetate/petrol (4:1)→ethyl acetate, to give the title compound as a white powder (0.419 g, 72%). ¹HNMR (300 MHz) (CDCl₃) δ 1.45 (9H, s), 1.8-2.25 (2H, m), 3.4-3.8 (4H, m), 4.15 (1H, m), 4.6 (1H, m), 5.3 (1H, m), 6.43 (1H, d, J=16), 6.87 (2H, d), 7.2-7.32 (7H, m) and 7.65 (1H, d, J=16 Hz).

Compound 15

[(S)-1-(2-{[4-(3,4-Dichlorobenzyloxy)phenyl]-[(E)-(3-phenylacryloyl)]amino}-acetyl)pyrrolidin-3-yl]carbamic acid, tert-butyl ester

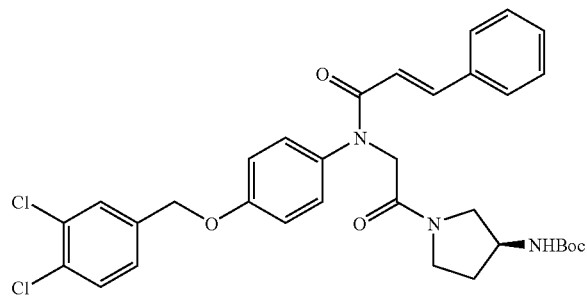

3,4-Dichlorobenzyl chloride (15 µL) was added to a mixture of [(S)-1-(2-{(4-hydroxyphenyl)-[(E)-(3-phenylacryloyl)]amino}acetyl)pyrrolidin-3-yl]carbamic acid, tert-butyl ester 14 (50 mg, 0.11 mmol), cesium carbonate (52 mg, 0.16 mmol) and TBAI (40 mg, 0.11 mmol) in DMF (3 mL). The reaction mixture was stirred at room temperature overnight and then diluted with ethyl acetate and washed with 10% hydrochloric acid (×2) and brine, dried (Na₂SO₄) and evaporated to dryness. The residue was purified by flash column chromatography on silica gel, eluting with ethyl acetate/petrol (2:1), to afford the title compound as a colourless foam (46 mg, 68%). ¹HNMR (300 MHz) (CDCl₃) δ1.41 (9H, s), 1.7-2.2 (2H, m), 3.35-3.8 (4H, m), 4.15-4.35 (2H, m), 4.5 (1H, m), 4.7-4.9 (1H, m), 5.01 (2H, s), 6.35 (1H, d, J=16 Hz), 6.93 (2H, d), 7.2-7.3 (6H, m), 7.37 (2H, d), 7.44 (1H, d), 7.52 (1H, br s) and 7.64 (1H, d, J=16 Hz).

Compound 16

[(S)-1-(2-{[4-(4-Trifluoromethoxybenzyloxy)phenyl]-[(E)-(3-phenylacryloyl)]-amino}acetyl)pyrrolidin-3-yl]carbamic acid, tert-butyl ester

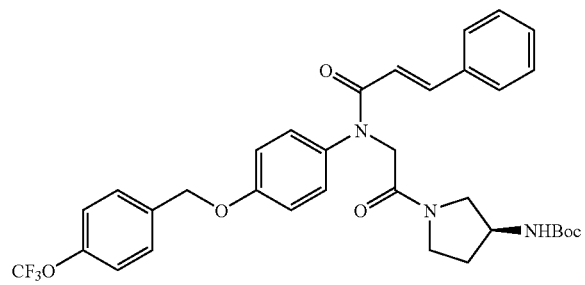

4-Trifluoromethoxybenzyl bromide (17 µL) was added to a mixture of [(S)-1-(2-{(4-hydroxyphenyl)-[(E)-(3-phenylacryloyl)]amino}acetyl)pyrrolidin-3-yl]-carbamic acid, tert-butyl ester 14 (50 mg, 0.11 mmol), cesium carbonate (52 mg, 0.16 mmol) and TBAI (40 mg, 0.11 mmol) in DMF (3 mL). The reaction mixture was stirred at room temperature overnight and then diluted with ethyl acetate and washed with 10% hydrochloric acid (×2) and brine, dried (Na₂SO₄) and evaporated to dryness. The residue was purified by flash column chromatography on silica gel, eluting with ethyl acetate/petrol (2:1) to afford the title compound as a colourless foam (52 mg, 75%). ¹HNMR (300 MHz) (CDCl₃) □ 1.41 (9H, s), 1.7-2.2 (2H, m), 3.35-3.8 (4H, m), 4.15-4.35 (2H, m), 4.5 (1H, m), 4.7-4.9 (1H, m), 5.00 (2H, s), 6.37 (1H, d, J=16 Hz), 6.95 (2H, d), 7.18-7.30 (7H, m), 7.32 (2H, d), 7.45 (2H, d) and 7.64 (1H, d, J=16 Hz).

Example 5

Synthesis of (E)-N-[2-((S)-3-Aminopyrrolidin-1-yl)-2-oxo-ethyl]-N-[4-(3,4-dichloro-benzyloxy)phenyl]-3-phenylacrylamide (OGT4421)

Compound 17

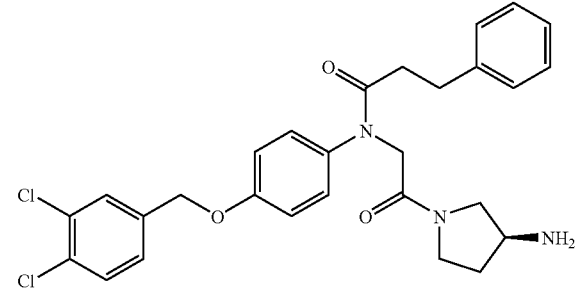

Trifluoroacetic acid (2 mL) was added to a solution of [(S)-1-(2-{[4-(3,4-dichlorobenzyloxy)phenyl]-[(E)-(3-phenylacryloyl)]amino}acetyl)pyrrolidin-3-yl]-carbamic acid, tert-butyl ester 15 (46 mg) in dichloromethane (6 mL). The reaction mixture was stirred at room temperature for 50 min and then concentrated in vacuo. The residue was dissolved in dichloromethane, washed with 1M NaOH (×2), brine, dried (Na₂SO₄) and evaporated to give the title compound as a foam (26 mg, 68%). ¹HNMR (300 MHz) (CDCl₃) δ 1.5-1.8 (1H, m), 1.95-2.2 (1H, m), 3.1-3.3 (1H, m), 3.45-3.75 (4H, m), 4.34 (1H, dd), 4.48 (1H, t), 5.01 (2H, s), 6.36 (1H, d, J=16 Hz), 6.93 (2H, m), 7.20-7.32 (6H, m), 7.38 (2H, d), 7.44 (1H, d), 7.52 (1H, br s) and 7.64 (1H, d, J=16 Hz).

Example 6

Synthesis of (E)-N-[2-((S)-3-Aminopyrrolidin-1-yl)-2-oxo-ethyl]-N-[4-(4-trifluoromethoxy-benzyloxy)phenyl]-3-phenylacrylamide (OGT4420)

Compound 18

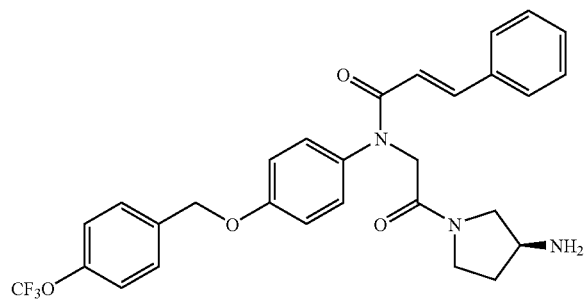

Trifluoroacetic acid (2mL) was added to a solution of [(S)-1-(2-{[4-(4-trifluoromethoxybenzyloxy)phenyl]-[(E)-3-phenylacryloyl)]amino}acetyl)-pyrrolidin-3-yl]carbamic acid, tert-butyl ester 16 (52 mg) in dichloromethane (6 mL). The reaction mixture was stirred at room temperature for 50 min and then concentrated in vacuo. The residue was dissolved in dichloromethane, washed with 1M NaOH (×2), brine, dried (Na₂SO₄) and evaporated to give the title compound as a foam (40 mg, 91%). ¹HNMR (300 MHz) (CDCl₃) δ 1.5-1.8 (1H, m), 1.95-2.2 (1H, m), 3.1-3.3 (1H, m), 3.45-3.75 (4H, m), 4.34 (1H, dd), 4.48 (1H, t), 5.05 (2H, s), 6.37 (1H, d, J=16 Hz), 6.95 (2H, m), 7.18-7.32 (7H, m), 7.38 (2H, d), 7.45 (2H, d) and 7.65 (1H, d, J=16 Hz).

Examples 7, 8 and 9 were synthesized according to Scheme 4.

Scheme 4

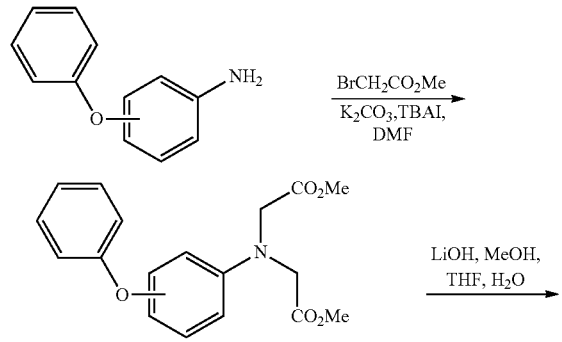

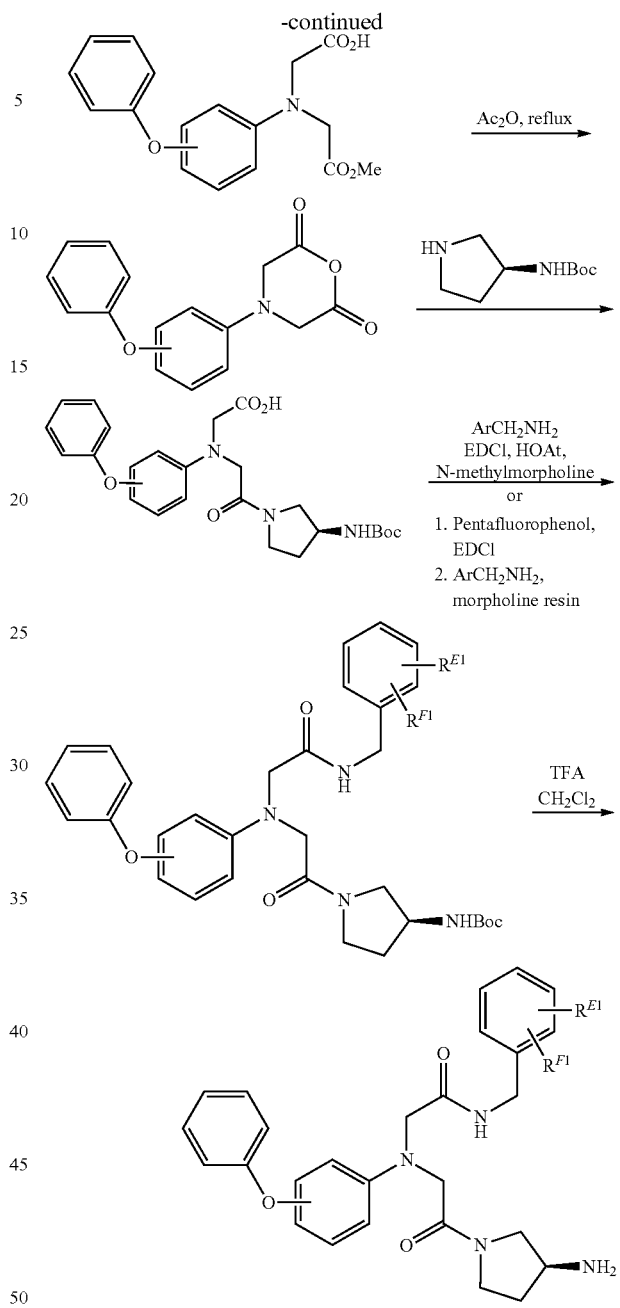

Compound 19 (Intermediate)

[Carboxymethyl-(4-phenoxyphenyl)amino]acetic acid

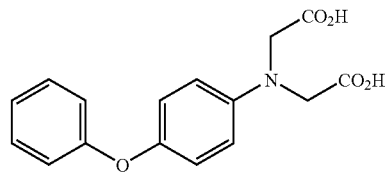

Lithium hydroxide (6.23 g, 0.26 mol) in water (50 mL) was added to a solution of [carboxymethyl-(4-phenoxyphenyl)amino]acetic acid, bis-methyl ester (17.05 g, 0.052 mol) in THF (150 mL) and methanol (50 mL). The reaction mixture was stirred at room temperature for 2 h, acidified to pH 1 with concentrated sulfuric acid and then concentrated in vacuo. The residue was extracted with ethyl acetate and the organic layer washed with 10% hydrochloric acid, brine, dried (Na$_2$SO$_4$) and evaporated to dryness. The crude product was recrystallised from ethyl acetate/petrol to give the title compound as a white solid (11.30 g, 73%). $^1$HNMR (300 MHz) (d6-DMSO) δ 4.10 (4H, s), 6.55 (2H, d), 6.87 (2H, d), 6.92 (2H, d), 7.02 (1H, t) and 7.31 (2H, t).

Compound 20 (Intermediate)

[[2-((S)-3-tert-Butoxycarbonylaminopyrrolidin-1-yl)-2-oxo-ethyl]-(4-phenoxy-phenyl)amino]acetic acid

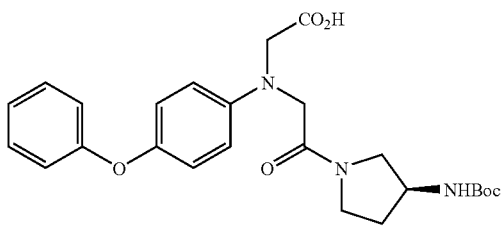

A mixture of [carboxymethyl-(4-phenoxyphenyl)amino] acetic acid 19 (0.5 g, 1.66 mmol) in acetic anhydride (10 mL) was heated to reflux with stirring for 45 minutes. The reaction mixture was cooled to room temperature and poured into saturated aqueous sodium bicarbonate. Solid sodium bicarbonate was added and the mixture stirred until effervescence had ceased. The aqueous mixture was extracted with ethyl acetate (×2) and the organic fractions combined, washed with saturated aqueous sodium bicarbonate, brine, dried (Na$_2$SO$_4$) and evaporated to dryness. The residue was co-evaporated with toluene, dissolved in THF (10 mL) and added to (3S)-(−)-3-(tert-butoxycarbonylamino)pyrrolidine (0.39 g, 2.09 mmol). The reaction mixture was stirred for 3 days and then concentrated in vacuo. The residue was diluted with ethyl acetate and washed with 10% hydrochloric acid (×2), brine, dried (Na$_2$SO$_4$) and evaporated to dryness. The crude product was crystallized from ethyl acetate to give the title compound as a cream powder (0.35 g, 45%). $^1$HNMR (300 MHz) (CDCl$_3$) δ 1.45 (6H, s), 1.55 (3H, s), 1.8-2.4 (2H, m), 3.4-3.9 (5H, m), 4.05-4.75 (4H, m), 6.48 (2H, m), 6.90-7.07 (5H, m) and 7.18 (2H, t).

Example 7

Synthesis of 2-[[2-((S)-3-Aminopyrrolidin-1-yl)-2-oxo-ethyl]-(4-phenoxyphenyl)amino]-N-(3-chlorobenzyl)acetamide (OGT4154))

Compound 12

((S)-1-{2-[[(3-Chlorobenzylcarbamoyl)methyl]-(4-phenoxyphenyl)amino]-acetyl}pyrrolidin-3-yl)-carbamic acid, tert-butyl ester

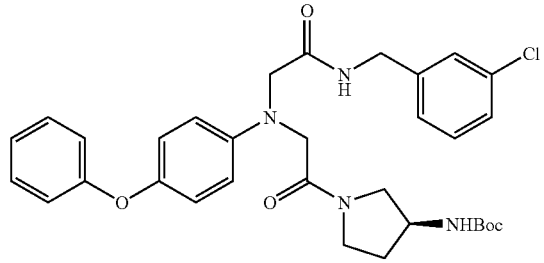

1-Ethyl-3-(3'-dimethylaminopropyl)carbodiimide (144 mg, 0.75 mmol) was added to a solution of [[2-((S)-3-tert-butoxycarbonylaminopyrrolidin-1-yl)-2-oxo-ethyl]-(4-phenoxyphenyl)amino]acetic acid 20 (176 mg, 0.37 mmol), 1-hydroxy-7-azabenzotriazole (103 mg, 0.76 mmol), 3-chlorobenzylamine (0.092 mL, 0.76 mmol) and N-methylmorpholine (0.11 mL, 1.02 mmol) in DMF (5 mL). The reaction mixture was stirred overnight at room temperature and then diluted with ethyl acetate and washed with 10% hydrochloric acid (×2), brine, saturated aqueous sodium bicarbonate (×2) and then brine, dried (Na$_2$SO$_4$) and evaporated onto silica gel. Flash column chromatography, using ethyl acetate as the eluent, gave the title compound as a hard foam (159 mg, 71%). $^1$HNMR (300 MHz) (CDCl$_3$) δ 1.45 (6H, s), 1.55 (3H, s), 1.8-2.4 (2H, m), 3.35-3.90 (5H, m), 3.95-4.40 (4H, m), 4.55-4.70 (2H, m), 6.48 (2H, m), 6.75-7.05 (6H, m), 7.12 (3H, m), 7.25 (2H, m), and 9.81 (1H, m).

Compound 22

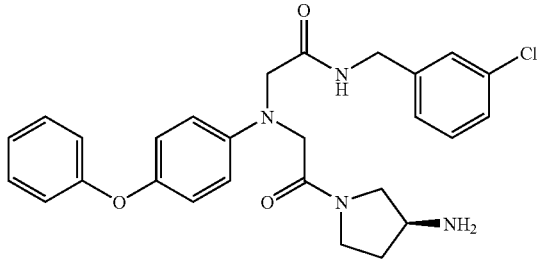

Trifluoroacetic acid (3 mL) was added to a solution of ((S)-1-{2-[[(3-chloro-benzylcarbamoyl)methyl]-(4-phenoxyphenyl)amino]acetyl}-pyrrolidin-3-yl)-carbamic acid, tert-butyl ester 21 (70 mg, 0.1 mmol) in dichloromethane (9 mL). The reaction mixture was stirred at room temperature for 45 min, and then concentrated in vacuo. The residue was dissolved in ethyl acetate, washed with 1M NaOH (×2), brine, dried (Na$_2$SO$_4$) and evaporated. Evaporation of the resultant residue from dichloromethane gave the title compound as a hard foam (74 mg, 64%). $^1$HNMR (300 MHz) (d6-DMSO) δ 1.5-2.1 (2H, m), 3.0-3.7 (5H, m), 4.05 (2H, br s), 4.25-4.40 (4H, m), 6.47 (2H, m), 6.85 (2H, d), 6.93 (2H, d), 7.02 (1H, t), 7.06-7.13 (1H, m), 7.17 (1H, br s), 7.20-7.25 (2H, m), 7.25-7.35 (2H, m) and 9.95 (1H, m).

Example 8

Synthesis of 2-[[2-((S)-3-Aminopyrrolidin-1-yl)-2-oxo-ethyl]-(4-phenoxyphenyl)amino]-N-[3-fluoro-5-(trifluoromethyl)benzyl]acetamide (OGT4155)

Compound 23

((S)-1-{2-[[(3-Fluoro-5-(trifluoromethyl)benzylcarbamoyl)methyl]-(4-phenoxy-phenyl)amino]acetyl}-pyrrolidin-3-yl)-carbamic acid, tert-butyl ester

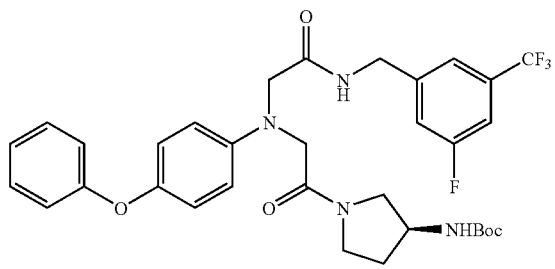

1-Ethyl-3-(3'-dimethylaminopropyl)carbodiimide (144 mg, 0.75 mmol) was added to a solution of [[2-((S)-3-butoxycarbonylaminopyrrolidin-1-yl)-2-oxo-ethyl]-(4-phenoxyphenyl)amino]acetic acid 20 (176 mg, 0.38 mmol), 1-hydroxy-7-azabenzotriazole (103 mg, 0.76 mmol), 3-fluoro-5-(trifluoromethyl)benzylamine (0.11 mL, 0.75 mmol) and N-methylmorpholine (0.11 mL, 1.02 mmol) in DMF (5 mL). The reaction mixture was stirred overnight at room temperature and then diluted with ethyl acetate and washed with 10% hydrochloric acid (×2), brine, saturated aqueous sodium bicarbonate (×2) and brine, dried (Na$_2$SO$_4$) and evaporated onto silica gel. Flash column chromatography, using ethyl acetate as the eluent gave the title compound as a hard foam (82 mg, 34%). $^1$HNMR (300 MHz) (CDCl$_3$) δ 1.45 (6H, s), 1.55 (3H, s), 1.75-2.40 (2H, m), 3.37-3.93 (5H, m), 3.95-4.40 (4H, m), 4.50-4.70 (2H, m), 6.46 (2H, m), 6.94 (4H, m), 7.03 (2H, m), 7.08 (1H, m), 7.30 (3H, m) and 10.06 (1H, m).

Compound 24

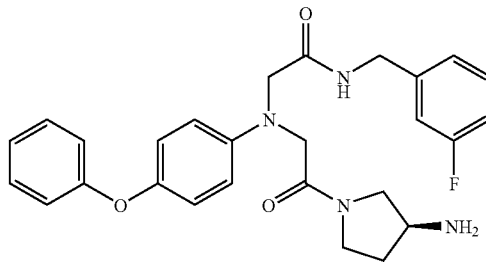

Trifluoroacetic acid (3 mL) was added to a solution of ((S)-1-{2-[[(3-fluoro-5-(trifluoromethyl)benzylcarbamoyl)methyl]-(4-phenoxy-phenyl)amino]acetyl}-pyrrolidin-3-yl)-carbamic acid, tert-butyl ester 23 (70 mg, 0.1 mmol) in dichloromethane (9 mL). The reaction mixture was stirred at room temperature for 45 min, and then concentrated in vacuo. The residue was dissolved in ethyl acetate, washed with 1M NaOH (×2), brine, dried (Na$_2$SO$_4$) and evaporated to dryness. The resultant residue was then evaporated from dichloromethane to give the title compound as a hard foam (48 mg, 81%). $^1$HNMR (300 MHz) (d6-DMSO) δ 1.5-2.1 (2H, m), 3.0-3.7 (5H, m), 4.07 (2H, br s), 4.30-4.50 (4H, m), 6.48 (2H, m), 6.80-6.95 (4H, m), 7.02 (1H, t), 7.20-7.35 (3H, m), 7.40 (1H, s), 7.48 (1H, d) and 10.06 (1H, m).

Example 9

Synthesis of 2-[[2-((S)-3-Aminopyrrolidin-1-yl)-2-oxo-ethyl]-(3-phenoxyphenyl)amino]-N-[3,5-bis-(trifluoromethyl)benzyl]acetamide (OGT4165)

Compound 25 (Intermediate)

[Carboxymethyl-(3-phenoxyphenyl)amino]acetic acid

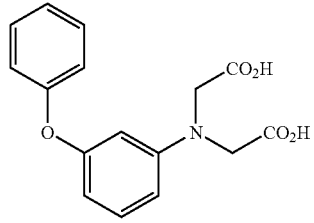

Lithium hydroxide (4.06 g, 170 mmol) in water (50 mL) was added to a solution of [carboxymethyl-(3-phenoxyphenyl)amino]acetic acid, bis-methyl ester (11.18 g, 33.95 mmol) in THF (150 mL) and methanol (50 mL). The reaction mixture was stirred at room temperature for 1 h, acidified to pH 1 with concentrated sulfuric acid and then concentrated in vacuo. The residue was extracted with ethyl acetate and the organic layer washed with 10% hydrochloric acid, brine, dried (Na$_2$SO$_4$) and evaporated to dryness. The crude product was recrystallised from ethyl acetate/petrol to give the title compound as a white solid (9.98 g, 97%). $^1$HNMR (300 MHz) (d6-DMSO) δ 6.18 (1H, br s), 4.08 (4H, s), 6.24 (1H, dd), 6.30 (1H, dd), 6.97 (2H, d), 7.10 (1H, t), 7.15 (1H, t), 7.36 (2H, t) and 12.7 (1H, br s).

Compound 26 (Intermediate)

4-(3-Phenoxyphenyl)morpholine-2,6-dione

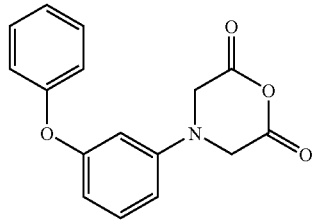

[Carboxymethyl-(3-phenoxyphenyl)amino]acetic acid 25 (5 g) was heated at reflux in acetic anhydride (30 mL) for 1 h. The cooled reaction mixture was poured into saturated aqueous sodium bicarbonate and extracted with ethyl acetate. The organic layer was washed several times with saturated aqueous sodium bicarbonate (until no further effervescence was observed) and twice with brine. The organic phase was dried (Na$_2$SO$_4$) and concentrated in vacuo to give the title compound as a golden oil (4.7 g, 100%). $^1$HNMR (300 MHz) (CDCl$_3$) δ 6.10 (1H, m), 6.67 (2H, br d), 7.03 (2H, d), 7.17 (1H, t), 7.30 (1H, t) and 7.39 (2H, t).

Compound 27 (Intermediate)

[[2-((S)-3-tert-Butoxycarbonylaminopyrrolidin-1-yl)-2-oxo-ethyl]-(3-phenoxy-phenyl)amino]acetic acid

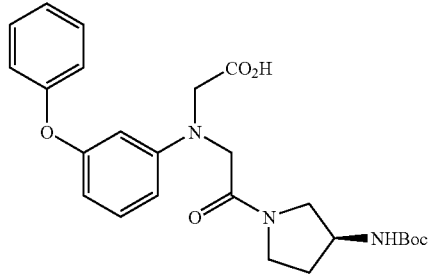

To a solution of 4-(3-phenoxyphenyl)morpholine-2,6-dione 26 (4.7 g, 0.0166 mol) in THF (50 mL) was added (3S)-(−)-3-(tert-butoxycarbonylamino)pyrrolidine (4.11 g, 0.0221 mol). The reaction mixture was stirred for 3 days after which time a precipitate had formed. This material was collected by filtration, then washed with ethyl acetate to give the first crop of the title compound. A further crop was obtained by evaporating the filtrate in vacuo. The resultant residue was dissolved in ethyl acetate, washed with 10% hydrochloric acid and brine, dried (Na$_2$SO$_4$) and concentrated in vacuo. The second crop of title compound which precipitated was collected by filtration to give a total yield of 4.36 g (50%), as a cream solid. ¹HNMR (300 MHz) (d6-DMSO, 100° C.)) δ 1.43 (9H, s), 1.75-2.20 (2H, 2×m), 2.75-3.1 (1H, br), (1H, br), 3.20-3.75 (4H, m), 4.09 (2H, s), 4.21 (2H, s), 6.22 (1H, br s), 6.37 2H, br t), 6.70 (1H, br), 6.99 (2H, d), 7.14 (2H, m) and 7.37 (2H, br t).

Compound 28 (Intermediate)

[[2-((S)-3-tert-Butoxycarbonylaminopyrrolidin-1-yl)-2-oxo-ethyl]-(3-phenoxy-phenyl)amino]acetic acid, pentafluorophenyl ester

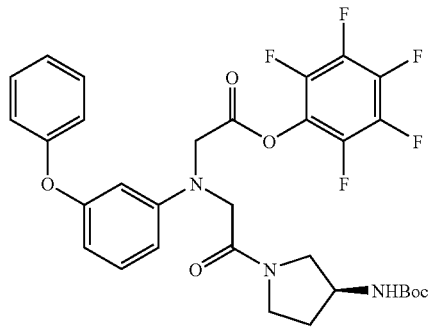

To a solution of [[2-((S)-3-tert-butoxycarbonylaminopyrrolidin-1-yl)-2-oxo-ethyl]-(3-phenoxyphenyl)amino]acetic acid 27 (4.36 g, 9.39 mmol) in DMF (30 mL) were added pentafluorophenol (1.88 g, 10.21 mmol) and 1-ethyl-3-(3'-dimethylaminopropyl)-carbodiimide (1.96 g, 10.22 mmol). The reaction mixture was stirred overnight at room temperature. It was then diluted with ethyl acetate, washed with 10% hydrochloric acid (×2), brine (×2), dried (Na₂SO₄) and concentrated in vacuo. The resultant solid was evaporated twice from diethyl ether to give the title compound as a colourless, glassy solid (3.4 g, 57%) which was used directly in the next step.

Compound 29

((S)-1-{2-[[(3,5-bis-(Trifluoromethyl)benzylcarbamoyl)methyl]-(3-phenoxy-phenyl)amino]acetyl}-pyrrolidinyl-3-yl)-carbamic acid, tert-butyl ester

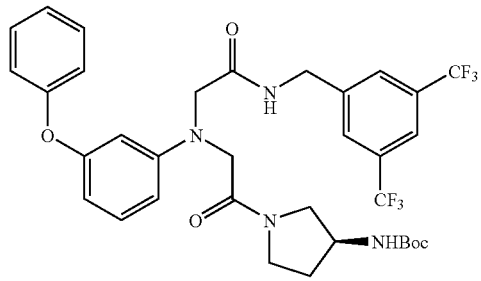

[[2-((S)-3-tert-Butoxycarbonylaminopyrrolidin-1-yl)-2-oxo-ethyl]-(3-phenoxy-phenyl)amino]acetic acid, pentafluorophenyl ester 28 (200 mg, 0.32 mmol), 3,5-bis-(trifluoromethyl)benzylamine (115 mg, 0.47 mmol) and morpholine resin (190 mg, 2.5 mmol/g, 1.5 eq) in dichloromethane (5 mL) were stirred at room temperature for 2 h. Isocyanate resin (1.5 eq) was then added to remove residual amine and the reaction mixture was filtered. The filtrate was purified by silica gel chromatography, using ethyl acetate/hexane (1:1) as eluent, to remove impurities followed by methanol to provide the title compound which was used directly in the next step.

Compound 30

2-[[2-((S)-3-Aminopyrrolidin-1-yl)-2-oxo-ethyl]-(3-phenoxyphenyl)amino]-N-[3,5-bis-(trifluoromethyl)benzyl]acetamide (OGT4165)

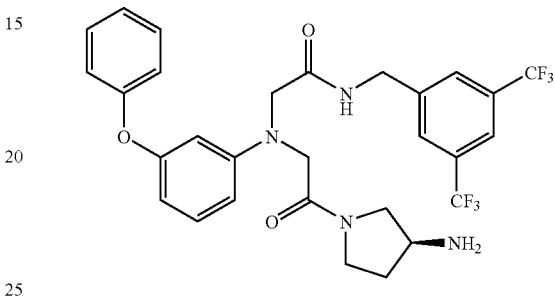

This compound was prepared from ((S)-1-{2-[[(3,5-bis-(trifluoromethyl)benzyl-carbamoyl)methyl]-(3-phenoxyphenyl)amino]acetyl}pyrrolidin-3-yl)-carbamic acid, tert-butyl ester 29 by the same method as described for compound 24. ¹HNMR (300 MHz) (d6-DMSO) δ 1.5-2.1 (2H, m), 3.0-3.6 (5H, m), 4.05 (2H, m), 4.35 (2H, m), 4.50 (2H, m), 6.10 (1H, m), 6.24 (2H, m), 6.93 (2H, d), 7.13 (2H, m), 7.34 (2H, t), 7.85 (2H, s), 7.94 (1H, s) and 10.08 (1H, m).

Example 10

Compounds of the present invention can be made according to the following scheme:

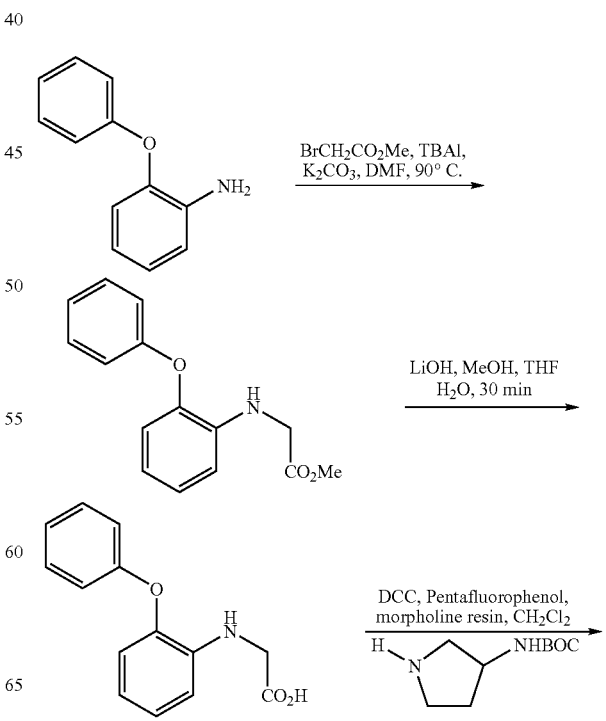

-continued

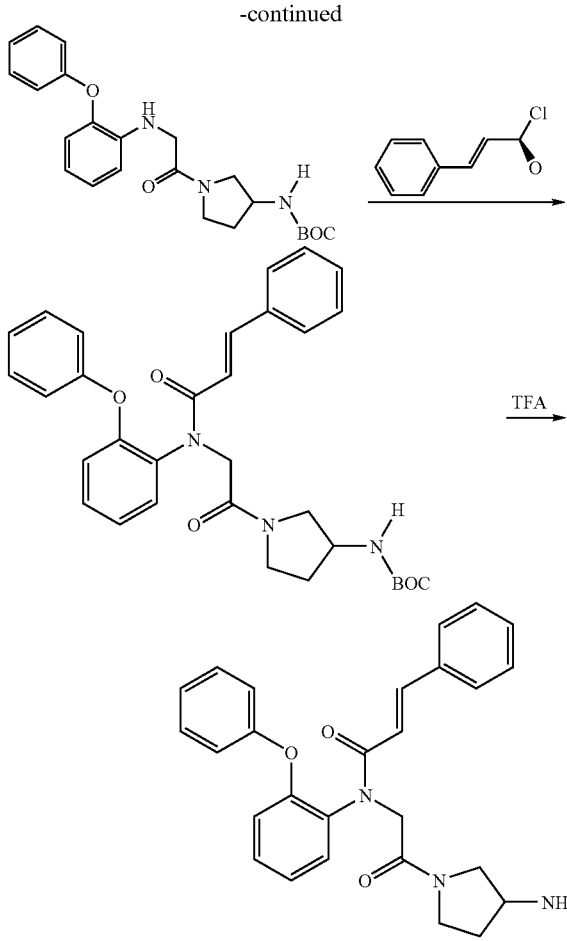

STEP 1: 2-Phenoxyaniline is heated with a slight excess of methyl bromoacetate in DMF solvent in the presence of an excess of potassium carbonate and a catalytic amount of tetrabutylammonium iodide. Upon complete consumption of the starting material, the reaction mixture is subjected to an aqueous workup and product ester isolated by standard methods.

STEP 2: Hydrolysis of the ester is performed by treatment with one equivalent of LiOH in MeOH:THF:water/:1:1:1 and heating the mixture to reflux until starting material is consumed. Treatment with one equivalent of HCl followed by concentration affords the acid.

STEP 3: The acid is activated with a slight excess of DCC and a slight excess of pentafluorophenol in methylene chloride solvent and the resulting pentafluorophenyl ester is treated with BOC-protected 3-aminopyrrolidine. Upon complete consumption of the starting material the reaction mixture is subject to a basic pH aqueous workup and the product amide isolated by standard methods.

STEP 4: The aniline is treated with an excess of cinnamoyl chloride, HOBT and triethylamine in DCE and heated until starting material has been consumed. At this time the reaction mixture is subject to aqueous workup and the product isolated by standard means to afford the product amide.

STEP 5: The protected amine is treated with 0.1 equivalents of trifluoroacetic acid in methylene chloride. Upon consumption of the starting material the reaction mixture is poured into aqueous dilute NaOH and isolated by standard methods to provide the desired amine.

Example 11

Compounds of the present invention can be made according to the following scheme:

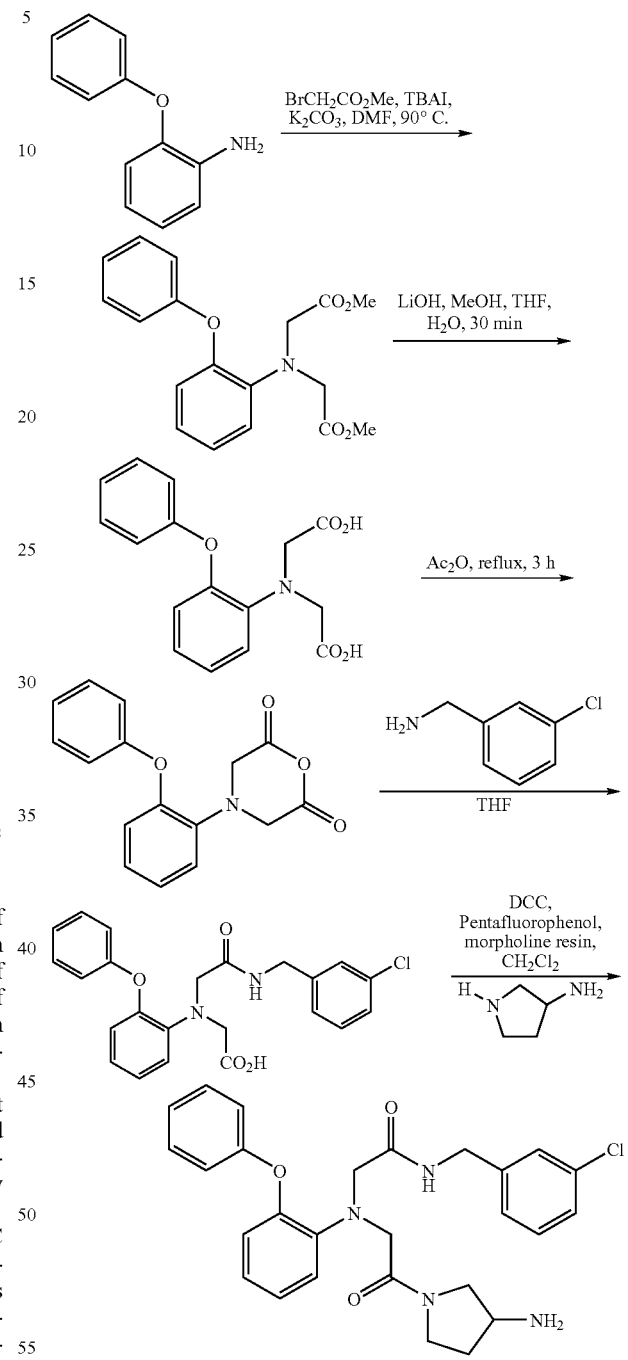

STEP 1: Commercially available 2-phenoxyaniline is heated with a large excess of methyl bromoacetate in DMF solvent in the presence of an excess of potassium carbonate and a catalytic amount of tetrabutylammonium iodide. Upon complete consumption of the starting material, the reaction mixture is cooled to rt, concentrated to a thick slurry, the residue subjected to an aqueous workup and the product ester isolated by standard methods.

STEP 2: Hydrolysis of the ester is performed by treatment with two equivalents of LiOH in MeOH:THF:water/1:1:1 and heating the mixture to reflux until starting material is consumed. Treatment with two equivalents of HCl followed by concentration affords the diacid.

STEP 3: The diacid is dissolved in 20 equivalents of acetic anhydride and heated to reflux for 3h. After reaction mixture is cooled to rt and concentrated to dryness on a hi-vacuum rotary evaporator. The reside is taken directly into the next step.

STEP 4: The cyclic anhydride is dissolved in THF and a slight excess of 3-chlorobenzylamine is added. Upon consumption of the starting material, the reaction mixture is poured onto dilute aqueous HCl and extracted with methylene chloride. The organic extracts are dried and concentration to provide the acid-amide.

STEP 5: The acid-amide is activated with a slight excess of DCC and a slight excess of pentafluorophenol in methylene chloride solvent and the resulting pentafluorophenyl ester is treated with 3-aminopyrrolidine. Upon complete consumption of the starting material the reaction mixture is subject to a basic pH aqueous workup and the product isolated by standard methods.

Example 12

Additional examples can be prepared by substituting the BOC-protected 3-aminopyrrolidine employed in any of the above examples with a suitably protected amine derived from the building blocks shown below:

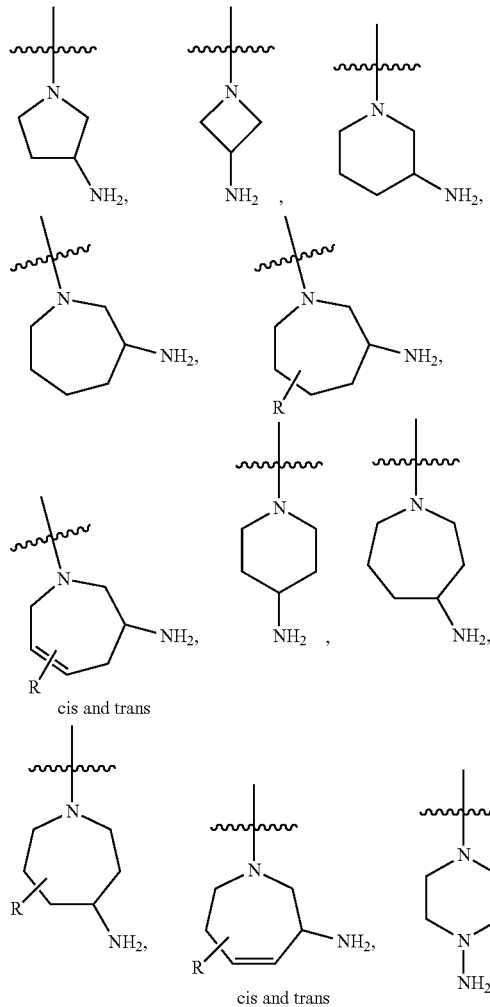

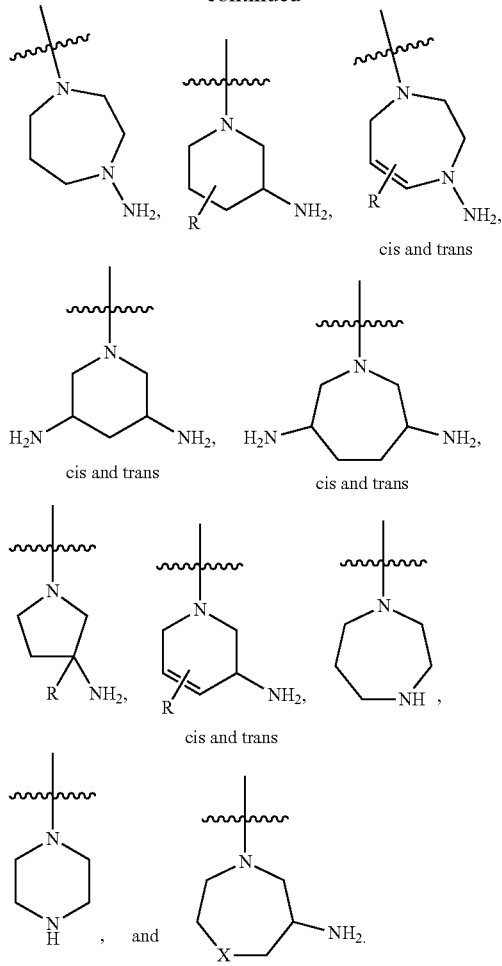

Example 13

Additional examples can be prepared by substituting the cinnamoyl chloride employed in any of the above examples with a suitable acid chloride derived from the simple esters prepared as shown below:

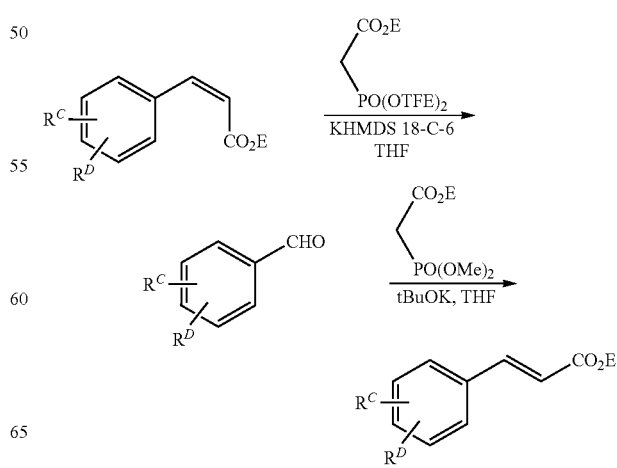

85

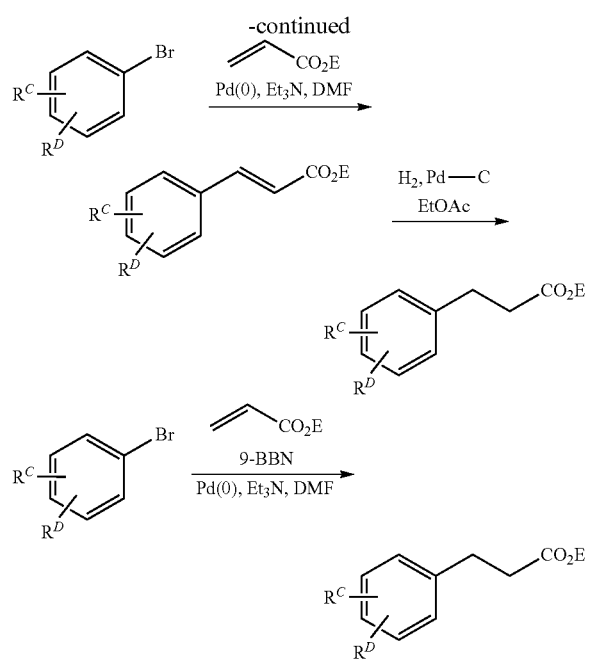

E = Me or t-Bu

Example 14

Additional examples can be prepared by replacing the diphenyl ether illustrated in Schemes 1 and 4 with a substituted diphenyl ether aniline wherein the diphenyl ether moiety is constructed via the procedure of Buck (Organic Syntheses (2005), Vol. 82, p. 69).

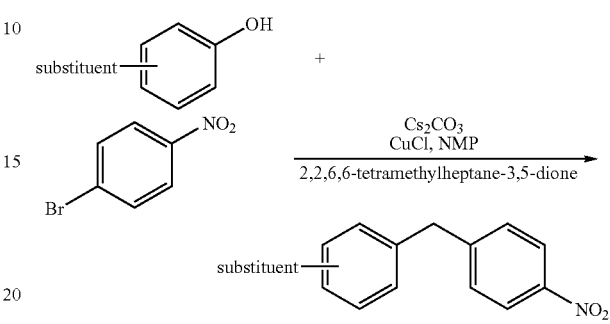

Example 15

The following compounds are synthesized by methods described herein or known in the art using the appropriate starting materials, reagents, intermediates and protecting groups, when necessary.

15A

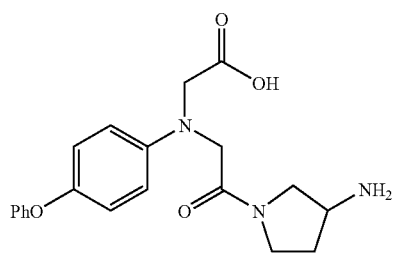

15B

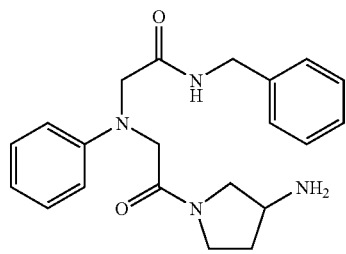

15C

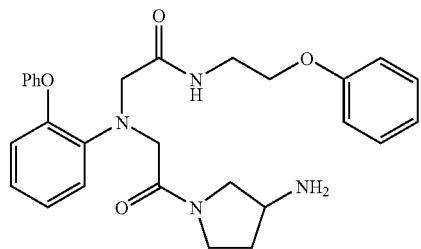

-continued
| | |
|---|---|
| 15D | 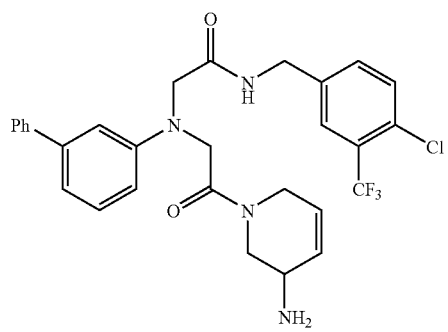 |
| 15E | 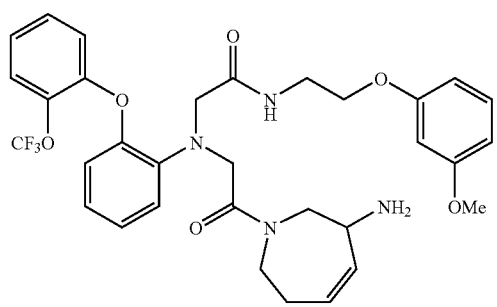 |
| 21F | 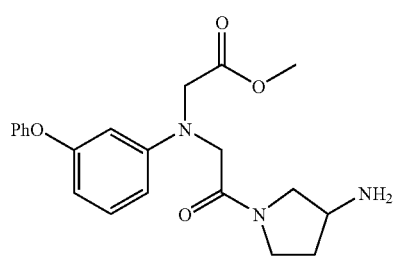 |
| 15G | 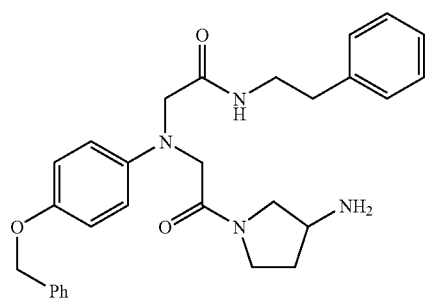 |
| 15H | 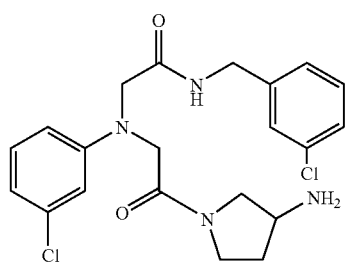 |

15I 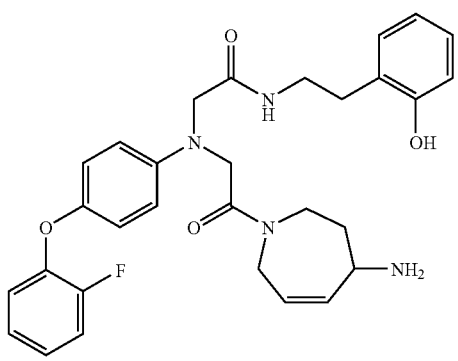
15J 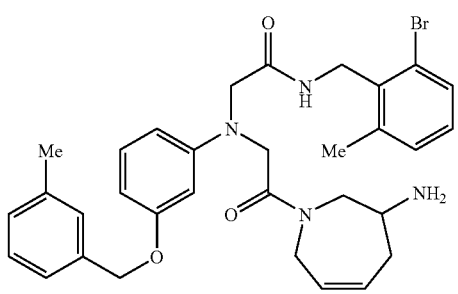
15K 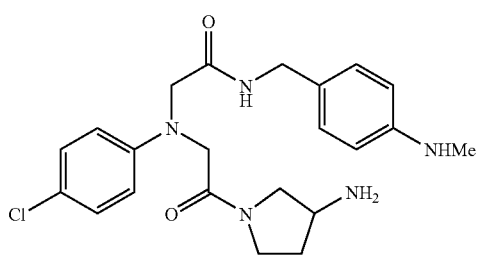
15L 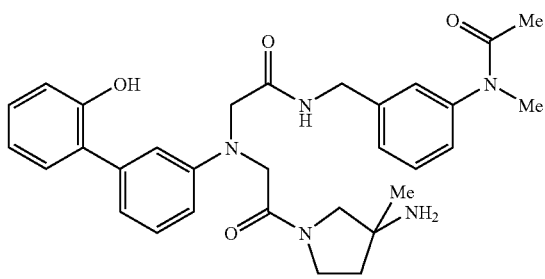
15M 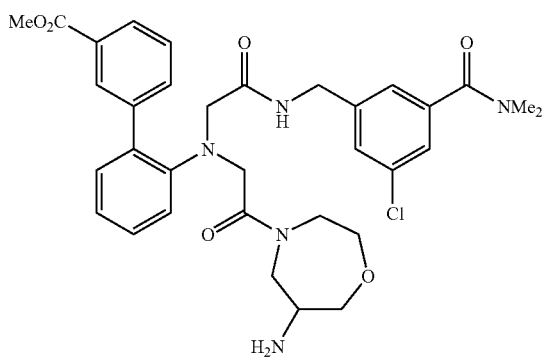

-continued
15N 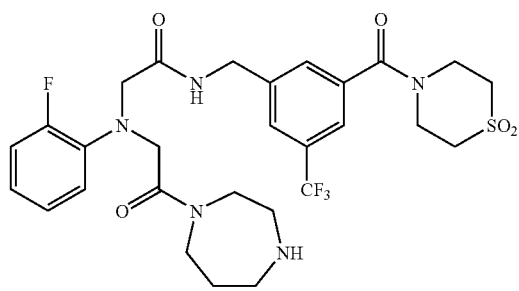
15O 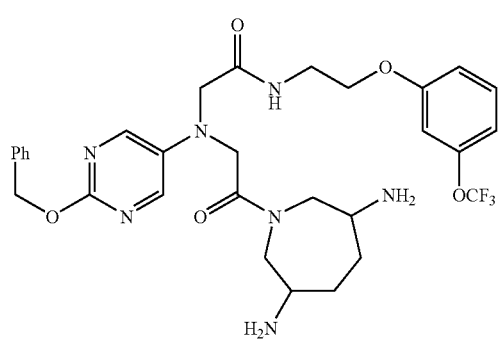
15P 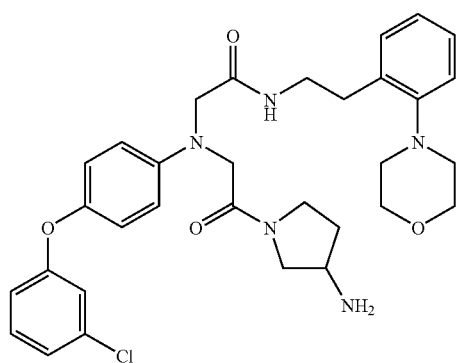
15Q 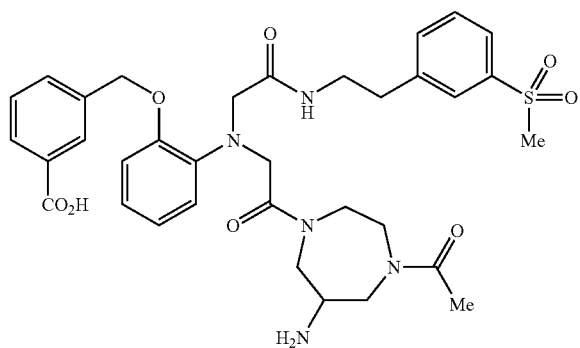

-continued
15R 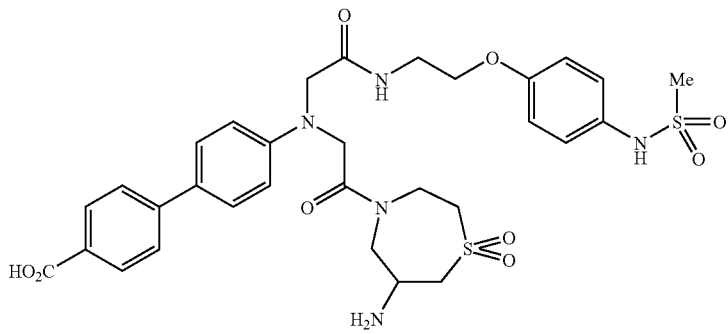
15S 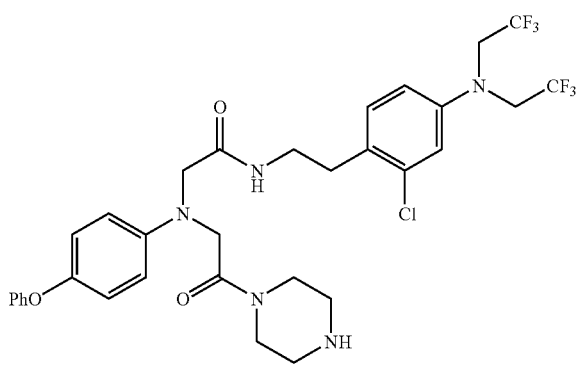
15T 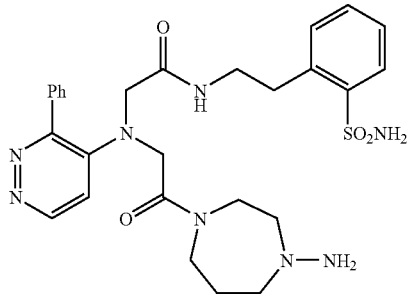
15U 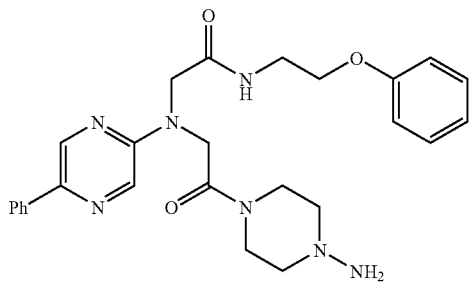
15V 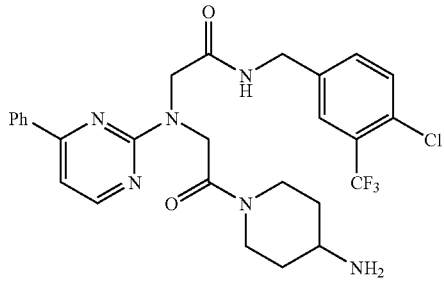

-continued
| | |
|---|---|
| 15W | 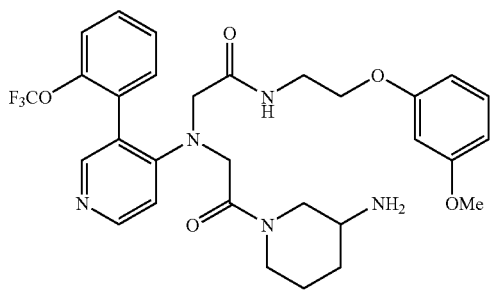 |
| 15X | 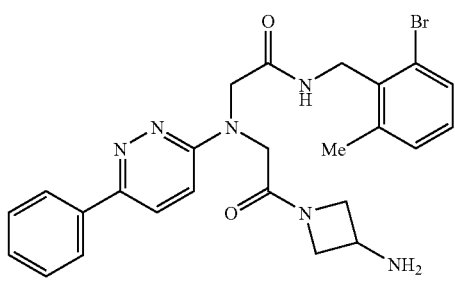 |
| 15Y | 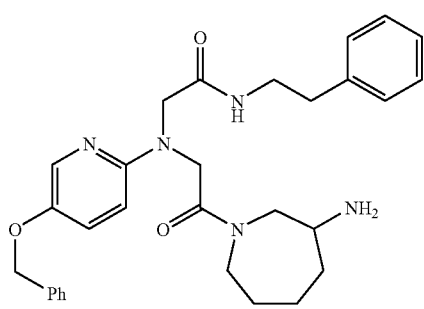 |
| 15Z | 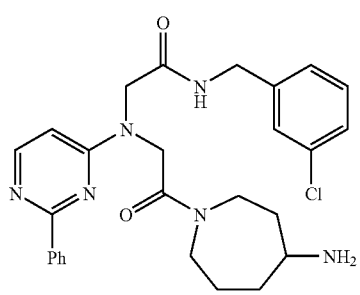 |
| 15AA | 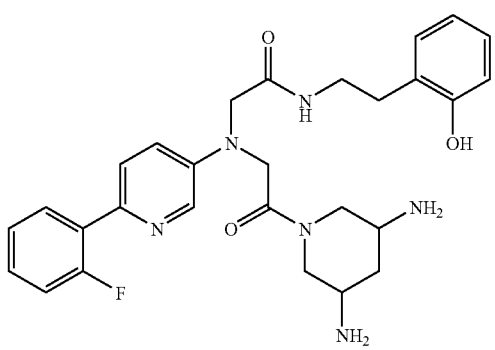 |

Example 16
The following compounds are synthesized by methods described herein or known in the art using the appropriate starting materials, reagents, intermediates and protecting groups, when necessary.
16A 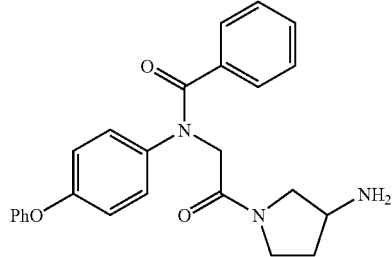
16B 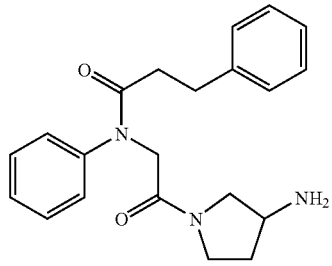
16C 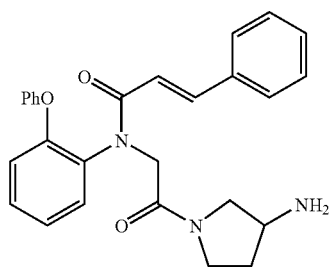
16D 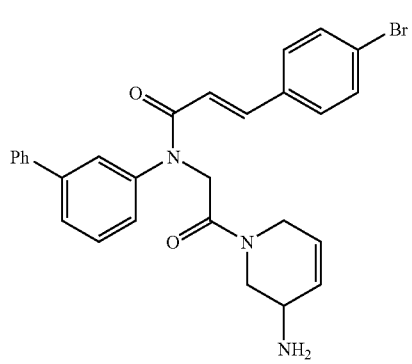
16E 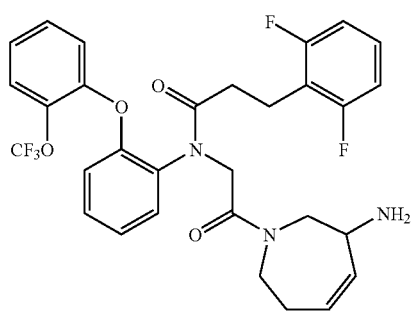
16F 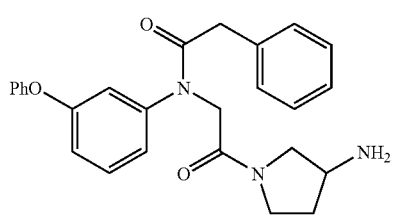
16G 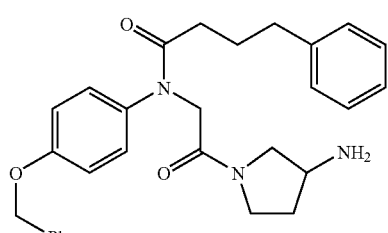
16H 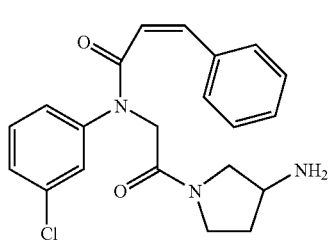
16I 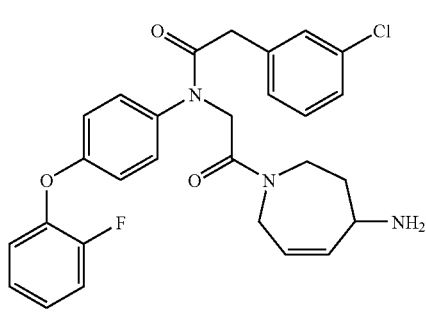
16J 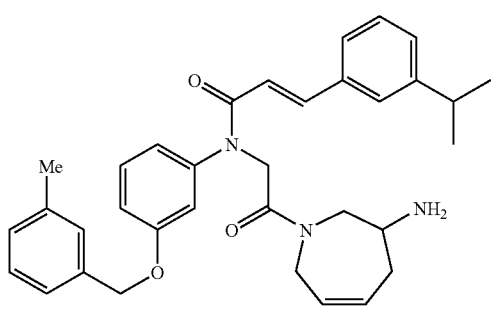
16K 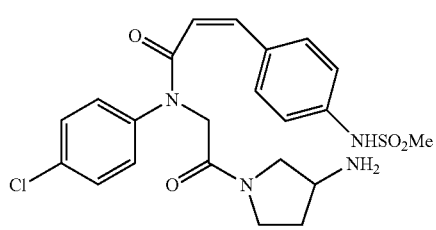

-continued
16L 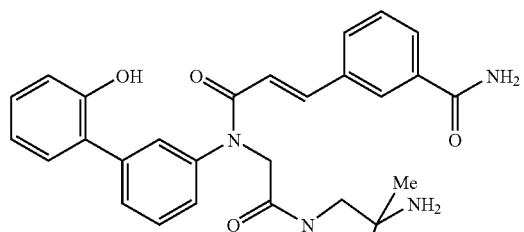
16M 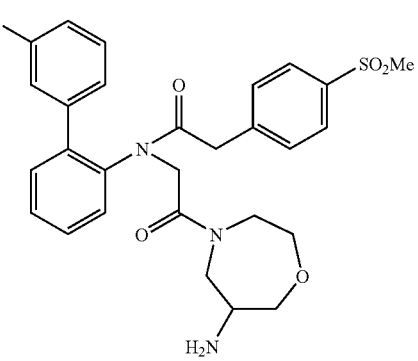
16N 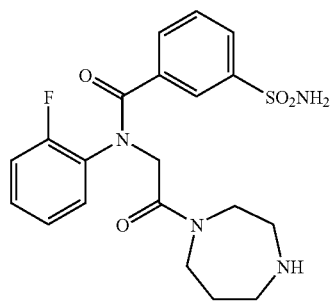
16O 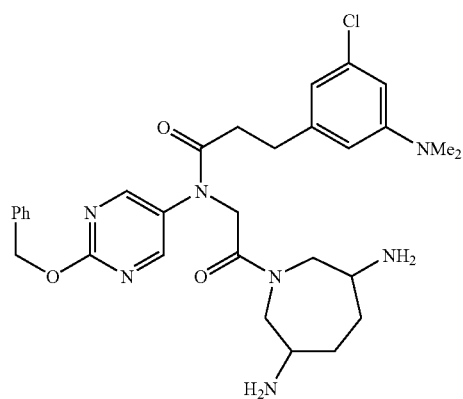
-continued
16P 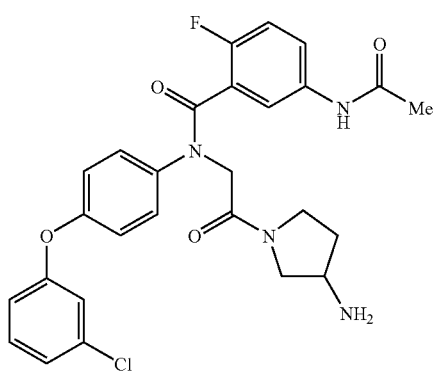
16Q 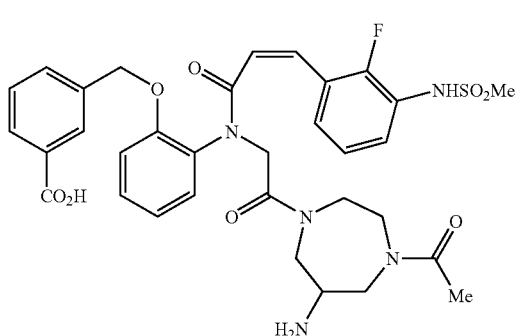
16R 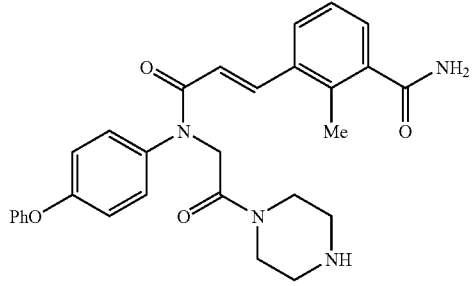
16S 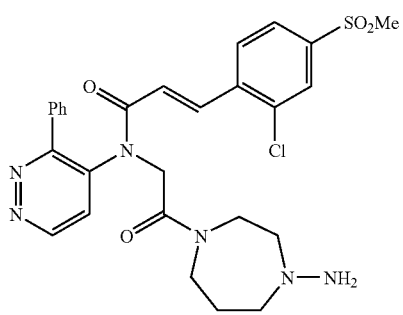
16T 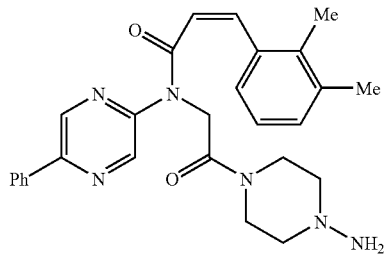

| 16U | 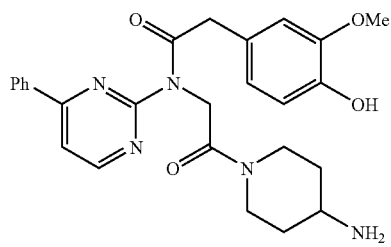 |
| --- | --- |
| 16V | 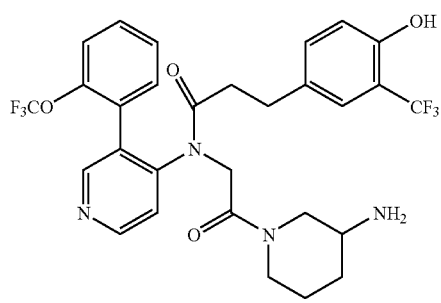 |
| 16W | 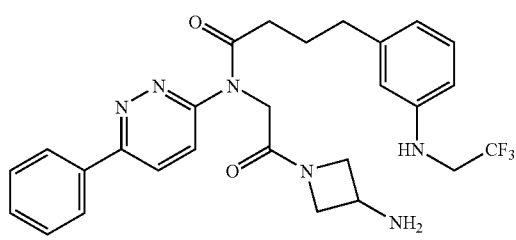 |
| 16X | 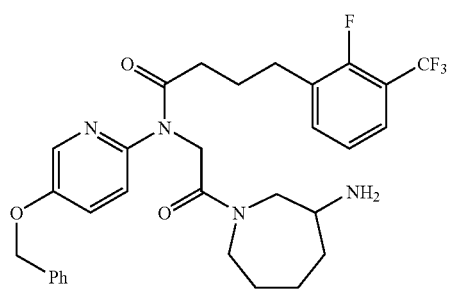 |
| 16Y | 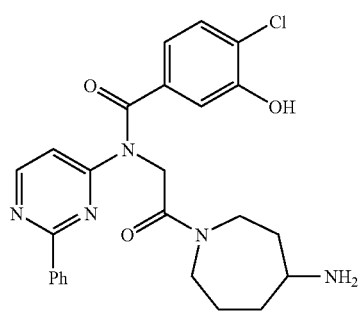 |
| 16Z | 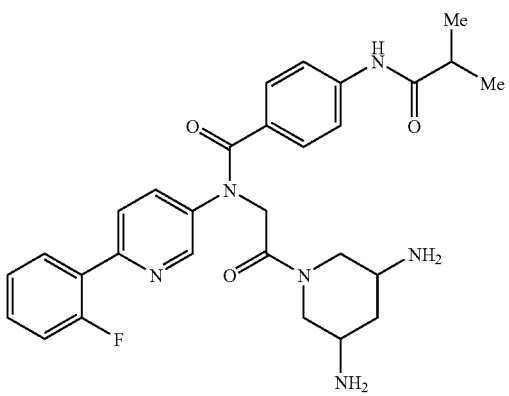 |
| --- | --- |
Example 17
The following compounds were synthesized by methods described herein or known in the art using the appropriate starting materials, reagents, intermediates and protecting groups, when necessary.
| 17A | 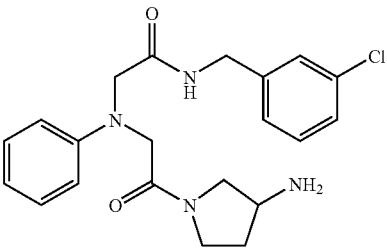 |
| --- | --- |
| 17B | 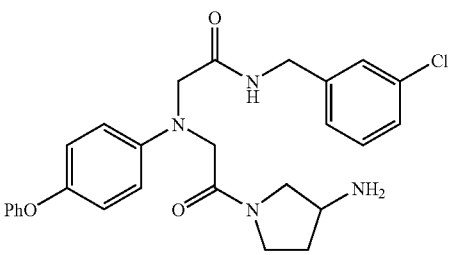 |
| 17C | 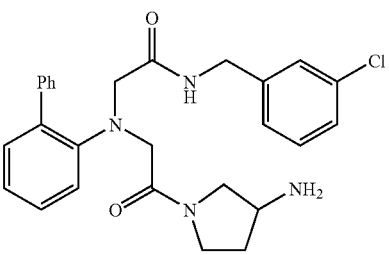 |

-continued
17D 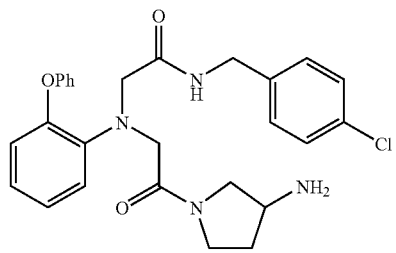
17E 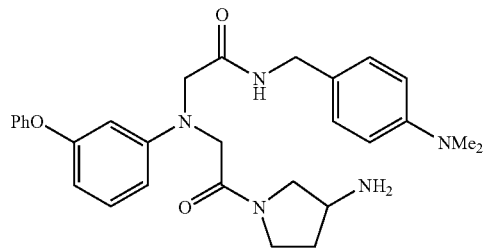
17F 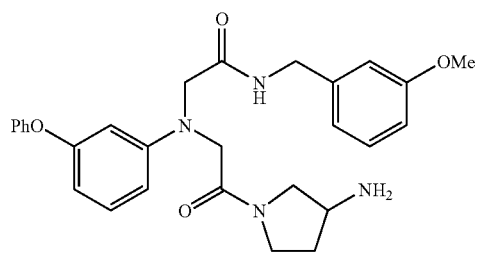
17G 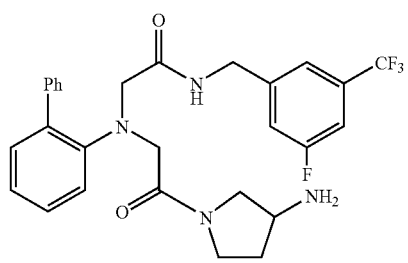
17H 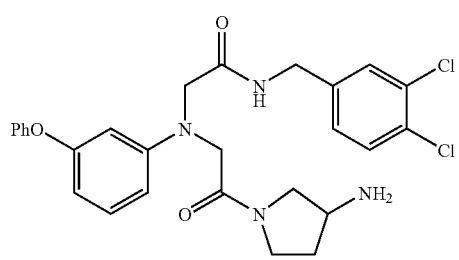
17I 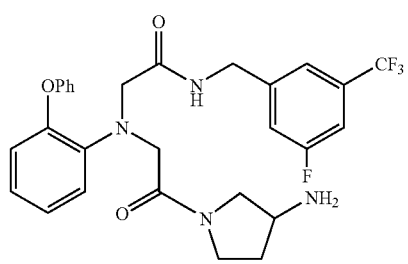
-continued
17J 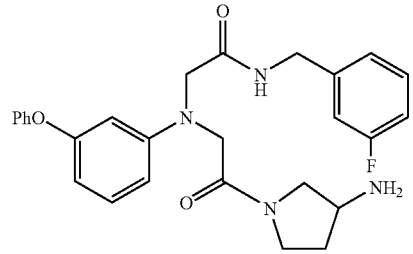
17K 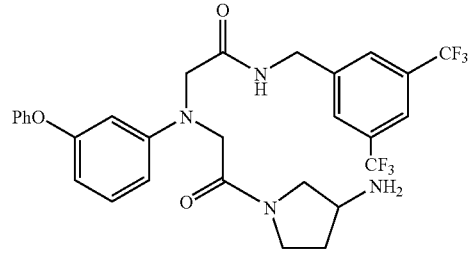
17L 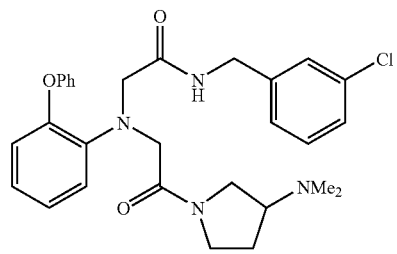
17M 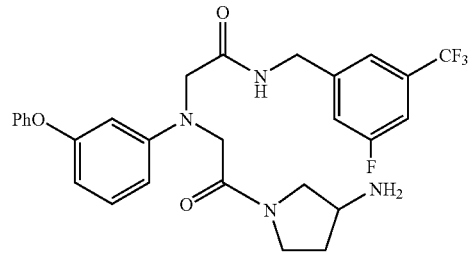
17N 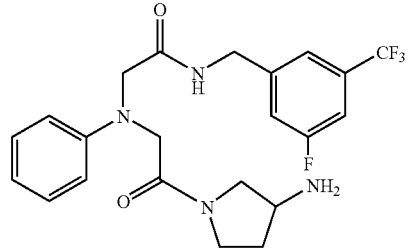
17O 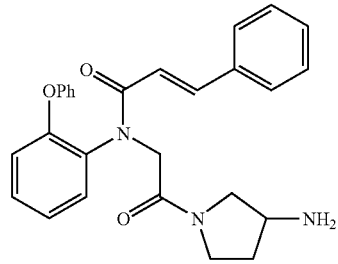

17P 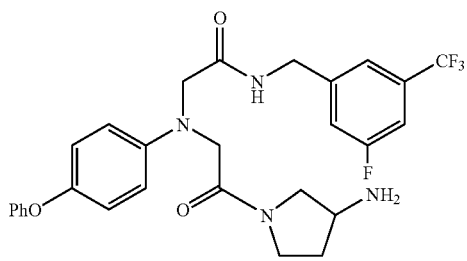
17Q 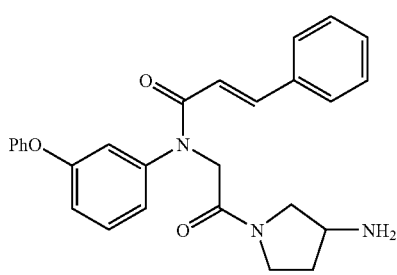
17R 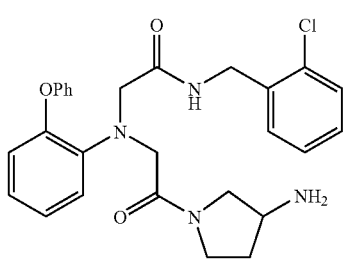
17S 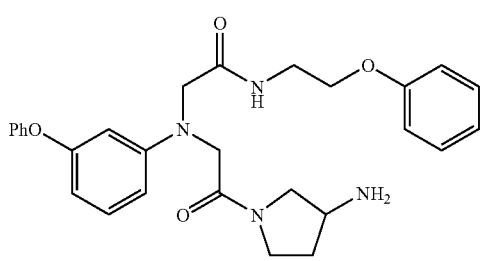
17T 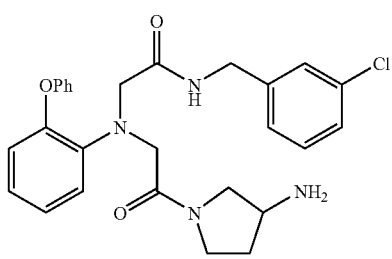
17U 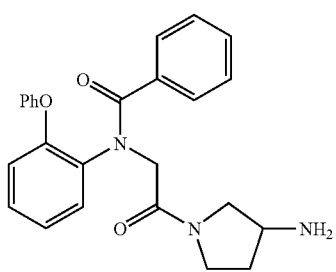
17V 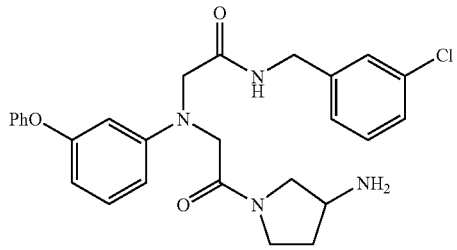
17W 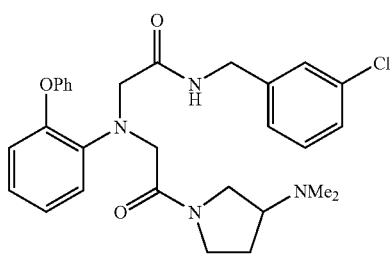
17X 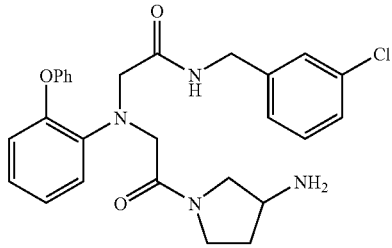
Example 18
The following compounds were synthesized by methods described herein or known in the art using the appropriate starting materials, reagents, intermediates and protecting groups, when necessary.
18A 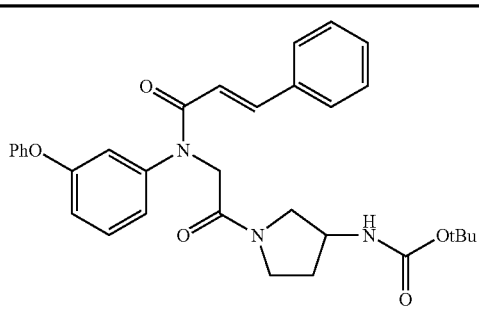
18B 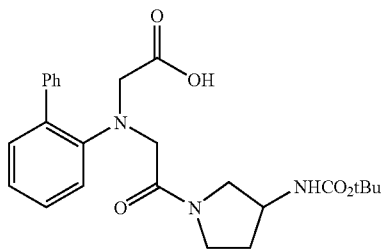

-continued
18C 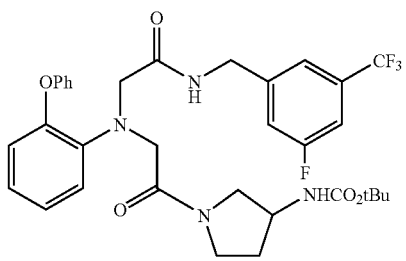
18D 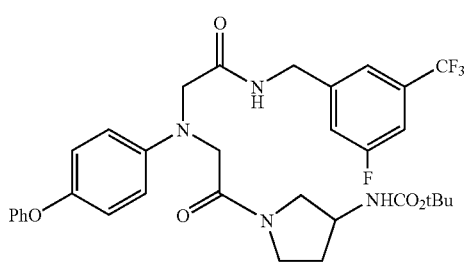
18E 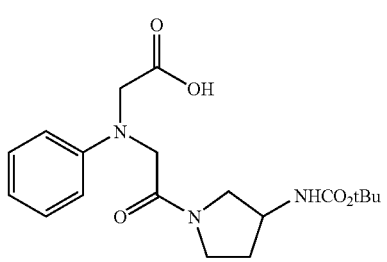
18F 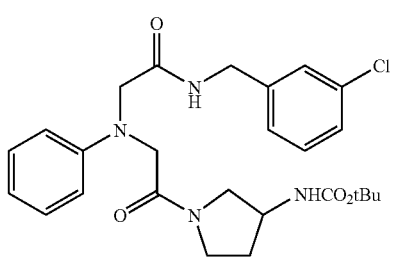
18G 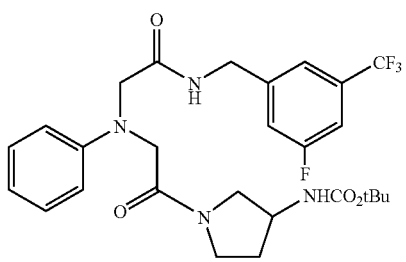
18H 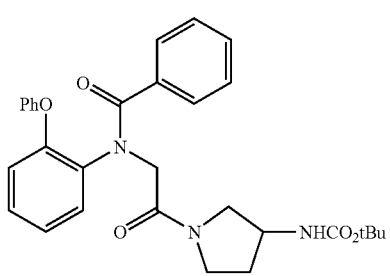
-continued
18I 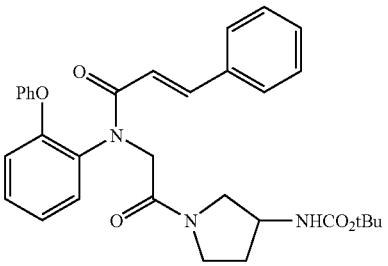
18J 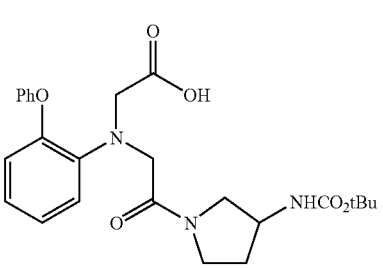
18K 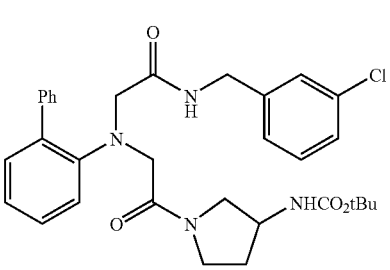
18L 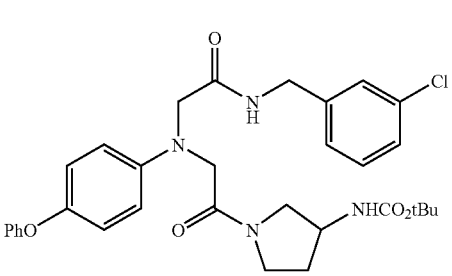
18M 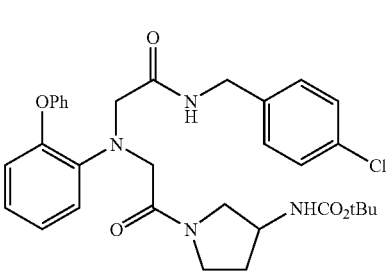
18N 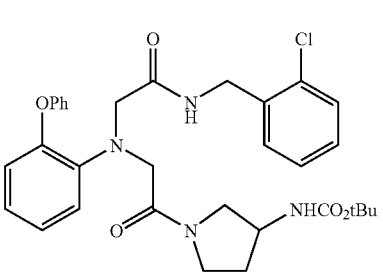

18O 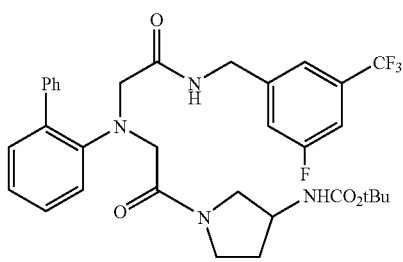
18P 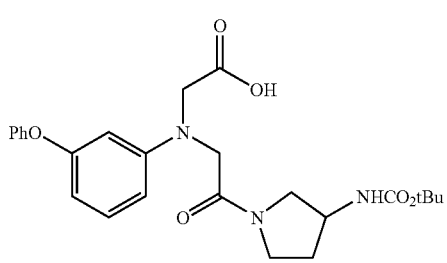
18Q 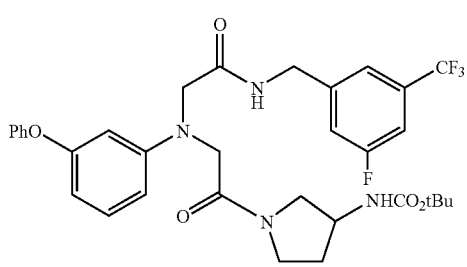
18R 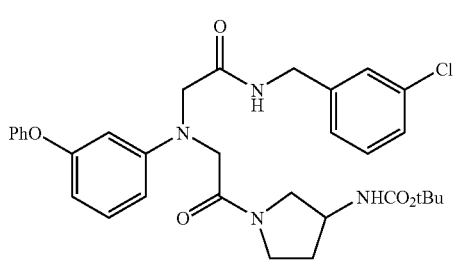
18S 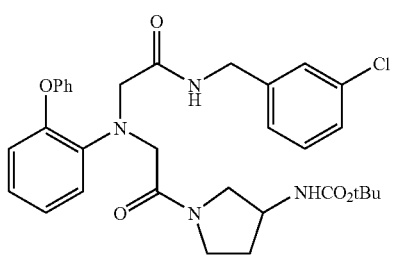
Example 19
The following compounds were synthesized by methods described herein or known in the art using the appropriate starting materials, reagents, intermediates and protecting groups, when necessary.
19A 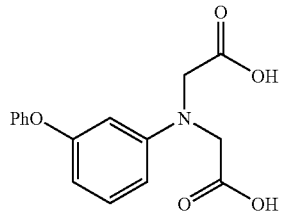
19B 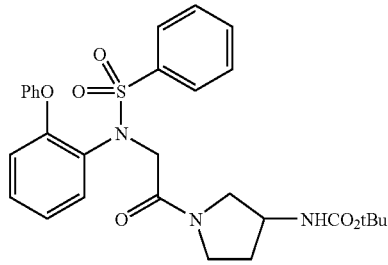
19C 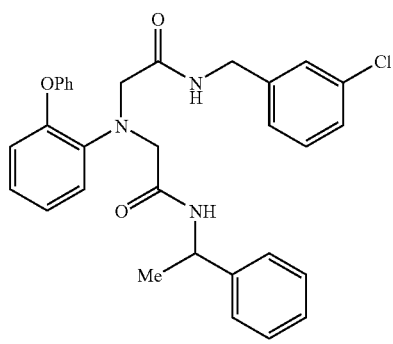
19D 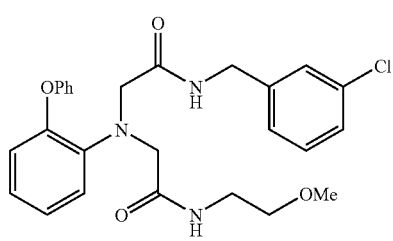
19E 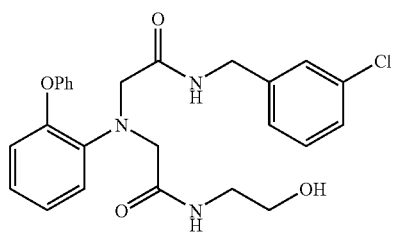
19F 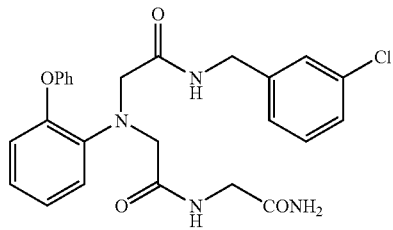

| | | | |
|---|---|---|---|
| 19G | 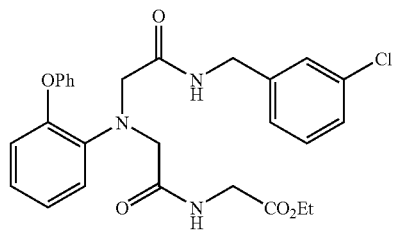 | 19M | 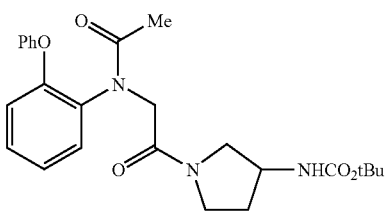 |
| 19H | 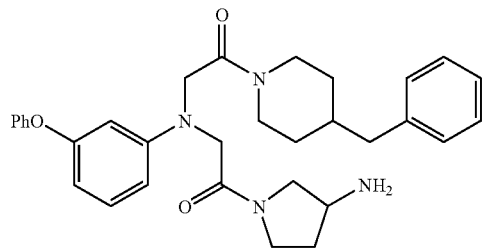 | 19N | 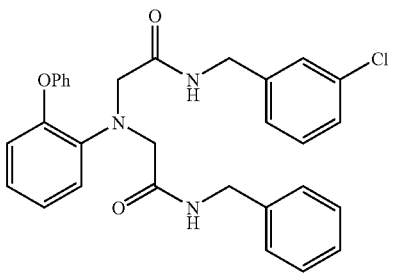 |
| 19I | 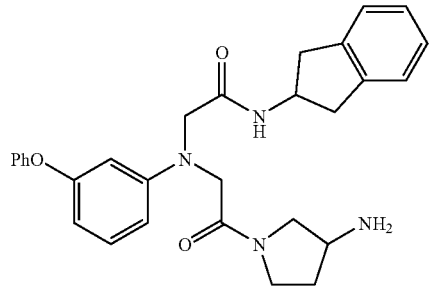 | 19O | 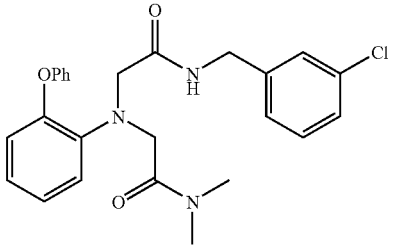 |
| 19J | 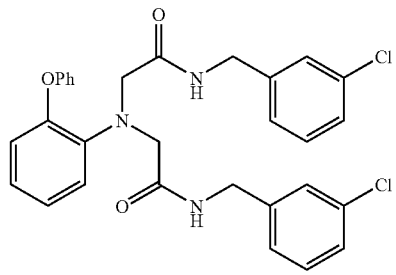 | 19P | 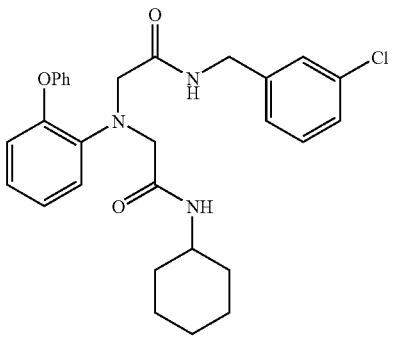 |
| 19K | 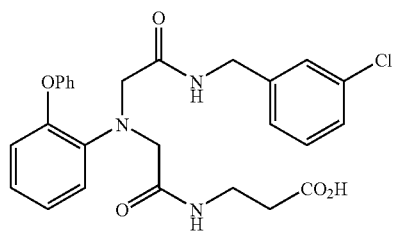 | 19Q | 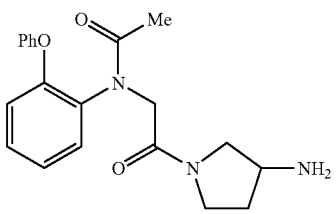 |
| 19L | 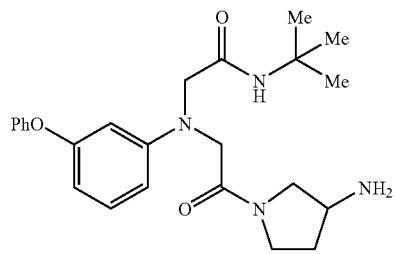 | 19R | 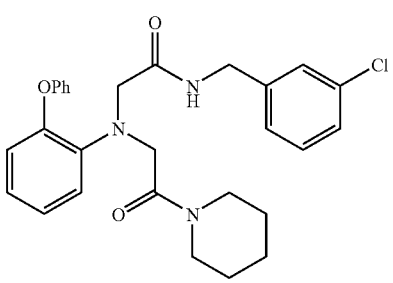 |

-continued
19S 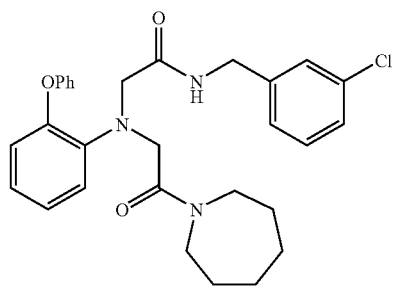
19T 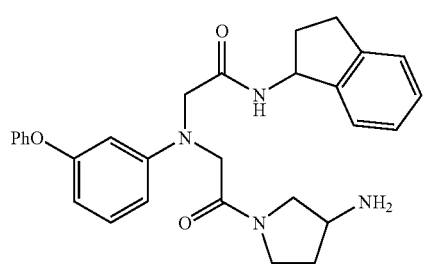
19U 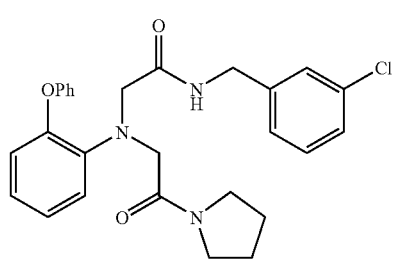
19V 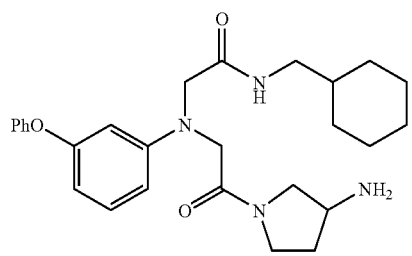
19W 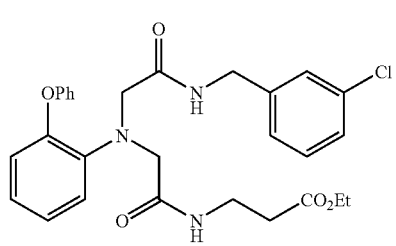
-continued
19X 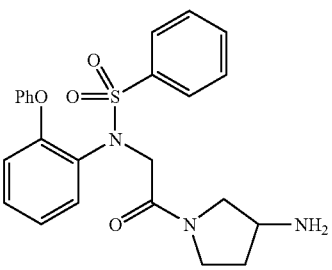
19Y 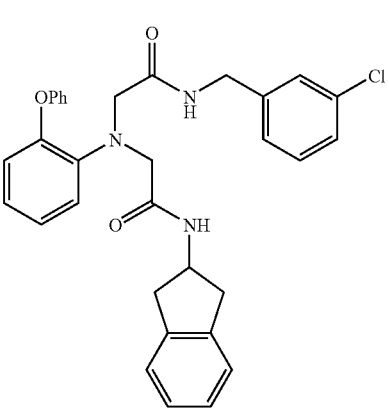
19Z 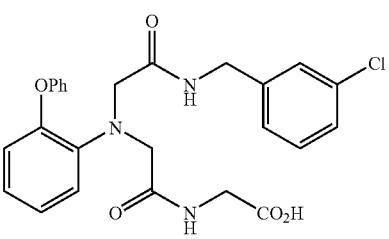
19AA 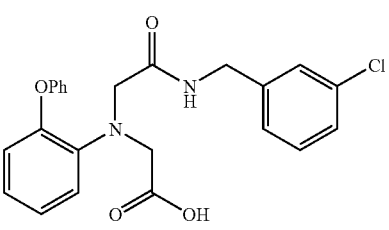
19AB 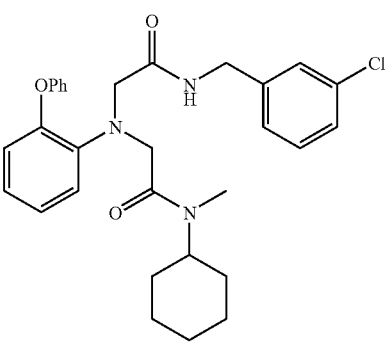

-continued

19AC 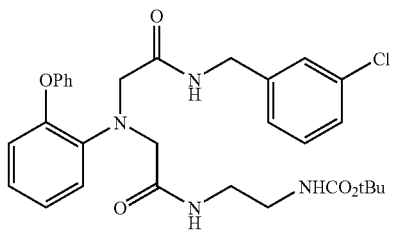

19AD 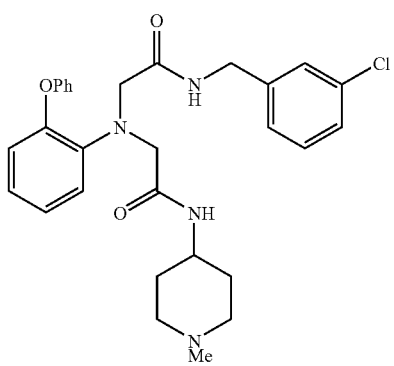

19AE 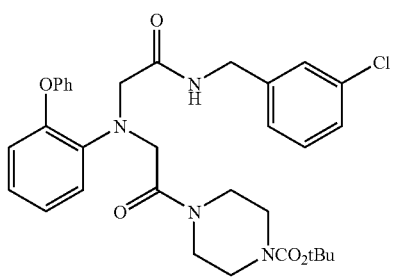

19AF 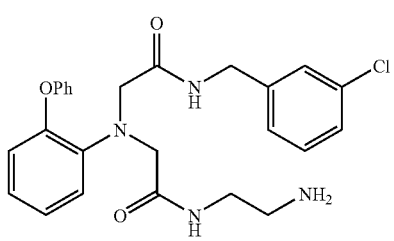

19AG 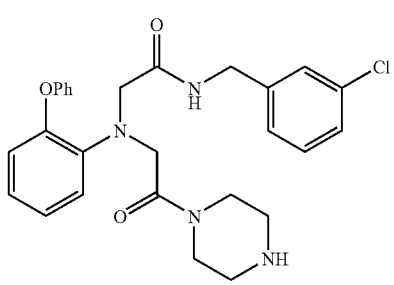

-continued

19AH 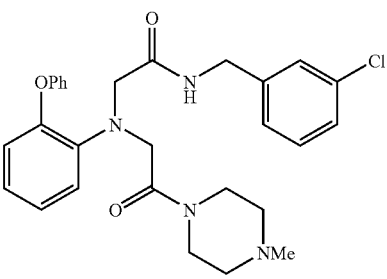

It should be understood that the above outlined processes are detailed solely for the purpose of illustrating the invention and are not limiting thereon. It will be appreciated by someone skilled in the art that by using similar or analogous reagents and/or conditions in various combinations, it will be possible to synthesize other derivatives encompassed in the general Formula I. The activity and selectivity of the compounds produced may be determined by any suitable assay known in the art.

It will also be appreciated that the chemical building blocks used in the synthesis of compounds of general Formula I are either commercially available or can be synthesized by methods known in the art.

II. Biological Screening

Example 1

Glucan Synthase Assay

The glucan synthase assay follows the incorporation of tritiated UDP-glucose into acid insoluble β-glucan as catalysed by the glucan synthase activity present in membrane preparations from *Candida albicans* and *Aspergillus fumigatus*. UDP-[$^3$H]-glucose (ca 0.01 μCi) is added to 100 μl assay buffer (50 mM Tris-Cl, pH8.0, 8% glycerol, 1 mM EDTA, 1.5 mM KF, 1 mM DTT, 20 μM GTPγS, 600 μM UDP-glucose) and the reaction initiated by the addition of 2 μl of enzyme preparation.

After incubation at 30° C. for 120 minutes, 10 μl of 30 mg/ml BSA is added with mixing and the reaction is terminated with 110 μl ice-cold 20% TCA. The precipitate is collected on a GF/B filter plate and washed three times with 200 μl water. Once dry, 200 μl of Microscint20 is added to each well and the plate is read on a Top-count scintillation counter.

Example 2

Proliferation Assay

Overnight cultures of organism were diluted back to an $OD_{600\,nm}$ of 0.1 in fresh media. Test compounds were added in a final concentration of 0.5% DMSO and the $OD_{600\,nm}$ was followed over 6 hours incubation at 25° C. Compounds described herein were screened to determine their activity as inhibitors of β-1,3-glucan synthase from *Candida albicans* and *Aspergillus fumigatus* and for their ability to inhibit the growth of *Candida albicans* and *Aspergillus fumigatus* whole organisms. The activities of various compounds described herein are shown in the Table below.

| Structure | C. albicans Glucan Synth IC$_{50}$ (μM) | A. fumigatus Glucan Synth IC$_{50}$ (μM) | C. albicans IC$_{50}$ (μM) | A. fumigatus IC$_{50}$ (μM) |
|---|---|---|---|---|
| OGT4325 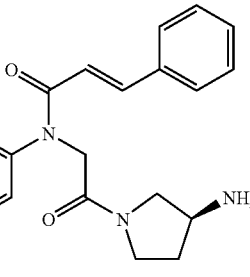 | 8.5 | 15.6 | 8 | NT |
| OGT4355 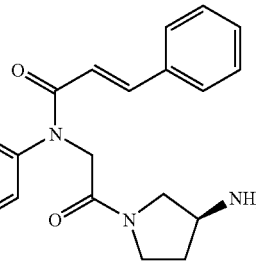 | 15 | 23 | 18 | 4 |
| OGT4344 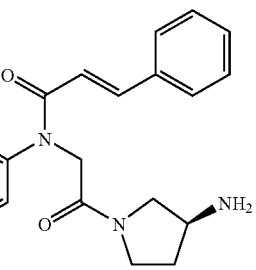 | 34 | 49 | 27 | 12 |
| OGT4165 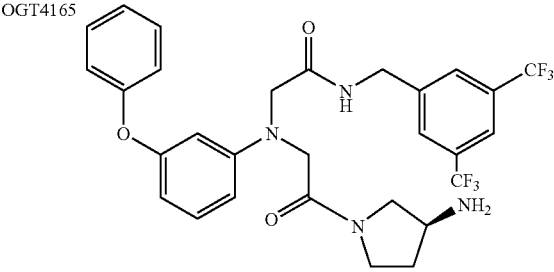 | 2.7 | 6.2 | 19 | 43 |
| OGT4154 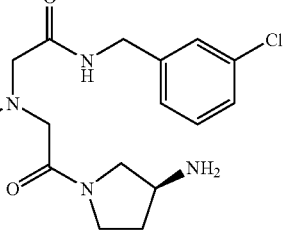 | 8 | 5.6 | 22 | 12 |

-continued

| Structure | C. albicans Glucan Synth IC$_{50}$ (µM) | A. fumigatus Glucan Synth IC$_{50}$ (µM) | C. albicans IC$_{50}$ (µM) | A. fumigatus IC$_{50}$ (µM) |
|---|---|---|---|---|
| OGT4155 | 5.4 | 5.2 | 17 | 14 |
| OGT3935 | 12 | 38 | 55 | 93 |

NT: not tested

Example 3

Glucan Biosynthesis Assay

This procedure confirms the specificity of the effects of the inhibitors by simultaneously following the incorporation of labelled acetate into fatty acids, and glucose into β-glucans in growing cultures of *Candida*. The fatty acids are extracted into solvent, and the glucan is released by treatment with β-glucanase preparations.

A 10 ml culture of *Candida* was grown in YPD media overnight at 30° C. The culture was diluted to $10^7$ cells/ml in 1 ml aliquots and continued to grow for a further 2 hours prior to the addition of test compound (Caspofungin −20 ng/ml, Cerulenin −10 µg/ml). After 30 min 1 µCi of each of $^{14}$C-glucose, $^{14}$C-acetate and $^3$H-N-acetyl-glucosamine were added. After a further 30 min, 500 µl of unlabelled 'carrier cells' from the overnight culture were added and the cells spun down and transferred to ice. Following 3 washes in ice-cold PBS, 250 µl of glass beads were added and the cells broken by 1 min shaking in a bead-beater.

For acetate labelling, the homogenate was extracted for 1 hour with an equal volume of choroform:methanol (1:1). The organic layer was washed with water and 50 µl was removed to 2 ml scintillant for counting.

For glucose labelling, the cell-wall pellet was washed (spun at 16000 g for 2 min) 3 times in 5% NaCl, an 3 times in 1 mM EDTA. The pellet was resuspended in 200 µl 10 mM Na$_2$PO$_4$, pH7.5/150mM NaCl/5 mM EDTA/2 mM DTT containing 5 µl of Quantazyme. After an overnight incubation at room temperature a sample of the solubilised label was added to scintillant and counted.

FIG. 1 shows the inhibition of glucose incorporation into β-1,3-D-glucan in *Candida Albicans* strain CAF2-1. OGT4154 preferentially inhibits β-1,3-D-glucan biosynthesis in *Candida Albicans*.

Example 4

Evaluation of OGT 4154 in an Animal Model

Six-week-old, specific pathogen-free female Swiss ICR (CD1) mice are housed in groups of five per cage and allowed free access to food and water to acclimate 7 days before the initiation of experiments. At the time of the study, the animals weigh 23-27 g.

In order to mimic the immunocompromised state common to many subjects at high risk of a fungal infection, a profound state of granulocytopenia is produced in animals to maximize the growth of *Candida* in the mice. This immuno-compromised state is achieved by administration of cyclophosphamide to the mice prior to infection. Cyclophosphamide is administered via intraperitoneal injection four days (150 mg/kg) and one day (100 mg/kg) before the day of infection. The degree and duration of neutropenia is confirmed by monitoring neutrophil counts of peripheral blood smears with a hemocytometer daily throughout the duration of the study.

In order to initiate the *Candida* infection, neutropenic mice are placed head first into a mouse restraint device with the tail extending freely hanging through the other end. The tail is immersed in warm (50° C.) water bath for 5-10 s to dilate the veins. Using a (1 mL) tuberculin syringe with either a 26- or 27-gauge needle the inoculum (0.1 mL of a suspension of $10^{5-7}$ CFU/mL *Candida* blastospores) is injected via the lateral tail vein. The animals are monitored at least every six hours after infection for the remainder of the study period.

Pharmacokinetic Studies

Three groups of six animals (corresponding to three dose regimens) are administered a compound of Formula I by oral gavage at a dose of 0.1, 0.5, or 3 mg/kg. Afterwards, blood is sampled at 1, 3, 6, 12, 18, 24, and 36 hours post-administration. Blood from groups of three mice is sampled at each sampling time point. At the next time point the second group of three mice is sampled. Thus, any one mouse is sampled only three or four times to minimize the impact of blood loss on drug concentrations. Before sampling, the animals are anesthetized with a few drops of halothane on a bell jar. Blood (50 µL per time point) is collected in heparinized capillary tubes (Fisher Scientific, Pittsburgh, Pa.) from the orbital venous plexus. The volume of blood collected form any individual animal is less then 5% of the total blood volume.

The tubes are immediately centrifuged in a capillary centrifuge at 10,000×g for 4-5 minutes, the serum with a micropipet, placed in the wells of a 96-well microtiter plate and frozen at −80° C. until the assay for OGT 4154 is performed.

Levels of the compound in each sample are then evaluated by HPLC. An assay of six to eight standards of drug-spiked serum (twofold escalating concentrations) to create a standard curve is similarly assayed. The lower limit of detection for the assay is defined, and the intra- and interday variation calculated. Pharmacokinetic constants for each drug dose level are calculated using the drug concentrations from the individual mouse samples. The elimination half-life in the postdistributive phase is calculated using a noncompartment model and an unweighted least linear squares method. The AUC is calculated using the linear trapezoidal rule up to the final measured concentration and then extrapolated to infinity.

Analysis of Binding to Serum Protein

Since serum protein binding of anti-infective drugs can reduce antimicrobial activity, restrict tissue distribution, and delay drug elimination, protein-binding studies of a compound of Formula I are performed on the serum of neutropenic mice using an ultrafiltration method. After the mouse serum samples are spiked with a series of drug concentrations, one mL aliquots is filtered by centrifugation through Millipore YM10 filter device (10,000 MW exclusion) (Millipore Corp. Bedford, Mass. using a fixed angle rotor at 5000×g for five minutes. The concentration of OGT 4154 in serum and in ultrafiltrate to determine the degree of protein binding at each of the drug concentrations, where the percentage of protein bound drug is calculated as:

% Protein Bound Drug=([Serum]−[Ultrafiltrate])/[Serum]×100

Evaluation of Therapeutic Efficacy in Neutropenic Mice

A compound of Formula I at escalating doses (10-100 mg/kg) or vehicle are administered to neutropenic mice by oral gavage two hours after infection with *Candida* as described above. This delay after infection allows the cells to enter the early log phase of growth in the mouse kidneys. Antifungal efficacy is assessed by comparison to the microbiological clearance of *Candida* from kidneys in treated vs untreated control mice. At the end of therapy, animals are euthanized by $CO_2$ asphyxiation. Both kidneys are aseptically removed and placed in 3.4 mil of sterile cold 0.9% NaCl (an initial 1-10 dilution based on weight of kidneys). The kidney tissue is then homogenized using a Polytron homogenizer for 20 seconds. After homogenization of each tube, the grinder bit is washed with 70% ethanol followed by fresh tap water. This method prevents significant organism carryover from sample to sample.

Each tissue homogenate is then serially diluted 10-fold from 1/10 to $1/10^6$ in sterile 0.9% NaCl. The dilutions are plated in duplicated on SD agar plates for determination of viable fungal colony counts after incubation at 37° C. for 24 hours.

Colony counts are expressed as the mean±standard deviation $\log_{10}$ CFU/kidney. Previous studies with this series of dilutions have demonstrated that the method is sensitive to detection of 100 CFU/kidneys.

Example 5

Human Clinical Trial of Safety

Objective: To determine the safety and pharmacokinetics of orally administered a compound of Formula I.

Clinical Trial Participants

Thirty healthy volunteers ranging between 20-40 years of age and weighing between 60-90 kg are enrolled study. The subjects will have no clinically significant abnormal laboratory values for hematology or serum chemistry, and a negative urine toxicology screen, HIV screen, and hepatitis B surface antigen screen. They should not have any evidence of the following: hypertension; a history of any primary hematologic disease; history of significant hepatic, renal, cardiovascular, gastrointestinal, genitourinary, metabolic, neurologic disease; habitual and heavy consumption of beverages containing caffeine; participation in any other clinical trial or had blood transfused or donated within 30 days of study entry; or have significant abnormalities on the pre-study physical examination or the clinical laboratory evaluations within 14 days of study entry. All subjects are evaluated for safety and all blood collections of pharmacokinetic analysis are collected as scheduled. All studies are performed with institutional ethics committee approval and patient consent.

Study Design This is a Phase I, single center, open label, randomized study in healthy male volunteers. Thirty subjects are randomly assigned to one of three dosing groups (0.2, 0.5, or 1.5 mg/kg). A compound of Formula I is administered orally. Additional dosing, dosing frequency, or other parameter may be added to the study as desired by including additional groups of subjects. Subjects are confined to the study center for at least 12 hours prior to and 72 hours following dosing for the study period.

Blood Sampling Serial blood is drawn by direct vein puncture before and after administration of a compound of Formula I. Venous blood samples (5 mL) for determination of serum concentrations of the compound of Formula I are obtained at about 20 minutes prior to dosing (baseline sample) and at 1, 2, 5, 8, 12,15, 18, 24, 30, 36, 48, 60, and 72 hours after dosing. Each serum sample is divided into two aliquots. All serum samples are stored at −20° C. Serum samples are shipped on dry ice. Fasting clinical laboratory tests (hematology, serum chemistry, and urinanalysis) are performed immediately prior to dosing, the morning of day 4 following dosing, and the morning of day 7 following dosing.

Bioanalytical Methods An HPLC assay is used to determine serum concentrations of a compound of Formula I.

Safety Determinations Vital signs are recorded immediately prior to dosing, and at 6, 24, 48, and 72 hours after each dosing. Safety determinations are based on the incidence and type of adverse events and the changes in clinical laboratory tests from baseline. In addition, changes from pre-study vital sign measurements, including blood pressure, and physical examination results are evaluated.

Data Analysis Pharmacokinetic parameters are calculated by model independent methods using the latest version of the BIOAVL software. The following pharmacokinetic parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; estimated by linear regression of consecutive data points in the terminal linear region of the log-linear concentration-time plot. The mean, standard deviation (SD), and coefficient of variation (CV) of the pharmacokinetic parameters are calculated for each treatment.

III. Pharmaceutical Compositions

Example 1a

Parenteral Composition

To prepare a parenteral pharmaceutical composition suitable for administration by injection, 100 mg of a water-soluble salt of any compound of Formula I, is dissolved in DMSO and then mixed with 10 mL of 0.9% sterile saline. The mixture is incorporated into a dosage unit form suitable for administration by injection.

Example 1b

Oral Composition

To prepare a pharmaceutical composition for oral delivery, 100 mg of any compound of Formula I, is mixed with 750 mg of starch. The mixture is incorporated into an oral dosage unit for, such as a hard gelatin capsule, which is suitable for oral administration.

Example 1c

Sublingual (Hard Lozenge) Composition

To prepare a pharmaceutical composition for buccal delivery, such as a hard lozenge, mix 100 mg of any compound of Formula I, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 1d

Inhalation Composition

To prepare a pharmaceutical composition for inhalation delivery, 20 mg of any compound of Formula I, is mixed with 50 mg of anhydrous citric acid and 100 mL of 0.9% sodium chloride solution. The mixture is incorporated into an inhalation delivery unit, such as a nebulizer, which is suitable for inhalation administration.

Example 1e

Rectal Gel Composition

To prepare a pharmaceutical composition for rectal delivery, 100 mg of any compound of Formula I, is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 1f

Topical Gel Composition

To prepare a pharmaceutical topical gel composition, 100 mg of any compound of Formula I, is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topic1 administration.

Example 1g

Ophthalmic Solution Composition

To prepare a pharmaceutical opthalmic solution composition, 100 mg of any compound of Formula I, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of this application and scope of the appended claims. All publications, patents, and patent applications cited herein are hereby incorporated by reference for all purposes.

What is claimed is:

1. A compound having the structure of Formula I:

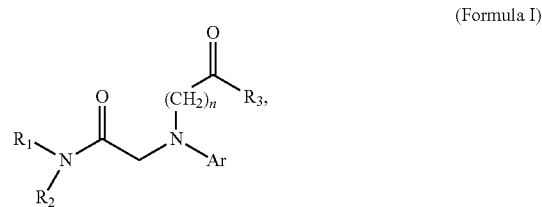

(Formula I)

wherein, n is 0;

$R_1$ and $R_2$ together with the nitrogen atom to which they are attached form a 4- to 8-membered heterocycloalkyl or heterocycloalkenyl group which is optionally substituted with 1 or 2 independently selected $R_x$ groups;

Ar is phenyl that is substituted with $OCH_2$-phenyl wherein the $OCH_2$-phenyl is optionally substituted with 1 or 2 independently selected $R_x$ groups;

$R_3$ is $L_1$-$L_2$-$R_4$, where $L_1$ a bond;

$L_2$ is selected from a bond, $(C_1$-$C_6)$alkyl, $(C_2$-$C_6)$alkenyl, $(C_2$-$C_6)$alkynyl, $(C_1$-$C_6)$heteroalkyl, $(C_2$-$C_6)$heteroalkenyl, $(C_3$-$C_8)$cycloalkyl, $(C_3$-$C_8)$cycloalkenyl, $(C_2$-$C_8)$heterocycloalkyl and $(C_2$-$C_8)$heterocycloalkenyl; wherein the $(C_1$-$C_6)$alkyl, $(C_2$-$C_6)$alkenyl, $(C_2$-$C_6)$alkynyl, $(C_1$-$C_6)$heteroalkyl, $(C_2$-$C_6)$heteroalkenyl, $(C_3$-$C_8)$cycloalkyl, $(C_3$-$C_8)$cycloalkenyl, $(C_2$-$C_8)$heterocycloalkyl, and $(C_2$-$C_8)$heterocycloalkenyl is optionally substituted with 1 or 2 independently selected $R_x$ groups;

$R_4$ is selected from H, cycloalkyl, cycloalkenyl, heterocycloalkyl, heterocycloalkenyl, aryl, and heteroaryl, wherein the cycloalkyl, cycloalkenyl, heterocycloalkyl, heterocycloalkenyl, aryl, and heteroaryl is optionally substituted with 1 or 2 independently selected $R_x$ groups;

$R_x$ is $L_{s1}L_{s2}R_s$, wherein each $L_{s1}$ and $L_{s2}$ is independently selected from a bond, —O—, —C(=O)—, —S—, —S(=O)—, —S(=O)$_2$—, —NH—, —NHC (O)—, —C(O)NH—, S(=O)₂NH—, —NHS(=O)₂, —OC(O)NH—, —NHC(O)O—, (C₁-C₆) alkyl, and —(C₂-C₆) alkenyl; and $R_s$ is selected from hydrogen, alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, isocyanato, thiocyanato, isothiocyanato, nitro, perhaloalkyl, perfluoroalkyl, silyl, and amino, including mono- and di-substituted amino groups;

or a pharmaceutically acceptable salt, tautomer, or optical isomer thereof.

2. A pharmaceutically acceptable salt according to the compound of claim 1.

3. The compound of claim 1, wherein $R_1$ and $R_2$ together with the nitrogen atom to which they are attached form a heterocycloalkyl group selected from:

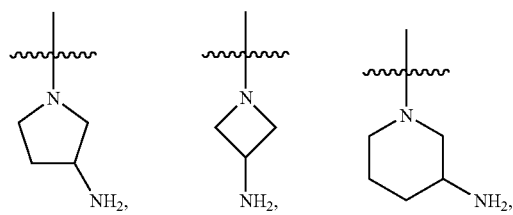

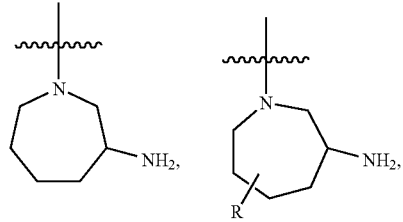

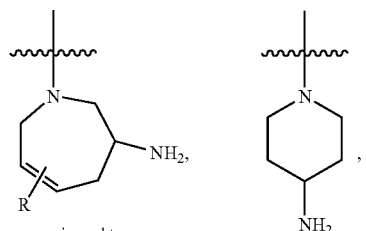

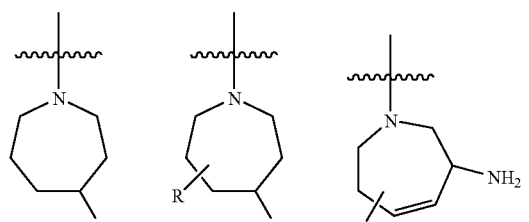

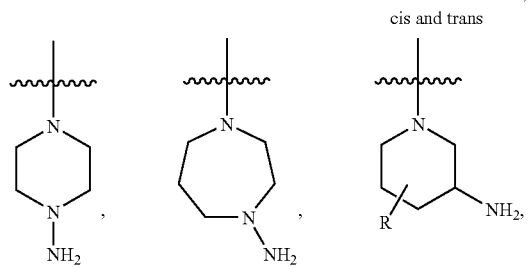

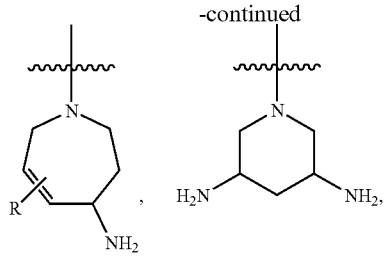

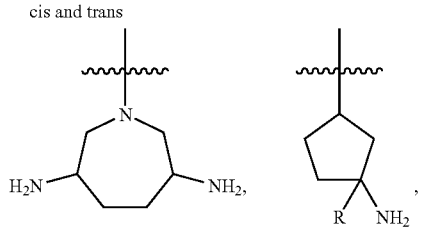

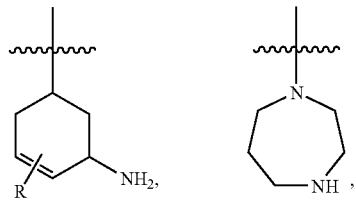

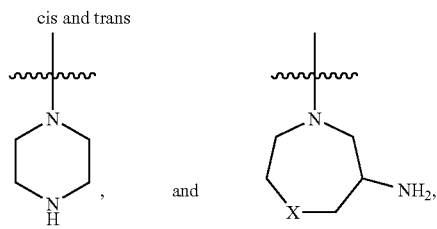

wherein:
each NH₂ group is optionally substituted with a C₁-C₆ alkyl group;
X is O, NR or SO₂, and
each R is independently selected from hydrogen, halo, —OH, —NH₂, —SH, —S(C₁-C₆ alkyl), —NH(C₁-C₆ alkyl), —N(C₁-C₆ alkyl)₂, C₁-C₆ alkyl, C₁-C₆ haloalkyl, and C₁-C₆ heteroalkyl.

4. The compound of claim 3, wherein each R is independently selected from hydrogen and C₁-C₆ alkyl and each NH₂ group is unsubstituted.

5. The compound of claim 3, wherein the heterocycloalkyl group is:

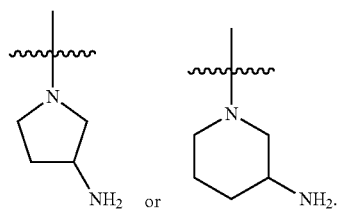

6. The compound of claim 1, wherein Ar is a phenyl group that is substituted with —OCH₂-phenyl wherein the —OCH₂-phenyl is optionally substituted with halo, C₁-C₆ alkyl, hydroxy, —O(C₁-C₆ alkyl), —CO₂H, or —CO₂(C₁-C₆ alkyl).

7. The compound of claim 1, wherein $R_4$ is a phenyl group optionally substituted with one or two groups independently selected from halogen, $C_1$-$C_6$ alkyl, hydroxy, —O($C_1$-$C_6$ alkyl), —NH$_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl)COH, —N($C_1$-$C_6$ alkyl)CO($C_1$-$C_6$ alkyl), —NH SO$_2$H, —NHSO$_2$($C_1$-$C_6$ alkyl), —N($C_1$-$C_6$ alkyl)SO$_2$H, —N($C_1$-$C_6$ alkyl) SO$_2$($C_1$-$C_6$ alkyl), —CONH$_2$, —CONH($C_1$-$C_6$ alkyl), —CON($C_1$-$C_6$ alkyl)$_2$, and SO$_2$($C_1$-$C_6$ alkyl).

8. The compound of claim 1 according to Formula II:

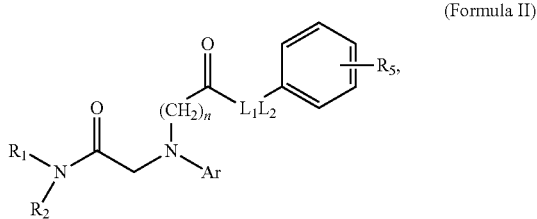

(Formula II)

wherein:

n is 0; and $R_5$ is selected from halogen, $C_1$-$C_6$ alkyl, hydroxy, —O($C_1$-$C_6$ alkyl), —NH$_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —N($C_1$-$C_6$ alkyl) COH, —N($C_1$-$C_6$ alkyl)CO($C_1$-$C_6$ alkyl), —NH SO$_2$H, —NHSO$_2$($C_1$-$C_6$ alkyl), —N($C_1$-$C_6$ alkyl)SO$_2$H, —N($C_1$-$C_6$ alkyl) SO$_2$($C_1$-$C_6$ alkyl), —CONH$_2$, —CONH($C_1$-$C_6$ alkyl), —CON($C_1$-$C_6$ alkyl)$_2$, and SO$_2$ ($C_1$-$C_6$ alkyl).

9. The compound of claim 1 according to Formula IV or Formula V:

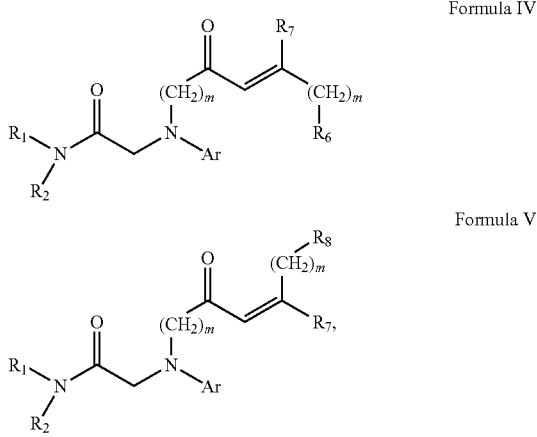

Formula IV

Formula V wherein:

$R_7$ is hydrogen, halo, or $C_1$-$C_6$ alkyl;

$R_8$ is a phenyl group optionally substituted with one or two groups independently selected from halo, $C_1$-$C_6$ alkyl, hydroxy, —O($C_1$-$C_6$ alkyl), —NH$_2$, —NH($C_1$-$C_6$ alkyl), —N($C_1$-$C_6$ alkyl)($C_1$-$C_6$ alkyl), —($C_1$-$C_6$ haloalkyl), —NHCOH, —NHCO($C_1$-$C_6$ alkyl), —CONH$_2$, —CONH($C_1$-$C_6$ alkyl), —CON($C_1$-$C_6$ alkyl)$_2$, and SO$_2$($C_1$-$C_6$ alkyl); and m is 0.

10. A compound having the structure according to the following formula:

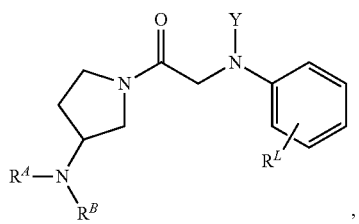

wherein:

Y is —COZ;

Z is selected from the group consisting of Ph, —($C_1$-$C_3$) alkyl-Ph and —CH=CHPh, wherein Ph is substituted with $R^C$ and $R^D$ which are independently selected from the group comprising hydrogen, halo, $C_1$-$C_6$ alkyl, $OR^E$, $NR^G R^H$, $NR^G COR^W$, $NR^G SO_2 R^W$, $CONR^G R^H$ and $SO_2 R^W$;

$R^L$ is selected from the group consisting of hydrogen, halogen, Ph, OPh and OCH$_2$Ph, wherein Ph is optionally substituted with halogen, $C_1$-$C_6$ alkyl, $OR^E$ or $CO_2 R^E$;

$R^A$ and $R^B$ are independently selected from hydrogen, $C_1$-$C_6$ alkyl and $CO_2 R^F$;

$R^E$ is hydrogen or $C_1$-$C_6$ alkyl;

$R^F$ is $C_1$-$C_6$ alkyl;

$R^G$ and $R^H$ are independently hydrogen or $C_1$-$C_6$ alkyl, or together form a 5- or 6-membered ring which optionally contains one further heteroatom selected from $NR^E$, S and O; and $R^W$ is $C_1$-$C_6$ alkyl.

11. A compound having the structure according to the following formula:

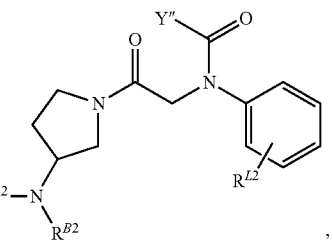

wherein

Y" is selected from the group comprising Ph, —($C_1$-$C_3$) alkyl-Ph and —CH=CHPh, wherein Ph is substituted with $R^{C2}$ and $R^{D2}$ which are independently selected from the group comprising hydrogen, halogen, $C_1$-$C_6$ alkyl, $OR^{E2}$, $NR^{G2}R^{H2}$, $NR^{G2}COR^{W2}$, $NR^{G2}SO_2 R^{W2}$, $CONR^{G2}R^{H2}$ and $SO_2 R^{W2}$;

$R^{L2}$ is selected from the group consisting of hydrogen, halogen, Ph, OPh and OCH$_2$Ph, wherein Ph is optionally substituted with halogen, $C_1$-$C_6$ alkyl, $OR^{E2}$ or $CO_2 R^{E2}$;

$R^{E2}$ and $R^{B2}$ are independently selected from hydrogen, $C_1$-$C_6$ alkyl and $CO_2 R^{F2}$;

$R^{E2}$ is hydrogen or $C_1$-$C_6$ alkyl;

$R^{F2}$ is $C_1$-$C_6$ alkyl;

$R^{G2}$ and $R^{H2}$ are independently hydrogen or $C_1$-$C_6$ alkyl, or together form a 5- or 6-membered ring which optionally contains one further heteroatom selected from $NR^{E2}$, S and O; and $R^{W2}$ is $C_1$-$C_6$ alkyl.

12. The compound of claim 11, wherein:

Y" is —CH=CHPh where the Ph group is substituted with $R^{C2}$ and $R^{D2}$ which are independently selected from the group comprising hydrogen, halogen, $C_1$-$C_6$ alkyl, $OR^{E2}$, $NR^{G2}R^{H2}$, $NR^{G2}COR^{W2}$, $NR^{G2}SO_2R^{W2}$, $CONR^{G2}R^{H2}$ and $SO_2R^{W2}$;

$R^{A2}$ is hydrogen or $C_1$-$C_6$ alkyl;

$R^{B2}$ is hydrogen or $C_1$-$C_6$ alkyl; and $R^{L2}$ is Ph or OPh, wherein Ph is optionally substituted with halogen, $C_1$-$C_6$ alkyl, $OR^{E2}$ or $CO_2R^{E2}$.

13. The compound of claim 12, wherein $R^{C2}$ and $R^{D2}$ are each independently selected from the group consisting of hydrogen, halogen and $C_1$-$C_6$ alkyl and $R^{A2}$ and $R^{B2}$ are both hydrogen.

14. A pharmaceutical composition comprising a compound according to claim 1, and a pharmaceutically acceptable diluent or carrier.

15. The compound of claim 1 wherein $L_2$ is ($C_2$-$C_6$)alkenyl that is optionally substituted with 1 or 2 independently selected $R_x$ groups.

16. A pharmaceutical composition comprising a compound according to claim 15, and a pharmaceutically acceptable diluent or carrier.

17. The compound of claim 1 wherein $L_2$ is ($C_2$-$C_6$)alkynyl that is optionally substituted with 1 or 2 independently selected $R_x$ groups.

18. The compound of claim 1 wherein $R_4$ is aryl that is optionally substituted with 1 or 2 independently selected $R_x$ groups.

19. The compound of claim 1 wherein $R_1$ and $R_2$ together with the nitrogen atom to which they are attached form a 5 membered heterocycloalkyl or heterocycloalkenyl group.

20. The compound of claim 1 wherein $R_1$ and $R_2$ together with the nitrogen atom to which they are attached form a 6 membered heterocycloalkyl or heterocycloalkenyl group.

21. The compound of claim 1 wherein $R_1$ and $R_2$ together with the nitrogen atom to which they are attached form a 7 membered heterocycloalkyl or heterocycloalkenyl group.

22. The compound of claim 1 wherein $R_1$ and $R_2$ together with the nitrogen atom to which they are attached form a 8 membered heterocycloalkyl or heterocycloalkenyl group.

* * * * *